United States Patent
Lum et al.

(10) Patent No.: US 12,324,836 B2
(45) Date of Patent: Jun. 10, 2025

(54) METHODS AND COMPOSITIONS FOR VACCINATING AND BOOSTING CANCER PATIENTS

(71) Applicant: TransTarget, Inc., Sunnyvale, CA (US)

(72) Inventors: Lawrence G. Lum, Sunnyvale, CA (US); Manley Huang, Sunnyvale, CA (US)

(73) Assignee: TRANSTARGET, INC., Sunnyvale, CA (US)

( * ) Notice: Subject to any disclaimer, the term of this patent is extended or adjusted under 35 U.S.C. 154(b) by 509 days.

(21) Appl. No.: 16/467,003

(22) PCT Filed: Dec. 7, 2017

(86) PCT No.: PCT/US2017/065177
§ 371 (c)(1),
(2) Date: Jun. 5, 2019

(87) PCT Pub. No.: WO2018/106958
PCT Pub. Date: Jun. 14, 2018

(65) Prior Publication Data
US 2019/0343954 A1 Nov. 14, 2019

Related U.S. Application Data

(60) Provisional application No. 62/497,879, filed on Dec. 7, 2016.

(51) Int. Cl.
| | | |
|---|---|---|
| A61K 39/395 | (2006.01) |
| A61K 39/00 | (2006.01) |
| A61K 40/11 | (2025.01) |
| A61K 40/42 | (2025.01) |
| C07K 16/28 | (2006.01) |
| C07K 16/32 | (2006.01) |

(52) U.S. Cl.
CPC ........ *A61K 39/39558* (2013.01); *A61K 40/11* (2025.01); *A61K 40/4205* (2025.01); *C07K 16/2809* (2013.01); *C07K 16/32* (2013.01); *A61K 2039/505* (2013.01); *A61K 2039/515* (2013.01); *A61K 2039/545* (2013.01); *A61K 2239/31* (2023.05); *A61K 2239/38* (2023.05); *A61K 2239/49* (2023.05); *C07K 2317/31* (2013.01)

(58) Field of Classification Search
CPC .............. A61K 39/39558; A61K 35/17; A61K 2039/505; A61K 2039/515; A61K 2039/545; C07K 16/2809; C07K 16/32; C07K 2317/31; A61P 35/00
See application file for complete search history.

(56) References Cited

U.S. PATENT DOCUMENTS

| | | | | |
|---|---|---|---|---|
| 7,763,243 B2* | 7/2010 | Lum | .................. | C07K 16/3007 424/178.1 |
| 2002/0006409 A1* | 1/2002 | Wood | ..................... | A61P 35/00 424/93.7 |
| 2002/0086012 A1 | 7/2002 | Wels et al. | | |
| 2009/0317407 A1* | 12/2009 | LaCelle | ................. | C07K 16/26 424/174.1 |
| 2014/0329310 A1* | 11/2014 | Lum | .................... | C12N 5/0636 435/325 |
| 2016/0237407 A1 | 8/2016 | Wagner et al. | | |

FOREIGN PATENT DOCUMENTS

| | | | | |
|---|---|---|---|---|
| WO | WO-03015705 A2 * | 2/2003 | ........... | A61K 38/193 |
| WO | WO-2015188119 A1 * | 12/2015 | ......... | A61K 31/4745 |

OTHER PUBLICATIONS

Ponce et al. Adverse Consequences of Immuno-stimulation. Journal of Immunotoxicology, 5:33-41, 2008 (Year: 2008).*
Su et al. A Positive Feedback Loop between Mesenchymal-like Cancer Cells and Macrophages Is Essential to Breast Cancer Metastasis. Cancer Cell 25, 605-620, May 12, 2014. (Year: 2014).*
Written Opinion mailed Feb. 20, 2018 from the International Searching Authority in International Patent Application No. PCT/US2017/065177, filed Dec. 7, 2017, 6 pages.
Search Report mailed Feb. 20, 2018, from the International Searching Authority in International Patent Application No. PCT/US2017/065177, filed Dec. 7, 2017, 2 pages.
Morgan, Richard A., et al. "Case report of a serious adverse event following the administration of T cells transduced with a chimeric antigen receptor recognizing ERBB2." Molecular therapy 18.4 (2010): 843-851.
Kalos, Michael, and Carl H. June. "Adoptive T cell transfer for cancer immunotherapy in the era of synthetic biology." Immunity 39.1 (2013): 49-60.
Taniguchi, Koji, and Michael Karin. "IL-6 and related cytokines as the critical lynchpins between inflammation and cancer." Seminars in immunology. vol. 26. No. 1. Academic Press, 2014.
Jeannin, Pascale, Dorothée Duluc, and Yves Delneste. "IL-6 and leukemia-inhibitory factor are involved in the generation of tumor-associated macrophage: regulation by IFN-γ." Immunotherapy 3.4s (2011): 23-26.).
Kumari, Neeraj, et al. "Role of interleukin-6 in cancer progression and therapeutic resistance." Tumor Biology 37 (2016): 11553-11572.

* cited by examiner

Primary Examiner — Amy E Juedes
Assistant Examiner — Brian Hartnett
(74) Attorney, Agent, or Firm — Leonid Kisselev

(57) ABSTRACT

The present invention provides methods for inducing and expanding anti-tumor immunity leading to enhanced clinical and immunotherapeutic responses. The invention also provides novel compositions and methods for the treatment of cancer.

14 Claims, 23 Drawing Sheets

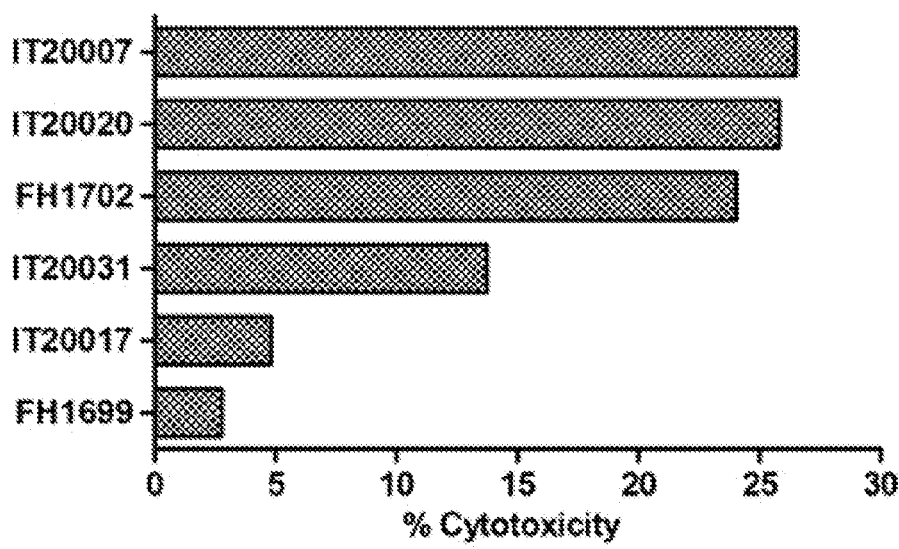
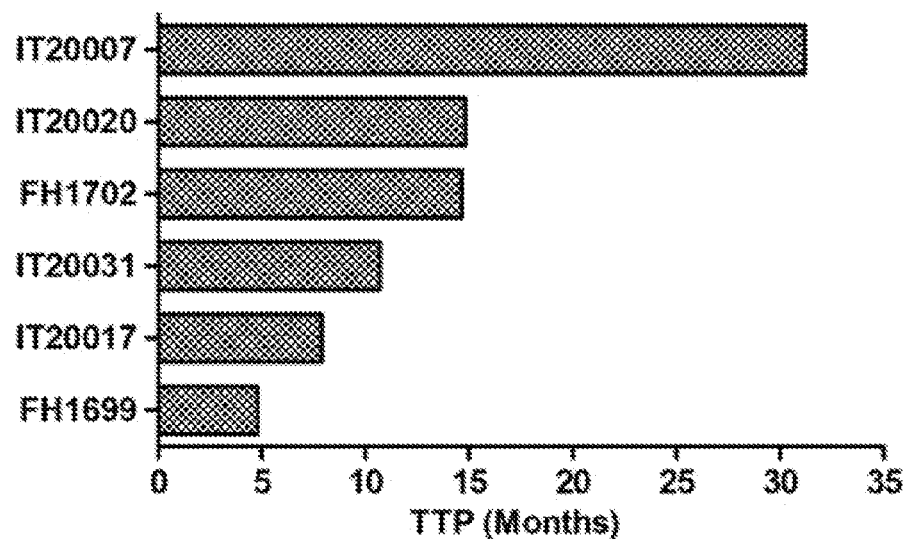
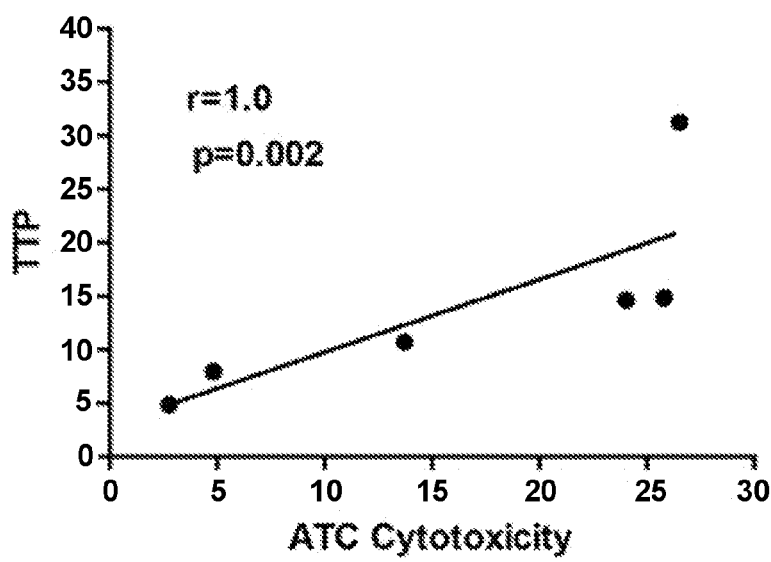
FIG. 1C

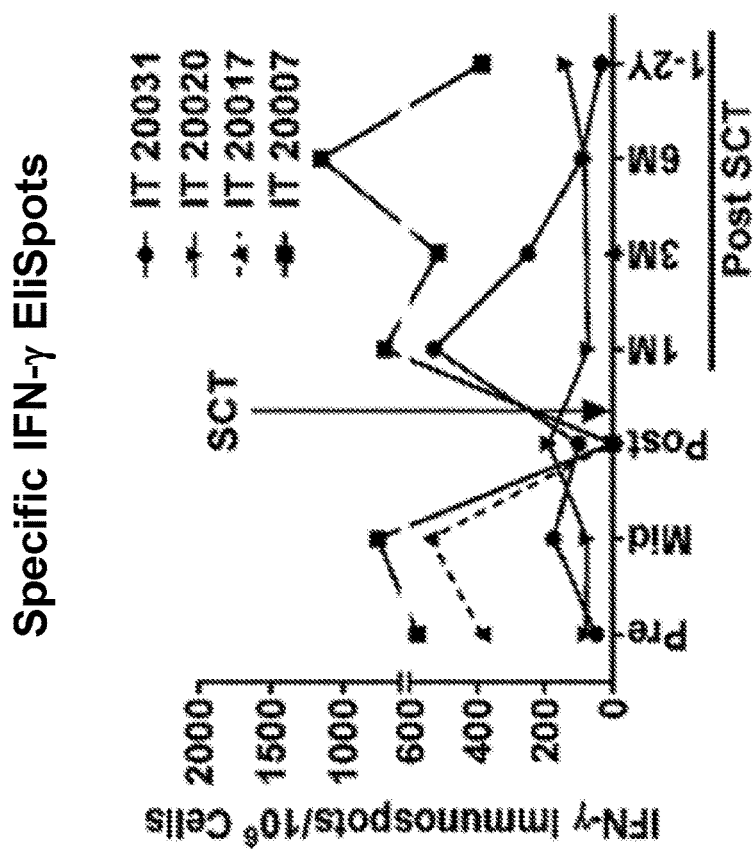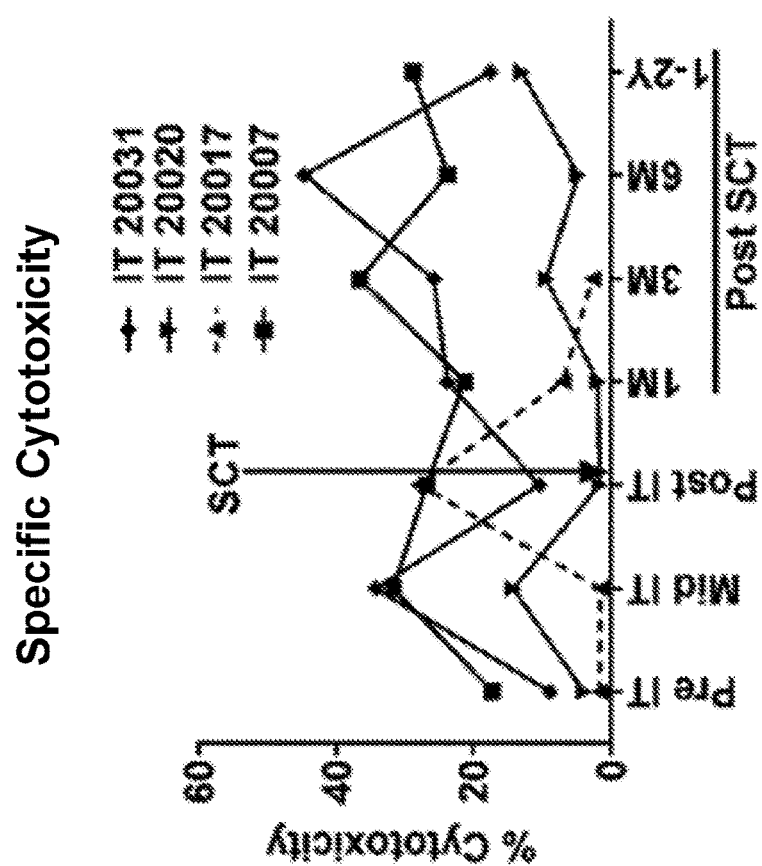
FIG. 2A

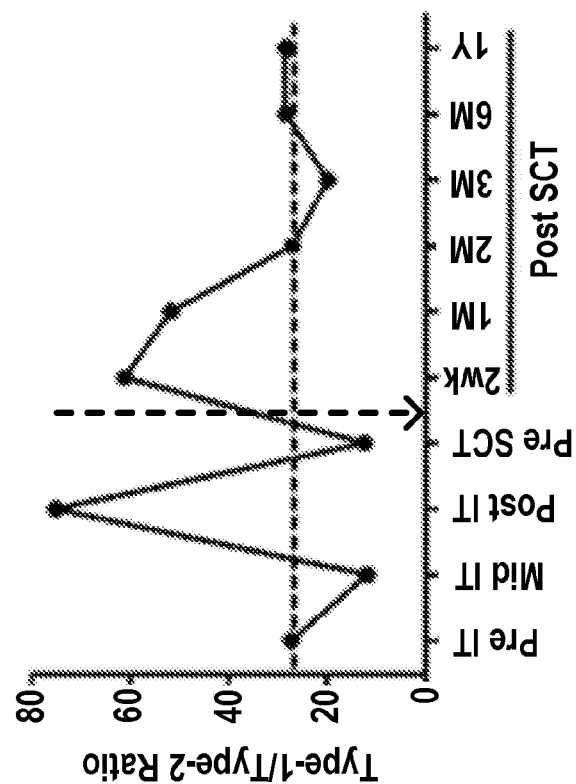
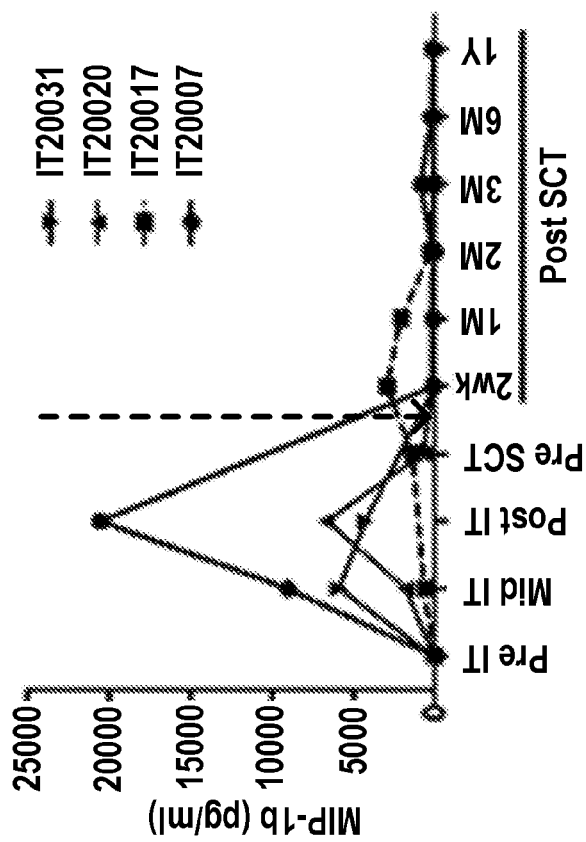
FIG. 3C cont'd

| Pa-tients | Age | HER2 (IHC) | Total HER2 BAT8 Infused (x 10$^6$) | Total ATC Infused after SCT (x 10$^6$) | Chemo-therapy | Engrafiment | | Clinical Features | | | | | |
|---|---|---|---|---|---|---|---|---|---|---|---|---|---|
| | | | | | | ANC ≥500 | ALC ≥500 | Enrollment (months) | | Post SCT (months) | | Status Pre IT | Status Post IT**/SCT |
| | | | | | | | | TTP | OS | TTP | OS | | |
| FH1699 | 58 | Neg | 160 | 43.52 | FAC, R-CHOP#, Tere, Ex, Ful, Cap | 11 | 13 | 4.8 | 18.9 | 2.7 | 16.8 | SD | PD |
| FH1702 | 31 | 3+ | 160 | 109.96 | Tere+Carbo+H, H, RT, T+Carbo, Nav+H, Abrax+H, Cap | 19 | 13 | 14.6 | 84.7 | 12.03 | 82.1 | SD | SD |
| IT20007 | 48 | Neg | 133 | 39.84 | AC, TC | 16 | 11 | 31.2 | 38 | 28.7 | 35.5 | SD | SD |
| IT20017 | 44 | Neg | 63.7 | 59.92 | ACTere, Cap, B, Carbo, Abrax, B, C, H, C | 16 | 8 | 7.9 | 9.9 | 3.9 | 5.9 | PD | PD |
| IT20020 | 47 | 3+ | 47.2 | 16.4 | ACT, H | 14 | 16 | 14.8 | 36.6 | 12.5 | 34.3 | PD | SD |
| IT20031 | 55 | Neg | 61.8 | 41.6 | ACTere, Abrax | 9 | 17 | 10.7 | 64.2 | 6.3 | 59.8 | SD | SD |
| IT20001* | 38 | Neg | 83.2 | NA* | ATC, Cap, B, Nav, G, Tipi+Abrax+G, Carbo, Carbo+Abrax | NA* | NA* | 2.03 | 9.2 | NA | NA | PD | PD* |
| IT20038* | 39 | Neg | 90.0 | NA* | ACT, B | NA* | NA* | 1.03 | 27.5 | NA | NA | PD | PD* |
| Median | 45.5 | | 86.6 | | | | | 11.2 | 32.05 | 12.03 | 34.9 | | |

FIG. 4

| Immune Response | Time Intervals | IT20007 | IT20017 | IT20020 | IT20031 | Total # (%) of + responses in boosted pts |
|---|---|---|---|---|---|---|
| CTL | PreIT | + | - | - | +/- | 1/4 (25) |
| | PreSCT | ++ | ++ | + | +++ | 4/4 (100) |
| | 3-6 M PostSCT | ++ | +/- | + | +++ | 3/4 (100) |
| IFNv | PreIT | ++ | ++ | +/- | +/- | 2/4 (50) |
| | PreSCT | ++ | ++ | + | + | 4/4 (100) |
| | 3-6 M PostSCT | +++ | - | + | ++ | 3/4 (75) |
| Serum Ab | PreIT | + | +/- | +/- | + | 2/4 (50) |
| | PreSCT | ++ | +/- | +/- | ++ | 2/4 (50) |
| | 3-6 M PostSCT | ++ | +/- | + | ++ | 3/4 (75) |
| In Vitro Ab Synthesis | PreIT | +/- | + | + | + | 3/4 (75) |
| | PreSCT | +++ | + | ++ | ++ | 4/4 (100) |
| | 3-6 M PostSCT | ++ | +/- | ++ | ++ | 3/4 (75) |
| Th1 | PreIT | + | + | + | + | 4/4 (100) |
| | PreSCT | +++ | +++ | +++ | +++ | 4/4 (100) |
| | 3-6 M PostSCT | +++ | +++ | ++ | ++ | 4/4 (100) |
| Th2 | PreIT | + | + | +/- | +/- | 2/4 (100) |
| | PreSCT | +++ | ++ | + | + | 4/4 (100) |
| | 3-6 M PostSCT | + | +++ | +/- | +/- | 2/4 (100) |
| Cell Dose (x $10^9$) | | 39.8 | 59.9 | 16.4 | 41.6 | |
| Survival (months) | | 35.5 | 5.9 | 34.2 | 57.1 | |

FIG. 5

| Unique Identifier | ATC for IT Phenotype | | | ATC for Boost Phenotype | | | Cytotoxicity | | | |
|---|---|---|---|---|---|---|---|---|---|---|
| | CD3+ | CD4+ | CD8+ | CD8+ | CD4+ | CD8+ | % Cytotoxicity by Pre Immune ATC and BAT | | % Cytotoxicity by Pre Immune ATC and BAT | % Cytotoxicity Immune ATC |
| | | | | | | | ATC | BATs | ATC | |
| FH1699 | NA | NA | NA | 67.9 | 32.7 | 38.8 | 10.1 | 7.8 | 2.76 | |
| FH1702 | NA | NA | NA | 34.8 | 25.4 | 8.5 | 3.8 | 12.0 | 24.0 | |
| IT 20006 | 95.6 | 64.6 | 31.0 | 78.3 | 65.3 | 12.6 | 4.0 | 26.1 | 8.1 | |
| IT 20007 | 97.22 | 66.7 | 30.5 | 93.0 | 72.9 | 31.0 | 7.8 | 65.0 | 26.5 | |
| IT 20017 | 98.49 | 76.1 | 22.4 | 82.7 | 58.4 | 26.7 | 0.9 | 49.2 | 4.8 | |
| IT 20020 | 97.53 | 74.3 | 23.2 | 76.6 | 47.4 | 31.1 | 3.6 | 44.2 | 25.8 | |
| IT 20031 | 92.42 | 64.7 | 27.7 | 85.2 | 78.6 | 13.7 | 0 | 44.2 | 13.7 | |
| IT 20038 | 95.07 | 57.15 | 37.44 | NA | NA | NA | 1.2 | 49.4 | NA | |

NA=Not available

FIG. 6

METHODS AND COMPOSITIONS FOR VACCINATING AND BOOSTING CANCER PATIENTS

CROSS-REFERENCES TO RELATED APPLICATIONS

This application claims priority to U.S. Provisional Application Ser. No. 62/497,879 entitled "METHODS AND COMPOSITIONS FOR VACCINATING AND BOOSTING CANCER PATIENTS," filed Dec. 7, 2016, the disclosure of which is hereby incorporated by reference in its entirety.

STATEMENT AS TO RIGHTS TO INVENTIONS MADE UNDER FEDERALLY SPONSORED RESEARCH AND DEVELOPMENT

This invention was made with Government support under N1H Grant P30CA22453. The Government has certain rights in this invention.

FIELD OF THE INVENTION

The present invention is directed to the field of immunology and oncology. The present invention provides for compositions and methods for T-cell based immunotherapies for malignancies or other disease characterized by abnormal cellular proliferation. In particular, the methods and compositions comprise autologous or allogeneic T cells capable of binding specific cancer antigens ultimately resulting in improved immunotherapeutic responses in cancer patients, and successful targeting of cancer cells in cancer patients. Additionally, the invention relates to a T cell population of cancer specific bispecific antibody armed activated T-cells, Chimeric Antigen Receptor T-cells (CAR-T), Tumor infiltrating lymphocytes (TILs), T-cell receptor engineered T cells (TCR transgenic) or bispecific antibody armed or unarmed T-Rapa cells generated against tumor antigens. The invention provides for treatments using autologous or allogeneic anti-cancer T cells, including cancer specific bispecific antibody armed activated T-cells, Chimeric Antigen Receptor T-cells (CAR-T), Tumor infiltrating lymphocytes (TILs), T-cell receptor engineered T cells (TCR transgenic) or bispecific antibody armed or unarmed T-Rapa cells, to treat patients diagnosed with malignancies such as pancreatic, breast, liver, prostate, ovarian, brain, lung, colon, and colorectal cancer, renal tumors, cancers of hematological origin, neuroblastomas, or other malignancies, and the generation of antigen-specific long-term memory T cells.

BACKGROUND OF THE INVENTION

Most malignancies can be treated by conventional surgery, chemotherapy, or radiotherapy if detected early. In contrast, it is nearly impossible for the immune system to reject bulky or metastatic disease. The challenge then is to identify antigen specific or non-specific systems that will improve clinical responses in the treatment of advanced cancers and hematologic malignancies.

The key issue in immunotherapy is to induce the immune system of a cancer patient to make a specific immune response to autologous tumors. A few tumor-specific antigens, such as HER-2/neu, malignant melanoma, and p53 are well-characterized and are known to induce in vitro and in vivo specific immune responses. Although adoptively transferred T cells can eliminate or reduce lethal tumor burdens in animals, adapting this principle in humans has been problematic.

Previous approaches include expansion of tumor infiltrating lymphocytes (TIL) that display cytotoxic activity directed at autologous tumor antigens using IL-2, and reinfusion of the TILs into patients with renal carcinoma (RCC) and metastatic melanoma (MM). TILs are CD3+ cells that display activated natural killer cell (ANK) activity but are more effective killers than ANK on a per cell basis. Trials using TILs and high dose IL-2 in patients with advanced RCC, MM, and other advanced tumors have obtained clinical responses with most reports ranging between 15-20% (Topalian et al., *J. Clin. Oncol.* 6:839-853 (1988); Rosenberg et al., *N. Engl. J. Med.* 319:1676-1680 (1988); Rosenberg et al., *N. Engi. J. IMed.* 323:570-578 (1990); and Goedegebuure et al., *J. Clin. Oncol.* 13:1939-1949 (1995)).

However, TIL therapeutic approaches have major drawbacks. One limitation of TIL therapy are the toxicities related to high dose IL-2 infusions which restrict the use of IL-2 in patients who have poor performance status (Peace and Cheever, *J. Exp. Med.* 169:161-173 (1989); Lotze et al., *J. Immunol.* 135:2865-2875 (1985); and Higuchi et al., *Blood* 77:2561-2568 (1991)).

Another drawback is that the rate of positive clinical responses from the combination of TIL and high dose IL-2 is still unacceptably low. Unfortunately, the anti-tumor activity exhibited by TIL has not been a consistent observation in larger clinical series (see, Rosenberg et al., *Science* 233:1318-1321 (1986)).

In an alternative therapeutic approach, infusions of HER2 bispecific antibody armed activated T cells (BATs) in women with metastatic breast cancer (MBC) were observed to induce specific anti-breast cancer immunity and increased IL-12 and $Th_1$ cytokines (Lum et al. Targeted T-cell Therapy in Stage IV Breast Cancer: A Phase 1 Clinical Trial. *Clin Cancer Res* 21(10): 2305-2314 (2015)). These BAT infusions were found to be safe (no high dose toxicities) and induced anti-BrCa cytotoxic lymphocytes. However, as with TIL therapy, treatment of the cancer patient with IL-2 is routinely applied to maintain a T cell response after BAT infusion.

In another Phase I study, infusions of unprimed and unarmed activated T cells (ATCs) in women with MBC after autologous stem cell transplantation (SCT), reported that 50% of the patients were stable and 75% alive, whereas 15% of those who received SCT alone were stable and only 50% alive. In this study, the patient receiving unprimed, unarmed ATCs is also treated with IL-2 or GM-CSF to maintain a robust T cell response in the cancer patient. In view of the known toxicities from IL-2 and GM-CSF treatments, there is still a need in the art to provide for improved immunotherapeutic approaches that include strategies that address the above and other issues.

Here, we demonstrate for the first time that a cancer-specific T-cell vaccine cell population can induce tumor-specific cellular, humoral, and innate immunity that can be transferred with infusions of immune ATCs and stem cell transplantation in breast cancer patients. Specifically, the inventors have determined that cellular and humoral anti-breast cancer immunity induced by infusions of BATs can be transferred after high dose chemotherapy (HDC) and autologous SCT by immune ATCs obtained after BATs infusions. Furthermore, the above immunity can be invoked without the patient receiving IL-2 or GM-CSF treatments.

BRIEF SUMMARY OF THE INVENTION

In one aspect, the present invention provides a method of improving the immunotherapeutic response of a cancer patient vaccinated with a cancer specific T-cell, the method comprising (i) vaccinating a cancer patient with a cancer specific T-cell vaccine cell population in vivo in an amount sufficient to prime immune T-cells of the cancer patient: (ii) collecting the immune T-cells from the peripheral blood of the cancer patient; (iii) culturing the collected T-cells ex vivo; and (iv) reinfusing the cultured T-cells into the cancer patient in vivo, wherein the cancer patient is not treated with IL-2 and GM-CSF. In some embodiments, the cancer patient is not treated with IL-2. In another embodiment, the cancer patient is not treated with GM-CSF. In one embodiment, the cancer patient is not treated with IL-2 during, after, or before the reinfusion of the cultured T cells. In some embodiments, the cancer patient is not treated with GM-CSF during, after, or before the reinfusion of the cultured T cells.

In some embodiments, the cancer specific T cell vaccine cell population further includes professional antigen presenting cells, such as dendritic cells. In another embodiment, the cancer specific T-cell vaccine cell population is an autologous cancer specific T-cell vaccine cell population. In yet another embodiment, the cancer specific T-cell vaccine cell population is an allogeneic cancer specific T-cell vaccine cell population.

In a preferred embodiment, the cancer specific T-cell vaccine cell population is bispecific antibody armed activated T-cells (BATs), Chimeric Antigen Receptor T-cells (CAR-T), Tumor infiltrating lymphocytes (TILs), T-cell receptor engineered T cells (TCR transgenic) or bispecific antibody armed or unarmed T-Rapa cells.

In some embodiments, the reinfusing occurs between 1-15 times for a total of up to 160 Billion cultured T-cells total. In some embodiments, the method is carried out according to the schema provided in FIG. 1.

In some embodiments, the method further comprises suppressing the T-cell population in the cancer patient prior to reinfusing. In one embodiment, the T cell population in the cancer patient prior to reinfusing is less than 1000 T cells per $mm^3$. In a preferred embodiment, the T cell population in the cancer patient prior to reinfusing is less than 400 T-cells per $mm^3$. In some embodiments, suppressing the T cell population in the cancer patient is due to myeloablation. In another embodiment, suppressing the T cell population in the cancer patient is due to chemotherapy (e.g., high dose or mild dose chemotherapeutic) treatment.

In some embodiments, the cancer specific T-cell vaccine cell population used to vaccinate the cancer patient is between 0.06-160 Billion T-cells.

In some embodiments, the cancer patient has a cancer that is a solid tumor or a cancer of hematologic origin. In some embodiments, the cancer of hematologic origin is multiple myeloma, non-Hodgkin's lymphoma, Hodgkin's lymphoma or leukemia. In another embodiment, the solid tumor is pancreatic, breast, liver, ovarian, brain, neuroblastoma, prostate, lung or colon/colorectal cancer.

In a second aspect, the present invention provides a cell population for reinfusing into a cancer patient comprising between 0.4-80 Billion T cells cultured from the cancer patient vaccinated with the cancer specific T-cell vaccine cell population.

In one embodiment, the cancer specific T-cell vaccine cell population is an autologous cancer specific T-cell vaccine cell population. In another embodiment, the cancer specific T-cell vaccine cell population is an allogeneic cancer specific T-cell vaccine cell population.

In a preferred embodiment, the cancer specific T-cell vaccine cell population are bispecific antibody armed activated T-cells (BATs) or bispecific antibody armed or unarmed T-Rapa cells.

In some embodiments, the cancer specific T-cell vaccine cell population is bispecific antibody activated T-cells wherein the bispecific antibody recognizes a tumor or viral antigen. In one embodiment, the cancer specific T-cell vaccine cell population is bispecific antibody activated T-cells wherein the bispecific antibody recognizes Human Epidermal Growth Factor Receptor 2 (HER2), Epidermal Growth Factor Receptor (EGFR), GD2, CD19, CD20, CD22, CD123, SLAMF7, CD38, SAS1B, wnt1, PMEL17, or Carcinoembryonic antigen (CEA).

In another embodiment, the cancer specific T-cell vaccine cell population is bispecific antibody armed activated T-cells activated with an anti-CD3 antibody or anti-CD3 and anti-CD28 antibodies, and cultured in IL-2.

In yet another embodiment, the cancer specific T-cell vaccine cell population is CAR-T cells co-activated with anti-CD3 and anti-CD28 antibodies.

In some embodiments, the cell population for reinfusing into the cancer patient further comprises cultured or uncultured B cells.

In a third aspect, the present invention provides a cancer specific T-cell vaccine cell population for use in a method of immunotherapy of a cancer patient where the patient is not treated with IL-2 and GM-CSF, the method comprising (i) vaccinating the cancer patient with the cancer specific T-cell vaccine cell population in an amount sufficient to prime immune T-cells of the cancer patient; (ii) collecting the immune T-cells from the peripheral blood of the cancer patient; (iii) culturing the collected T-cells ex vivo; and, (iv) reinfusing the cultured T-cells into the cancer patient. In some embodiments, the cancer specific T-cell vaccine cell population is an autologous cancer specific T-cell vaccine cell population. In another embodiment, the cancer specific T-cell vaccine cell population is an allogeneic cancer specific T-cell vaccine cell population. In some embodiments, the cancer specific T-cell vaccine cell population further comprises dendritic cells.

In one embodiment, the cancer specific T-cell vaccine cell population is bispecific antibody armed activated T-cells (BATs), Chimeric Antigen Receptor T-cells (CAR-T), Tumor infiltrating lymphocytes (TILs), T-cell receptor engineered T cells (TCR transgenic) or bispecific antibody armed or unarmed T-Rapa cells.

In some embodiments, the reinfusing of the cultured T cells occurs between 1-15 times for a total of up to 160 Billion cultured T-cells total. In some embodiments, the method is carried out according to the schema provided in FIG. 1.

In some embodiments, the method further comprises suppressing the T-cell population in the cancer patient prior to the reinfusing. In one embodiment, the T cell population in the cancer patient prior to reinfusing is less than 1000 T cells per $mm^3$. In a preferred embodiment, the T cell population in the cancer patient prior to reinfusing is less than 400 T-cells per $mm^3$. In some embodiments, suppressing the T cell population in the cancer patient is due to myeloablation. In another embodiment, suppressing the T cell population in the cancer patient is due to chemotherapy (e.g., high dose or mild dose chemotherapeutic) treatment.

In some embodiments, the cancer specific T-cell vaccine cell population used to vaccinate the cancer patient is between 0.06-160 Billion T-cells.

In some embodiments, the cancer patient has a cancer that is a solid tumor or a cancer of hematologic origin. In some embodiments, the cancer of hematologic origin is multiple myeloma, non-Hodgkin's lymphoma, Hodgkin's lymphoma or leukemia. In another embodiment, the solid tumor is pancreatic, breast, liver, ovarian, brain, neuroblastoma, prostate, lung or colon/colorectal cancer.

Definitions

Before the present invention is described, it is to be understood that the invention is not limited to particular cell lines, tumor antigens, excipients or method steps described, and as such may vary. For example, a step may be omitted, repeated, or occurs at a stage that is different from the exemplary embodiments provided herein. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a T-cell" includes a plurality of such T-cells and reference to "the antibodies" includes reference to one or more antibodies and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

As used herein, the terms "subject" or "patient" are used interchangeably and in either the singular or plural form, refer to any human or nonhuman animal. The term "nonhuman animal" includes all vertebrates, e.g., mammals and non-mammals, such as nonhuman primates, pigs, sheep, dogs, cats, cows, chickens, amphibians, reptiles, etc. In preferred instances, the term refers to a mammalian human subject to be treated or assessed. In some cases, the methods of the invention find use in experimental animals, in veterinary applications, and in the development of animal models for disease, including, but not limited to, rodents including mice, rats, and hamsters; and primates.

As used herein, the terms "cancer" or "tumor" are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass (e.g., by procedures such as CAT scan, MR imaging, X-ray, ultrasound or palpation, and/or which is detectable because of the expression of one or more cancer-specific antigens in a sample obtainable from a patient).

As used herein, the term "solid tumor" refers to tumors that are not part of the lymphatic system. A solid tumor is an abnormal mass of tissue and can benign or malignant. Generally, there are three types of solid tumors, sarcomas, carcinomas and lymphomas. Carcinomas, derived from epithelial types of cells, are the most commonly diagnosed form of cancers and originate in the skin, lungs, breasts, pancreas, liver, prostate, kidneys, and in other organs and glands (e.g., pituitary and thyroid). Carcinomas often grow in an infiltrative manner and continue to persist through infiltration or invasion of adjacent structures. Carcinomas typically spread to the lymph nodes and bones, secondarily. Sarcomas are derived from mesodermal (mesenchymal cells) and tend to arise primarily from bone as opposed to spreading to the bone. Sarcomas grow as "ball-like" masses with a pseudocapsular layer tending to move adjacent structures (e.g., veins, arteries and nerves) away. This local growth often allows for complete resection during surgery. In contrast, lymphomas are a group of blood cancers that develop from lymphocytes (e.g., B and T cells). For the purpose of this application, lymphomas are considered a cancer of hematologic origin (see below).

As used herein, the term "cancer of hematologic origin" refers to tumors that are derived from hematopoietic cells. These tumors affect the blood, bone marrow, lymph and lymphatic system. Hematological malignancies can arise from either myeloid or lymphoid cell lines. The myeloid cell line produces granulocytes, erythrocytes, thrombocytes, macrophages and mast cells; the lymphoid cell line produces B, T, NK and plasma cells. As such, lymphomas (i.e., Hodgkin's lymphomas and Non-Hodgkin's lymphomas), lymphocytic leukemias, and myeloma are from the lymphoid line, while acute and chronic myelogenous leukemia, myelodysplastic syndromes and myeloproliferative diseases are myeloid in origin. For the purpose of this application, lymphomas are considered a cancer of hematologic origin. Various methods known in the art to detect a cancer of hematologic origin including a complete blood count and blood film using light microscopy. Alternatively, a biopsy from a lymph node may be undertaken. Additionally, a bone marrow biopsy can also be performed and examined microscopically to determine the nature of the malignancy. Other methods for detecting malignant cells from cancers of hematologic origin include cytogenetics, for example fluorescent in situ hybridization, comparative genomic hybridization (CGH), single nucleotide polymorphism (SNP) arrays (e.g., for acute myelogenous leukemia (AML) and chronic myelogenous leukemia (CML) or immunphenotyping (e.g., for lymphomas, myelomas, chronic lymphocytic leukemia (CLL)).

The term "leukemia" refers broadly to progressive, malignant diseases of the blood-forming organs. Leukemia is typically characterized by a distorted proliferation and development of leukocytes and their precursors in the blood and bone marrow but can also refer to malignant diseases of other blood cells such as erythroleukemia, which affects immature red blood cells. Leukemia is generally clinically classified on the basis of (1) the duration and character of the disease-acute or chronic; (2) the type of cell involved-myeloid (myelogenous), lymphoid (lymphogenous) or monocytic, and (3) the increase or non-increase in the number of abnormal cells in the blood-leukemic or aleukemic (subleukemic). Leukemia includes, for example, acute leukemia, chronic leukemia, adult leukemia, pediatric/child leukemia, lymphocytic leukemia, myeloid leukemia, acute lymphocytic leukemia (ALL), acute nonlymphocytic leukemia, chronic lymphocytic leukemia, acute granulocytic leukemia, chronic granulocytic leukemia, acute promyelocytic leukemia, chronic myelogenous leukemia (CML), T-cell leukemia, B-cell leukemia, adult T-cell leukemia, pediatric T-cell ALL, pediatric B-cell ALL, aleukemic leukemia, aleukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukaemic leukemia, and undifferentiated cell leukemia.

As used herein, the term "immunotherapeutic response" refers to a detectable (e.g., chemical, biological, cellular or physical) response in a subject (e.g., cancer patient) or a cell obtained from the subject that results in the induction, enhancement or suppression of an immune response in the subject or cell that is associated with a reduction in cancer load or tumor burden. Preferably, the immune response is associated with a reduction in cancer load or tumor burden in the subject.

In some embodiments, the immunotherapeutic response comprises detecting or measuring a change in the production or expression of one or more cytokines. In a preferred embodiment, the cytokines comprise serum cytokines. In some embodiments, the cytokines include T helper 1 and T helper 2 cytokines. In one embodiment, the one or more serum cytokines are selected from IL-2, TNF-α, IFN-γ, IL-4, IL-6, IL-10, IL-12, MIP-1β, IP-10, and MIG.

In another embodiment, the immunotherapeutic response can comprise detecting or measuring a change in T cell phenotyping. In some embodiments, the Vβ repertoire pattern may be determined for one, all, or a portion of memory T cells of interest. In another embodiment, the change in T cell phenotyping can include determining which, if any, memory T cell clones have the same or different Vβ repertoires. In yet another embodiment, the immunotherapeutic response can comprise detecting or measuring the expression of interferon-gamma (IFN-γ) by the memory T cell clones.

In another embodiment, the immunotherapeutic response can comprise detecting or measuring the production of antibody responses in serum after exposure to a T cell vaccine cell population (e.g., BATs, TILs, etc.), optionally after stem cell transplantation. Accordingly, the immunotherapeutic response can include detecting, measuring, or monitoring the production of antibody synthesis of anti-tumor antibodies (e.g., anti-BrCa antibodies).

In another embodiment, the immunotherapeutic response can include detecting or measuring cytotoxicity of a T cell vaccine cell population against a cancer cell line (e.g., breast cancer cell line SK-BR-3). In some embodiments, cytotoxicity can be determined by comparing the response of the cancer cell line against the T cell vaccine cell population as compared to the response of the cancer cell line against non-stimulated (NS) T cells.

In some embodiments, an immunotherapeutic response can include the induction or enhancement of one or more immune responses such that it results in the treatment of cancer in the subject. In some embodiments, the immunotherapeutic response can include complete curing or remission of the cancer in the subject. In another embodiment, the immunotherapeutic response can comprise a positive correlation of one or more biological markers (e.g., serum cytokines) with respect to the cancer in the subject as compared to the one or more biological markers in an untreated cancer patient or the corresponding biological marker found in a patient (or cells obtained from a patient) receiving standard of care treatment for the cancer.

A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

As used herein, "immune cells" refers to any cell of the immune system that may be assayed, including, but not limited to, B lymphocytes (B cells), T lymphocytes (T cells), natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells (PMBC), tumor-infiltrating (TIL) cells, gene modified immune cells including hybridomas, drug modified immune cells, and derivatives, precursors or progenitors of the above cell types.

As used herein, the term "population" refers to cells having the same or different identifying characteristics, such as the expression of the same antigen or CD molecule. In some embodiments, the population can comprise a T cell population expressing the same CD marker. In another embodiment, the population can comprise a T cell population recognizing the same tumor or viral antigen. The term "lineage" refers to all of the stages of the development of a cell type, from the earliest precursor cell to a completely mature cell (i.e. a specialized cell such as a mature T or mature B cell). In some aspects, the term T-cell population refers to a plurality of T-cells having the same identifying characteristics, such as T cells having the same bispecific antibody (i.e., a first arm directed to the same tumor antigen (e.g., CD19) and a second arm directed to the same stimulatory molecule (e.g., CD3).

As used herein, "memory T cells" refers to a subset of T cells that have previously encountered and responded to their cognate antigen (e.g., a tumor antigen). At a second or later encounter with the cognate antigen the memory T cells can expand into large numbers of effector T cells to produce a rapid immune response to the antigen. Effector T cells is a broad classification of T cells that includes various T cell types that actively respond to a stimulus (e.g., co-stimulation). The classification of T cells includes T helper (Th$_1$ and Th$_2$), Cytotoxic T cells (CTLs) and regulatory T cell types (T$_{reg}$). Systemic memory T cells are characterized according to the cell surface expression of certain antigens. Typically these cells are positive for CD4+ or CD8+, often expressing CD45RO and lacking expression of CD45RA (found on naïve T cells) and integrin α4β7. Systemic memory T cells are further characterized by expression of CCR4. Verification of the identity of any cells discussed herein may be performed by any methods known in the art, including antibody staining and analysis by fluorescence detection, ELISA, reverse transcriptase PCR, transcriptional amplification and hybridization to nucleic acid microarrays, etc.

As used herein, the terms "vaccinate" and "vaccinating" are used interchangeably and in either the singular or plural form, refer to methods by which a subject is treated with a vaccine to produce immunity against an antigen of interest. Specifically, the term refers to an antigen specific cell population (e.g., a cancer specific T cell population, such as but not limited to, bispecific antibody armed activated T cells and bispecific antibody armed or unarmed T-Rapa cells) that are administered to a subject to produce immunity against an antigen found on or within a cancer cell. Preferably, the cancer patient who is administered with the antigen specific cell population (e.g., cancer specific T cell vaccine) elicits an immunotherapeutic response against the subject's cancer. Vaccination requires administration of the vaccine to the cancer patient to stimulate the cancer patient's immune system, specifically the cancer patient's T- and B-cells to develop immunity to the tumor cells. As will be apparent to one of ordinary skill in the art, a vaccine can be administered by various means, including by injection (intravenous (IV), subcutaneous (SubQ), intramuscular (IM), intradermal), puncture, transdermal, intranasal, or via delivery to a mucosal surface to negate the need for injection. In a preferred embodiment, a cancer specific T-cell vaccine of the present invention is administered via intravenous or subcutaneous methods.

As used herein, a "cancer specific T-cell" refers to a T-cell that has been stimulated with antigenic material (e.g., an endogenous tumor antigen) corresponding to a specific tumor antigen (e.g., HER2, EGFR, CEA, wnt1, PMEL17, etc.) or, as described below, a T cell that has been modified to redirect a T cell against a tumor independent of its endogenous T cell receptor (e.g., bispecific antibody armed activated T cells, CAR-T cells, TCR transgenic T cells, or bispecific antibody armed or unarmed T-Rapa cells. The cancer specific T cell recognizes the specific tumor antigen and can elicit an immunotherapeutic response as a result of exposure to a tumor cell expressing the specific tumor antigen. As such, a cancer specific T cell vaccine refers to a population of cancer-specific T cells sharing the same characteristic with respect to targeting the same tumor antigen (e.g., HER2) or multiple tumor antigens. As is discussed below, cancer specific T cells can be prepared from T cells isolated from a cancer subject, where the isolated T cells are modified (e.g., coated with bispecific antibodies, CAR-T cells, TCR transgenic T cells, etc.) to recognize the tumor antigen of interest (e.g., HER2).

In a normal immune response, a "primed T-cell" or "immune T-cell" refers to a process by which naïve T cells are exposed to antigenic material (e.g., a tumor antigen). T cells are distinguishable from B cells and natural killer cells by the presence of a T-cell receptor (TCR) on the T cell surface. All T cells originate from hematopoietic stem cells in the bone marrow. Hematopoietic progenitors from hematopoietic stem cells populate the thymus and expand by cell division to generate a large population of thymocytes. Ultimately, single-positive CD4+CD8− or CD4−CD8+ thymocytes are released from the thymus into peripheral blood. Exposure of a TCR on a naïve T cell to an antigen initiates the process of T-cell activation (Chen L, Flies D B. Molecular mechanisms of T cell co-stimulation and co-inhibition. *Nat Rev Immunol.* 2013; 13(4):227-242). Generally, antigen presentation by an antigen presenting cell (APC) (e.g., professional APCs such as dendritic cells and non-professional APCs such as B cells) is not sufficient to induce an immune response without a second signal (i.e., CD28) that allows T cell activation to proceed. Naïve T cells (i.e., immature T cells) upon activation, mature into T helper cells or cytotoxic T lymphocytes (CTLs). Specifically, CD4+ cells can mature into mature T helper cells (Th$_1$ and Th$_2$), while immature CD8+ cells can mature into CTLs. As such, activated T cells expand and differentiate into 'memory' and 'effector' T cells. Accordingly, T cell priming and activation provides the immune system with a population of activated T cells that recognize (e.g., have a 'memory') against previously encountered antigens.

In some embodiments of the invention, immune T cells are prepared by vaccinating a cancer subject with a cancer specific T cell vaccine. By administering the cancer specific T cell vaccine to the subject, the subject's immune system is able to endogenously promote the proliferation and growth of additional immune T cells that maintain antigen specificity to recognize the cancer antigen in the subject. In some embodiments, the number of cancer specific T cells required to vaccinate the cancer subject is between 0.06 and 160 Billion cancer specific T cells. After vaccination, the subject can be monitored for the production of immune T cells having the same identifying characteristic (i.e., the ability to recognize cancer specific antigens or epitopes). In one embodiment, a peripheral blood draw can be made after the first round of vaccination and optionally, before the last round of vaccination to assess the ability of T cells in the cancer subject to recognize cancer antigens. Assessing whether the immune T cells in the cancer subject can recognize the cancer antigen of interest can be performed by any methods known in the art, including isolating one or more immuneT cells from the subject to test for cancer cell specific responses such as cytokine production, proliferation or cytotoxicity. In another embodiment, flow cytometry may be used to determine if the isolated T cells from the subject after one or more rounds of vaccination are immune T cells, e.g, using tetramer or pentamer binding.

In some embodiments, immune T cells may refer to the isolation of naïve T cells from a subject and exposure of the T cells ex vivo to a specific tumor antigen to create a population of T cells that are 'primed' to recognize the tumor antigen in vivo. The immune T cells can then be stimulated ex vivo either by using soluble anti-CD3 antibody, or co-activation by using anti-CD3 and anti-CD28 monoclonal antibodies, either soluble or immobilized on a solid support. Anti-CD3 upregulates the expression of interleukin 2 (IL-2) receptors and facilitates expansion in IL-2 containing culture/media. A preferred solid support are plastics or any surface upon which antibodies can be immobilized, or beads, such as, for example, Dynal beads.

Once activated, the immune T cells can be optionally armed with a bispecific antibody (BiAb). The location and movement through the patient's body of the activated T cells (including BiAbs) can be monitored by using a labeled antibody that binds to a desired molecule on the surface of the activated T cell or directed to a portion of the bispecific antibody, such as for example, the $F_C$ region. Monitoring of the activated T cells is achieved, for example, using flow cytometry. The activated T cells can also be labeled with agents which are detectable by any imaging techniques known in the art.

Preferably, immune T cells of the invention are T cells that are cancer specific T cells that have been activated as a result of exposure to a T cell vaccine population. Immune (e.g., cancer specific) T cells can be removed from the cancer patient via leukapheresis methods known in the art and clonally expanded and cultured ex vivo before reinfusion of the cultured T cells into the subject.

In some instances, cancer specific T cell vaccine population of the invention (e.g., a bispecific antibody armed activated T cell) allows for the treatment of diseases other than tumors as the bispecific antibody can be prepared or designed to be specific for any desired epitope (e.g., a viral epitope to treat viral infections or a bacterial epitope to treat infectious bacterial infections).

As used herein, "arming" or "armed" with respect to a T cell population is binding by the T cell specific portion of the bispecific antibody to the T cell antigen of interest, that is to the T cell receptor (TCR) complex antigens such as CD3. The second portion of the bispecific antibody is specific for the cancer antigen of choice (e.g., a tumor antigen such as HER2 or EGFR), thereby targeting the bispecific antibody armed activated T cell to the specific antigen (e.g., a tumor antigen).

As used herein, the terms "T-cell Adoptive Transfer" or "Adoptive T cell transfer", are used interchangeably and refer to ex vivo cultivation of extracted T cells from a subject for later transfusion into the same (autologous) or different recipient (allogeneic). The objective of the process is conceptually the same as that of successful T cell immunization, namely the stimulation and expansion of potent and antigen-specific T cell immunity. As such, experimental results for adoptive T cell therapy of tumors are known (see, Restifo et al., 2012). The extracted T cells can include Tumor infiltrating lymphocytes (TILs) (Dudley, 2008) or bulk lymphocytes (Rapport et al., 2005) from peripheral blood. The extracted T cells may already target a specific antigen (e.g., tumor antigen or infectious organism antigen). In other instances, the extracted T cells can be genetically engineered or otherwise modified to do so (e.g., using bispecific monoclonal antibodies to target a tumor antigen, discussed herein), and the modified T cells are expanded and activated ex vivo with cytokines, such as IL-2, IL-7 and/or IL-15, before transfusion back into the subject (Gattinoni et al., *Nat. Rev. Immunol.*, 6(5):383-923 (2006). The extracted T cells are typically obtained via leukapheresis of peripheral blood mononuclear cells (PMBC) followed by bulk ex vivo expansion and reinfusion along with exogenous IL-2 (Rappaport, 2005). Optionally, before re-infusion into the subject, the subject may be pre-treated with a single low dose of chemotherapy such as, doxorubicin (Dox) or paclitaxel (Tax) (Hsu et al., *Oncotarget*, 6(42):44134-50 (2015). The doses of Dox and Tax used in Hsu's study were defined as "low-dose" compared with clinical dosages based on the formula proposed by Reagan-Shaw et al., *FASEB J*, 22(3): 659-61 (2008). According to the formula, 1-4 mg/kg Dox and 5-10 mg/kg Tax in Hsu's study were equivalent to 3-12 mg/m$^2$ Dox and 15-30 mg/m$^2$ Tax in the clinic. Data from recent clinical trials using engineered antigen-specific T cells show the potential of adoptive T cell therapy to effectively target cancer, with objective clinical activity in a number of cases (Brentjens et al., 2013; Johnson et al., 2009; Kochenderfer et al., 2012) including complete and long-lasting durable clinical responses observed in patients with late-stage, chemotherapy resistant leukemia's (Grupp et al., 2013; Kalos et al., 2011).

The term "engineered antigen specific T-cells" or "TCR transgenic" refers to molecular biology techniques that transfer antigen specific T cell receptor a and 3 chains composed of antibody binding domains fused to T cell signaling domains. The resulting T cells acquire the engineered, tumor specific specificity while retaining their initial specificity. The primary source for isolating tumor specific αβTCR has been tumor specific T cell clones from cancer patients or healthy (non-cancerous) volunteers. The strategies involved for in vitro stimulation include peptides or whole antigens. Alternatively, rational high-throughput genetic mutagenesis approaches have been applied to enhance the affinity of tumor-antigen specific αβ TCR (Chervin et al., 2008; Li et al., 2005), and such efforts have resulted in the ability to molecularly engineer αβ TCR with substantially higher affinities for target antigens (Li et al., 2005). Alternative strategies to improve αβ TCR avidity by engineering TCR chains have also been pursued (Kuball et al., 2009).

The term "Chimeric Antigen Receptors" or "CAR-T" refers to a molecular biology technique to engineer T cells by the introduction of chimeric antigen receptors (CARs), which are synthetic polypeptides that contain 3 distinct modules: an extracellular target binding module, a transmembrane module which anchors the molecule into the cell membrane, and an intracellular signaling module that transmits activation signals. The target binding module is usually generated using scFv determinants isolated from antibodies, linked in a single chain through linker polypeptide sequences. Transmembrane modules are most commonly derived from molecules involved in T cell function such as CD3ζ and CD28. The intracellular module often consists of the zeta chain of the TCR complex responsible for transmitting TCR engagement-mediated activation signals to cells. Recently developed CARs incorporate additional domains associated with T cell functions in an effort to augment zeta signaling in a physiologically relevant manner. As CARs recognize intact cell surface proteins, targeting of target cells is neither MHC-restricted nor dependent on processing and effective presentation of target epitopes and CAR-based approaches are insensitive to tumor escape mechanisms related to HLA down-modulation and altered processing escape mechanisms, an issue that is common in human carcinoma (Vitale et al., 2005).

As used herein, the term "T-Rapa" refers to T cells isolated from a subject (e.g., a cancer patient) that are incubated ex vivo in the presence of rapamycin (an inhibitor of mTOR). The incubated T cells are subjected to co-stimulation for example with various anti-CD antibodies (e.g., anti-CD3 and anti-CD28), the rapamycin incubated T cells overcome the effect of rapamycin and instead of dying, survive in cell culture with little or no proliferation. An exemplary method for preparing T-Rapa cells is set forth in Fowler et al., *Blood,* 121:15, 2864-2874 (2013), which is incorporated herein by reference in its entirety.

As used herein, a "target cell" is any cell comprising an antigen that the T cell binds to. The target cell is not limited to tumor antigens but can include for example, viral antigens, infectious disease organism antigens and the like.

As used herein, the term "Peripheral blood" refers to cellular components of blood including, but not limited to, red blood cells (erythrocytes), white blood cells (leucocytes such as granulocytes (i.e., neutrophils, eosinophils, basophils), monocytes and lymphocytes) and platelets (thrombocytes) suspended in blood plasma found within the circulating blood of a subject. Peripheral blood does not include cellular blood components sequestered to the lymphatic system, spleen, liver or bone marrow. Accordingly, a peripheral blood draw (e.g., from a subject) will include all of the cellular components of blood (e.g., dendritic cells, macrophages, T cells, B cells, granulocytes, hematopoietic stem cells, etc., and sub-types thereof) unless otherwise stated.

The term "therapeutically effective amount" as used herein, refers to the level or amount of one or more agents needed to treat a condition (e.g., viral infection or cancer) in a subject, or reduce or prevent further injury or damage to tissues, cells or the subject as a whole, optionally without causing significant negative or adverse side effects.

BRIEF DESCRIPTION OF THE DRAWINGS

FIG. 1C shows bar graphs of cytotoxicity (top panel) mediated by expanded immune ATC of 6 patients against SK-BR-3 and their corresponding Time To Progression (TTP) (middle panel), there was a significant correlation (p=0.002, bottom panel) between product cytotoxicity and TTP, suggesting that higher cytotoxicity, may improve progression free survival.

FIG. 2A, left panel shows the specific cytotoxicity by PBMC (n=8; 6 were evaluable) directed at SK-BR-3 and at pre IT, mid IT (infusion #4 or #5), and post IT at 25:1 E/T ratio and gradual increase in cytotoxicity post SCT indicating transfer and reconstitution of T cell responses. FIG. 2A, right panel shows T cell IFN-γ EliSpots (n=4) directed at SK-BR-3 at pre IT, mid IT, post IT and multiple time points post SCT. FIG. 2A cont'd, left panel shows anti-BrCa antibody levels in serum. FIG. 2A cont'd, right panel shows in vitro anti-SKBR3 breast cancer cell antibody synthesis that gradually increases post-SCT indicating transfer and reconstitution of B cell responses.

FIG. 2B, Upper panel shows the IFN-γ EliSpot responses by overnight stimulation of PBMCs with 9-mer peptide pre-loaded HLA-A2-pentamers from three patients at pre IT, post IT and post SCT time points. FIG. 2B, lower panel shows the percentages of pentamer/CD8 double positive T cells stained with HLA-A2-pentamers-R-PE and anti-CD8-FITC antibodies by flow cytometry. The healthy PBMCs stimulated with SEB (200 ng/ml) was used as a positive control. FIG. 2B cont'd, panels show the persistent and transient expansion of tumor specific Vβ repertoire after multiple infusions of BATs and transfer of breast cancer specific T cells after SCT. IFN-γ secreting CD4+ and CD8+ T cell clones in immune ATC upon stimulation (S) with breast cancer cell line SK-BR-3 or in non-stimulated (NS) T cells.

FIG. 2C, Upper panel shows the pooled peptide specific antibody titers by ELISA (1:100 dilution) in 4 patients at pre IT, post IT and multiple time points post SCT. Serum antibody steadily increase up to 6M post SCT indicating transfer and reconstitution of B cell responses. FIG. 2C, lower panel shows specific serum antibody responses against indicated individual peptides by semi quantitative dot-blot assay at 1:100 dilution in two patients (IT20007 and IT 20020) at various time points. FIG. 2C, cont'd panel shows the quantitation of anti-CEA specific antibody levels in two patients (IT20007 and IT 20020) by ELISA.

FIG. 4 shows patient demographics, HER2 status, cell doses, engraftment, OS and disease status prior to IT and post SCT. A: adriamycin; Abrax: Abraxane; B: bevacizumab (Avastin); C: cyclophosphamide (Cytoxan); Cap: capecitabine (Xeloda); Carbo: carboplatin; Ex: exemestane (Aromasin); Ful:fulvestrant (Faslodex); FAC: 5-fluorouracil, A, and C; H: Herceptin (trastuzumab): RT: radiation therapy; T: paclitaxel; Tere: taxotere; R-CHOP: Rituximab, cyclophosphamide, doxorubicin, vincrtistine, and prednisolone; Nav: navelbine; Tipi: Tipifarnib. **:Clinical status after IT or SCT; SD: stable disease; PD: progressive disease. *Patients did not receive SCT.

FIG. 5 shows exemplary immune responses at Pre IT, Pre SCT and 3-6 months Post SCT.

FIG. 6. shows phenotype and cytotoxicity of harvested products.

DETAILED DESCRIPTION

Figure 1A:
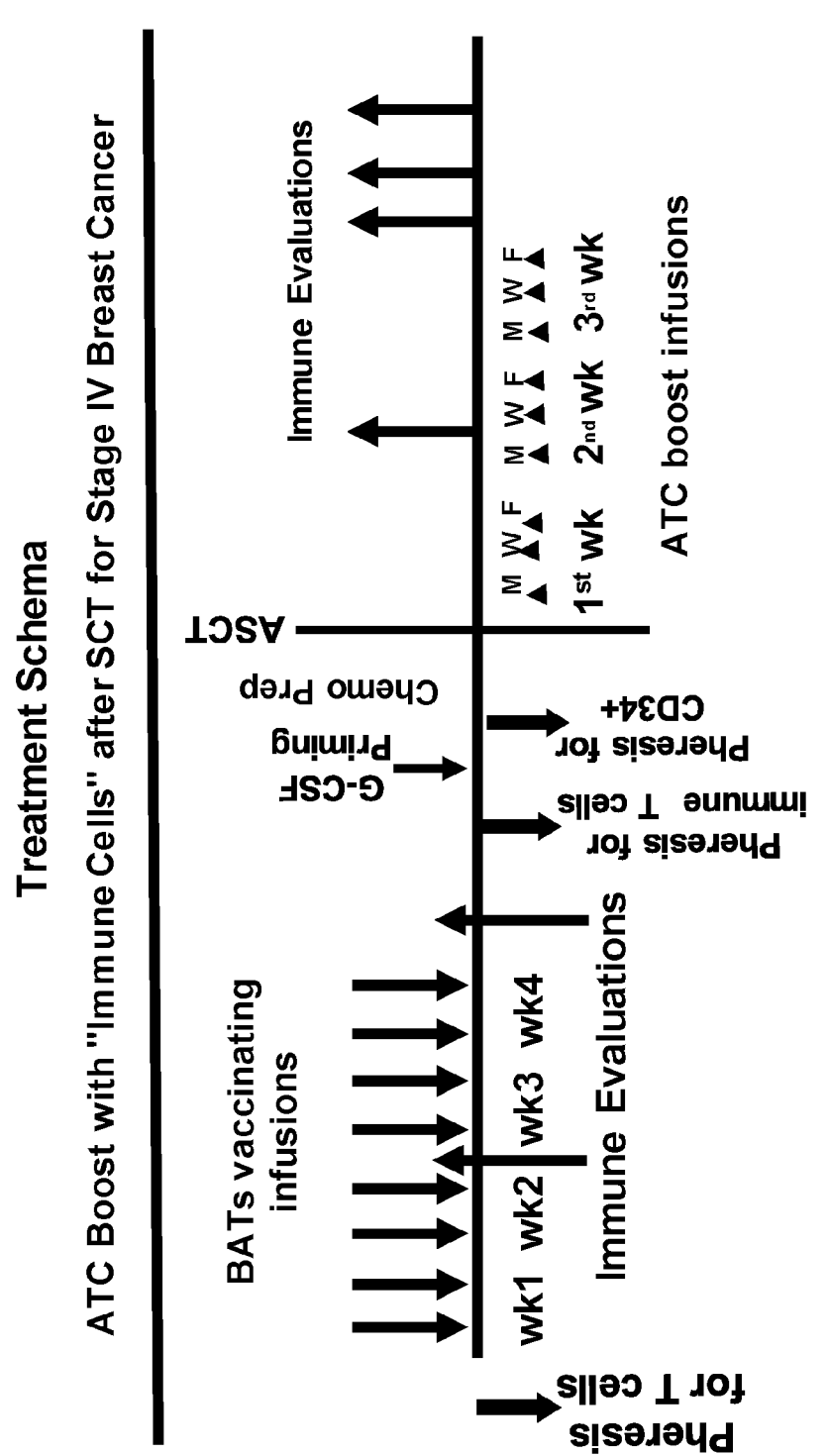
FIG. 1A shows an exemplary treatment schema shows leukapheresis to obtain T cells for expansion and immunization with BATs. BATs were administered twice weekly for four consecutive weeks. A second leukapheresis was done to obtain immune T cells prior to G-CSF priming for collecting stem cells. PBMC were activated with OKT3 and expanded in IL-2 (100 IU/ml) to generate ATC after 12-14 days of culture. After a third pheresis to collect G-CSF primed CD34+ cells, patients received cyclophosphamide, thiotepa, and carboplatin (CTC) as the preparative regimen for chemosensitive disease and ifosfamide, carboplatin and etoposide (ICE) for resistant disease followed by autologous SCT. Immune ATC were infused day +4 after SCT thrice (n=2) or twice (n=4) a week for total 8-15 infusions and immune testing was performed at indicated time points after ATC infusions.

This invention provides methods and composition for the treatment of malignancies associate with cancer.

In one aspect, the present invention provides a method of improving the immunotherapeutic response of a cancer patient vaccinated with a cancer specific T-cell, the method comprising (i) vaccinating a cancer patient with a cancer specific T-cell vaccine cell population in vivo in an amount sufficient to prime immune T-cells of the cancer patient; (ii) collecting the immnue T-cells from the peripheral blood of the cancer patient; (iii) culturing the collected T-cells ex vivo; and (iv) reinfusing the cultured T-cells into the cancer patient in vivo, wherein the cancer patient is not treated with IL-2 and GM-CSF.

In some embodiments, the cancer patient is not treated with IL-2. In another embodiment, the cancer patient is not treated with GM-CSF. In one embodiment, the cancer patient is not treated with IL-2 during, after, or before the reinfusion of the cultured T cells. In some embodiments, the cancer patient is not treated with GM-CSF during, after, or before the reinfusion of the cultured T cells.

In some embodiments, the cancer specific T cell vaccine cell population further includes professional antigen presenting cells. In one embodiment, the cancer specific T cell vaccine cell population further includes dendritic cells.

In one embodiment, the cancer specific T-cell vaccine cell population is an autologous cancer specific T-cell vaccine cell population. In another embodiment, the cancer specific T-cell vaccine cell population is an allogeneic cancer specific T-cell vaccine cell population.

In a preferred embodiment, the cancer specific T-cell vaccine cell population is bispecific antibody armed activated T-cells (BATs), Chimeric Antigen Receptor T-cells (CAR-T), Tumor infiltrating lymphocytes (TILs), T-cell receptor engineered T cells (TCR transgenic) or bispecific antibody armed or unarmed T-Rapa cells.

In some embodiments, the reinfusing occurs between 1-15 times for a total of up to 160 Billion cultured T-cells total. In one embodiment, the reinfusing occurs between 5 and 15 times for a total of up to 160 Billion cells.

In some embodiments, the method further comprises suppressing the T-cell population in the cancer patient prior to reinfusing. In one embodiment, the T cell population in the cancer patient prior to reinfusing is less than 1000 T cells per mm$^3$. In a preferred embodiment, the T cell population in the cancer patient prior to reinfusing is less than 400 T-cells per mm$^3$. In some embodiments, the T cell population in the cancer patient prior to reinfusion is between 50 and 400 T cells per mm$^3$. In some embodiments, suppressing the T cell population in the cancer patient is due to Myeloablation. In another embodiment, suppressing the T cell population in the cancer patient is due to high dose or mild dose chemotherapeutic treatment.

In some embodiments, the cancer specific T-cell vaccine cell population used to vaccinate the cancer patient is between 0.06-160 Billion T-cells.

In one embodiment, the cancer patient has a cancer that is a solid tumor or a cancer of hematologic origin. In some embodiments, the cancer of hematologic origin is multiple myeloma, non-Hodgkin's lymphoma, Hodgkin's lymphoma or leukemia. In another embodiment, the solid tumor is pancreatic, breast, liver, ovarian, brain, neuroblastoma, prostate, lung or colonicolorectal cancer.

I. Immunotherapy & T Cell Adoptive Transfer

Immunotherapy is the treatment of disease by inducing, enhancing, or suppressing an immune response. Immunotherapies designed to elicit or amplify an immune response are classified as activation immunotherapies. In recent years, immunotherapy has become particularly interesting to researchers, clinicians and pharmaceutical companies, given its potential to treat various forms of cancer.

Immune cells, such as lymphocytes (B and T cells), macrophages, dendritic cells, natural killer cells (NK Cell), cytotoxic T lymphocytes (CTL), work together to defend against cancer by targeting cancer antigens expressed on the surface of cancer cells. As such, cancer immunotherapy attempts to stimulate the immune system to detect and destroy cancer cells. A variety of strategies are in use or are undergoing research and in some cases significant increases in survival and disease free periods have been reported.

Adoptive cell transfer (ACT) is the transfer of cells into a patient. The cells may have originated from the patient or from another individual. The cells are most commonly derived from the immune system, with the goal of improving immune functionality and characteristics. In autologous cancer immunotherapy, T cells are extracted from a cancer patient, modified, cultured ex vivo and returned to the same patient. Comparatively, allogeneic therapies involve cells isolated and expanded from a donor patient who is a separate individual to whom is receiving the expanded cells. The donor cells can be from fully HLA-matched related or unrelated donors, partially matched related or unrelated donors, or fully mismatched unrelated donors. Donor cells may be derived from peripheral blood, bone marrow or umbilical cord blood.

In either approach, extracted T cells are clonally expanded, for example using Interleukin-2 (IL-2), a growth and differentiation factor of T cells, and an anti-CD3 antibody. The expanded T cells are transferred into a patient along with further administrations of IL-2 and/or GM-CSF to further boost the T cell populations anti-cancer activity. However, both of these cytokines when administered to cancer patients before, during, or after T cell adoptive transfer have serious and substantial side effects. For example, the major toxicities of recombinant IL-2 are fluid gain and capillary leak syndrome leading to respiratory distress and hypotension often requiring vasopressor support and ICU monitoring. Other side effects include fever, chills, malaise, diarrhea, increased creatinine, mental status changes, cardiac arrhythmias, and rashes. Adverse effects accompanying high dose, intravenous IL-2 therapy were observed to be severe, with cardiovascular, pulmonary, haematological, hepatic, neurological, endocrine, renal and/or dermatological complications frequently requiring doses to be withheld (Whittington & Faulds, Interleukin-2. A review of its pharmacological properties and therapeutic use in patients with cancer, Drugs, 46 (3): 446-514 (1993)). In the U.S., patients receiving IL-2 are typically treated for 5 consecutive days, three times a day. A lower dose regime to ameliorate the impact of IL-2 toxicity involves subcutaneous injections of IL-2 on an out-patient basis or alternatively given on an inpatient basis over 1-3 days, similar to, and often including the delivery of chemotherapy.

Additionally, recombinant Granulocyte Macrophage-Colony Stimulating Forming (GM-CSF) administered to cancer patients (typically via intravenous or subcutaneous routes) to stimulate blood cell production and growth is commonly associated with diarrhea, vomiting, internal bleeding, pain, chills, fever, fatigue, infection, weight loss, itching, and rashes. Other less frequent by serious side effects include cardiac arrhythmias, swelling of the arms/legs, kidney damage, capillary leak syndrome leading to respiratory distress and hypotension. In some instances, individuals develop significant side effects resulting from the formation of blood clots that can lead to pulmonary embolus or stroke.

Furthermore, single or multiple administrations of IL-2 and/or GM-CSF to cancer patients cost substantial amounts of money and precious clinical resources. It is estimated by the inventors, that current treatment regimens comprising T cell adoptive transfer that include administration of recombinant IL-2 and GM-CSF to cancer patients equates to about $18,000 per patient. This cost increases if the patient receives more than the standard number of IL-2 and/or GM-CSF treatments. Accordingly, new methods to reduce costs for cancer patients, health care insurers, and reduce the burden on precious clinician resources are needed.

Generally, before reinfusion of expanded T cells into a cancer patient, lymphodepletion of the cancer patient is required to eliminate regulatory T cells ($T_{Kg}$) as well as unmodified, endogenous lymphocytes that compete with the transferred T cells for cytokines. Lymphodepletion can be achieved through various means, including myeloablation via radiotherapy (e.g., total body irradiation) or chemotherapy (e.g., High Dose Chemotherapy or Mild Dose Chemotherapy).

The reinfused T cells multiply in vivo and persist in the patient's peripheral blood. One study observed, 75% of all $CD8^+$ T cells at 6-12 months after infusion were the direct result of reinfused T cells (Dudley et al., Cancer regression and autoimmunity in patients after clonal repopulation with antitumor lymphocytes, *Science,* 298:6694:850-4 (2002)).

II. Suitable Forms of Cancer

Solids Tumors

Solid tumors are tumors that are not part of the lymphatic system. A solid tumor is an abnormal mass of tissue and can be benign or malignant Generally, there are three types of solid tumors, sarcomas, carcinomas and lymphomas. For the purpose of this application, lymphomas are considered a cancer of hematologic origin (see below). Solids tumors are frequently detected through cytological analysis of biopsy or tissue slices using microscopy or antibody binding assays.

In one embodiment, the compositions and methods disclosed herein are suitable for the treatment of solid tumors. The solid tumor can be located in a subject having cancer or cells obtained from, or derived from, a solid tumor obtained from a subject having the cancer. In some embodiments, the compositions and methods disclosed herein are suitable for the treatment of a solid tumor in a living, human subject.

Cancers of Hematologic Origin

Cancers of hematologic origin are tumors derived from hematopoietic cells. These tumors affect the blood, bone marrow, lymph and lymphatic system. Hematological malignancies can arise from either myeloid or lymphoid cell lines. The myeloid cell line produces granulocytes, erythrocytes, thrombocytes, macrophages and mast cells; the lymphoid cell line produces B, T, NK and plasma cells. Various methods are known in the art to detect cancers of hematologic origin including a complete blood count and blood film using light microscopy. Alternatively, a biopsy from a lymph node may be undertaken. Additionally, a bone marrow biopsy can also be performed and examined microscopically to determine the nature of the malignancy. Other methods for detecting malignant cells from cancers of hematologic origin include cytogenetics, for example fluorescent in situ hybridization, comparative genomic hybridization (CGH), single nucleotide polymorphism (SNP) arrays (e.g., for acute myelogenous leukemia (AML) and chronic myelogenous leukemia (CML) or immunphenotyping (e.g., for lymphomas, myelomas, chronic lymphocytic leukemia (CLL)).

In one embodiment, the compositions and methods disclosed herein are suitable for the treatment of cancers of hematologic origin. The cancer of hematologic origin can be located in a subject having the cancer or cells obtained from, or derived from, a cancer of hematologic origin obtained from the subject having the cancer. In some embodiments, the compositions and methods disclosed herein are suitable for the treatment of a cancer of hematologic origin in a living, human subject.

Tumor Antigens

Tumor antigens are often divided into two categories: shared tumor antigens; and unique tumor antigens. Shared antigens are expressed by two or more tumors. Unique tumor are expressed by an individual tumor. Most currently classified tumor antigens are endogenously synthesized, and as such are presented on major histocompatibility complex (MHC) class I molecules to CD8+ T cells. Detailed explanations of tumor antigens can be found, for example in Abbas, Lichtman, and Pillai (Cellular and Molecular Immunology, $8^{th}$ Edition, (2014)), and Olsen et al., (*Cancer Immunol Immunother.,* 66:731 (2017), which retroactively catalogues more than 1000 tumour peptides from 368 proteins and provides a freely available database documenting human tumor antigens), the disclosures of which are incorporated herein by reference in their entireties (see, http://cvc.dfci.harvard.edu/tadb/).

In one embodiment, T cell vaccines prepared according to the instant application preferentially comprise an epitope from a unique tumor (i.e., possess a unique tumor antigen). Unique tumor antigens decrease the risk of autoimmunity, but because the immune response is directed to a single epitope, tumors can evade destruction through antigen loss variance. A process called "epitope spreading" or "provoked immunity" can mitigate this effect. Epitope spreading is the expansion or diversification of an immune response against a broader or different range of epitopes relative to initial or preexisting epitope specificities. This effect can be detected by a number of different assays, such as changes in the relative levels of Vb family members of T cells, reactivity of T cells to different antigens (proliferation, cytokine expression, cytotoxicity, tetramer binding), and/or changes in the levels and specificity of antibodies to different antigens or epitopes. Accordingly, in one aspect of the invention, the methods and related compositions provide a method of epitope spreading.

As described herein, cancer T cell vaccine cell populations disclosed herein can comprise bispecific antibody activated T cells, where the bispecific antibody recognizes one or more tumor antigens. While not being an exhaustive list, rather a non-limiting embodiment, the bispecific antibody can recognize any one or more of the following tumor antigens: HER family, Survivin, BING4, BAGE1, TRAG-3, TRP-2, GAGE family, MAGE family, SAGE, SSX2, MART-2, AFP, ANXA2, hTERT, CCND1, CSF1, GD2, CD19, CD20, CD22, CD38, CD123, SLAMF7, SASIB, wnt1, PMEL17, CEA, PMSA, and EpCAM.

The terms "CD19" and "CD19 antigen" are used interchangeably herein, and include any variants, isoforms and species homologs of human CD19 which are naturally expressed by cells or are expressed on cells transfected with the CD19 gene. In some embodiments, binding of an antibody (particularly bispecific antibodies of the invention) to the CD19 antigen inhibits and/or blocks CD19 from binding to its ligand and concomitantly, the resultant cellular function thereof.

The terms "CD20" and "CD20 antigen" are used interchangeably herein, and include any variants, isoforms and species homologs of human CD20 which are naturally expressed by cells or are expressed on cells transfected with the CD20 gene. In some embodiments, binding of an antibody (e.g., rituximab, obinutuzumab, tiuxetan or particularly, bispecific antibodies of the invention) to the CD20 antigen inhibits and/or blocks CD20 from binding to its ligand and concomitantly, the resultant cellular function thereof.

The terms "CD22" and "CD22 antigen" are used interchangeably herein, and include any variants, isoforms and species homologs of human CD22 which are naturally expressed by cells or are expressed on cells transfected with the CD22 gene. In some embodiments, binding of an antibody (e.g., moxetumomab pasudotox or particularly, bispecific antibodies of the invention) to the CD22 antigen inhibits and/or blocks CD22 from binding to its ligand and concomitantly, the resultant cellular function thereof The terms "CD38" and "CD38 antigen" are used interchangeably herein, and include any variants, isoforms and species homologs of human CD38 which are naturally expressed by cells or are expressed on cells transfected with the CD38 gene. Synonyms of CD38, as recognized in the art, include cyclic ADP ribose hydrolase. In some embodiments, binding of an antibody (e.g., Daratumumab or particularly bispecific antibodies of the invention) to the CD38 antigen inhibits and/or blocks CD38 from binding to its ligand and concomitantly, the resultant cellular function thereof.

The terms "CD123" and "CD123 antigen" are used interchangeably herein, and include any variants, isoforms and species homologs of human CD123 which are naturally expressed by cells or are expressed on cells transfected with the CD123 gene. Synonyms of CD123, as recognized in the art, include interleukin-3 receptor. In some embodiments, binding of an antibody (e.g., SGN-CD123A or particularly bispecific antibodies of the invention) to the CD123 antigen inhibits and/or blocks CD123 from binding to its ligand and concomitantly, the resultant cellular function thereof.

The terms "CD319" and "CD319 antigen" are used interchangeably herein, and include any variants, isoforms and species homologs of human CD319 which are naturally expressed by cells or are expressed on cells transfected with the CD319 gene. Synonyms of CD319, as recognized in the art, include SLAMF7. In some embodiments, binding of an antibody (e.g., Elotuzumab or particularly bispecific antibodies of the invention) to the CD319 antigen inhibits and/or blocks CD319 from binding to its ligand and concomitantly, the resultant cellular function thereof.

HER Family

The receptor tyrosine kinase family known as the HER family consists of four members: EGFR (also known as ErbB1/HER1), HER2, HER3, and HER4. HER1-4 play an important role in controlling and regulating cell growth, differentiation, migration, and death. EGFR is a tumor-associated antigen overexpressed on the cell surface of various malignant tumors, such as NSCLC, glioblastoma, pancreatic cancer, HNSCC, renal cancer, and colorectal cancer (CRC) (Ciardiello and Tortora, A novel approach in the treatment of cancer: targeting the epidermal growth factor receptor. *Clin Cancer Res.* 7(10):2958-70 (2001)). HER3 has been identified as an important molecule in the interaction with ligand as well as PI3K signaling pathway (Schoeberl et al. Therapeutically targeting ErbB3: a key node in ligand-induced activation of the ErbB receptor-PI3K axis. *Sci Signal.*, 2(77):31 (2009)). A recent study demonstrated that HER4 is a favorable prognostic marker for overall survival (OS) in patients with breast cancer (Wang et al., Human epidermal growth factor receptor 4 (HER4) is a favorable prognostic marker of breast cancer: a systematic review and meta-analysis. *Oncotarget.* 7(47):76693-703 (2016)). As such, the HER family members are attractive targets for immunotherapy, especially in the application of bispecific antibodies.

Carcinoembryonic Antigen (CEA)

CEA is a 180-200 KDa glycoprotein that belongs to the CEA-related cell adhesion (CEACAM) superfamily. CEA is expressed at low levels in various normal tissues including colon, stomach, esophagus, tongue, cervix, and prostate (Behr et al., Factors influencing the pharmacokinetics, dosimetry, and diagnostic accuracy of radioimmunodetection and radioimmunotherapy of carcinoembryonic antigen-expressing tumors. *Cancer Res.* 56(8): 1805-16 (1996)). CEA-overexpressing malignant cancers included colorectal, gastric, lung, breast, pancreatic, and other cancers (Behr et al. Variables influencing tumor dosimetry in radioimmunotherapy of CEA-expressing cancers with anti-CEA and antimucin monoclonal antibodies. *J Nucl Med.* 38(3):409-18 (1997)).

In cancer tissues, CEA is overexpressed and is cleaved from the surface of cancer cells by phospholipase, which results in an increase of serum CEA (Yamamoto et al. Distributions in CEA doubling time differ in patients with recurrent colorectal carcinomas. *Hepato-Gastroenterology.* 51(55):147-51 (2004)). Blood levels of CEA are currently used as a diagnostic and prognostic marker, as well as a monitoring index in patients after treatment (Rother M. Carcinoembryonic antigen monitoring for early detection of asymptomatic incurable metastatic colorectal cancer. *J Clin Oncol.* 25(10): 1293-4 (2007)). It has also been demonstrated that serum levels of soluble CEA do not affect tumor suppression by CEA/CD3 BsAbs (Lutterbuese et al. Potent control of tumor growth by CEA/CD3-bispecific single-chain antibody constructs that are not competitively inhibited by soluble CEA. *J Immunother.*, 32(4):341-52 (2009) and Osada et al. Metastatic colorectal cancer cells from patients previously treated with chemotherapy are sensitive to T-cell killing mediated by CEA/CD3-bispecific T-cell-engaging BiTE antibody. *Br J Cancer.* 102(1):124-33 (2010)). CEA, is a well characterized tumor-associated antigen (TAA), and is therefore a target for the immunotherapy, including antibody-based treatments of CEA-positive solid tumors (Khare et al. Specifically targeted killing of carcinoembryonic antigen (CEA)-expressing cells by a retroviral vector displaying single-chain variable fragmented antibody to CEA and carrying the gene for inducible nitric oxide synthase. *Cancer Res.* 61(1):370-5 (2001)).

Prostate-Specific Membrane Antigen (PSMA)

PSMA is a membrane bound protein that is selectively expressed on the surface of prostate cancer cells as well as in the neovasculature of most solid tumors (Cardillo et al., Tumor target prostate specific membrane antigen (PSMA) and its regulation in prostate cancer. *J Cell Biochem.* 93(4): 641-43 (2004)). PSMA is expressed across all stages of prostate cancer, and the expression level is inversely correlated with androgen levels (Id). PSMA plays an essential role in the progression of prostate cancer through MAPK-ERK1/2 and PI3K-AKT pathway and can be used as the target for imaging agents to detect metastatic tumor sites (Kiess et al. Prostate-specific membrane antigen as a target for cancer imaging and therapy. *J Nucl Med Mol Imaging.* 59(3):241-68 (2015)). Accordingly, PSMA is an attractive target for the immunotherapy of prostate cancers.

EpCAM

EpCAM (CD326, 17-IA) is a 39-40 KDa transmembrane glycoprotein that functions as adhesion molecule (Balzar et al., *Mol Cell Biol,* 21:7, 2570-80, (2001)). EpCAM is expressed by majority of normal epithelial tissues including lung, colon, pancreas, bile ducts, breast, as well as embryonic stem cells (Gonzalez et al., EpCAM is involved in maintenance of the murine embryonic stem cell phenotype. *Stem Cells.* 27(8): 1782-91 (2009). Similar to CD44, CD133, and CD166, EpCAM is considered a cancer stem cell (CSC) marker (Munz et al., The emerging role of EpCAM in cancer and stem cell signaling. *Cancer Res.* 69(14):5627-9 (2009)). The expression of EpCAM is correlated with epithelial cell proliferation, differentiation, and migration (Baeuerle and Gires. EpCAM (CD326) finding its role in cancer. *Br J Cancer.* 96(3):417-23 (2007)) and as such is a target for immunotherapy.

Sperm Acrosomal SLLP1 Binding Protein (SASIB)

SASIB (GenBank ID NM_001002036.3) is a ~46 KDa metalloproteinase. SAS1B is expressed on the surface of oocytes and in normal ovaries. It has also been observed in both endometrioid and malignant mixed Mullerian tumors (MMMT) of the uterus. The SASIB metalloproteinase has been proposed as a cancer-oocyte tumor surface neoantigen for development of targeted immunotherapeutics with limited on-target/off tumor effects predicted to be restricted to the population of growing oocytes (see, Pires et al., *Oncotarget,* 6:30, 30194-30211 (2015).

It will be readily apparent that the list of tumor antigens provided in this section is not to be construed as limiting, but rather represents an exemplary list of tumor antigens that can be used in the present compositions and methods. Specifically, any tumor antigen or epitope derived from a tumor antigen can be used in the methods and compositions disclosed herein.

III. Production of Cancer Specific T Cells

Bispecific Antibody Armed Activated T Cells (BATs)

In one aspect, the invention generally relates to the production of BATs. BATs can be used for the treatment of solid tumors and cancers of hematological origin (discussed herein and see U.S. Pat. No. 7,763,243). Bispecific-armed activated T cells (ATCs) that have been coated with bispecific antibodies (BiAb), with potential antineoplastic and immunomodulating activities. In vitro, T cells are activated through exposure to the anti-CD3 murine monoclonal antibody OKT3 and interleukin 2 for approximately 14 days and then armed with an anti-CD3×anti-tumor bispecific antibody (e.g., HER2). Upon administration to a subject, the bispecific armed activated T cells attach to CD3-expressing T cells and tumor antigen (HER2) expressing tumor cells, selectively cross-link the T cells and tumor cells; resulting in CTL perforin-mediated tumor cell cytolysis, the recruitment and activation of B cells and cytotoxic T lymphocytes (CTLs), and the secretion of anti-tumor cytokines and chemokines.

Various method for the preparation of BATs are known in the art and are incorporated herein, including the methods set forth in U.S. Pat. No. 7,763,243, and Yu et al., J. Hematol Oncol, 10:155, 2017, the disclosures of each are incorporated herein by reference in their entireties. It will also be readily apparent that other methods for preparing BATs are contemplated by the present invention, such as magnetic bispecific cell engager (MagBICE) which combines BATs with biodegradable iron nanoparticles, which allows for magnetic targeting and imaging (see, Tang et al., *Expert Opin. Biol. Ther.* 15(9):1251-55 (2015).

The interaction of activated T cells and tumor cells mediated by bispecific antibodies, initiates the killing process of tumor cells, including activation of CD3 signaling, formation of immunologic synapses, activation and proliferation of T cells, secretion of cytokines and cytotoxic granules, and lysis of tumor cells (Haas et al., *Immunobiology* 214(6):441-53, (2009)). The activated T cells lyse cancer cells predominantly through perforin and granzyme B and secrete various cytokines such as IFN-γ, TNF, IL-2, IL-6, and IL-10 (shown herein in Example 1 and Hoffman et al., *Intl. J. Cancer,* 115(1):98-104, (2005)).

In one aspect, the bispecific antibody can be directed to any antigen expressed on the cell surface of a solid tumor or cancer of hematologic origin. Commonly expressed antigens on solid tumors, include but are not limited to, EpCAM, EGFR, HER family (e.g., HER2 and HER3), CEA and PSMA. Commonly expressed antigens on cancers of hematological origin, include but are not limited to, EGFR, HER2, GD2, CD19, CD20, CD22, CD123, SLAMF7, CD38, SASB1, wnt1, PMEL17 and CEA.

In one embodiment, the present invention provides a composition comprising anti-CD3 activated T cells (ATCs) or anti-CD3 and anti-CD28 co-activated T-cells (COATCs) armed with chemically heteroconjugated anti-CD3 (OKT3)×anti-Her2/Neu (9184) or anti-CD3 (OKT3)×anti-Her2/Neu (Herceptin) bispecific monoclonal antibodies (BATs) (See, U.S. Pat. No. 7,763,243 and Han et al., *Intl. J. Oncology,* 45:2446-54 (2014)). ATC/COATCS are prepared by ex vivo stimulation of the T cells with soluble OKT3/OKT3 and anti-CD28 conjugated beads, and cultured in IL-2. In the above cited disclosures, the BATs were directed to the treatment of breast and colorectal cancers.

In another embodiment, the present invention provides a composition comprising anti-CD3 activated T cells (ATCs) or anti-CD3 and anti-CD28 co-activated T-cells (COATCs) armed with anti-CD3 (OKT3)×anti-CD20 bispecific monoclonal antibody (CD20Bi). Upon administration, anti-CD3× anti-CD20 bispecific antibody-armed activated T cells attach to CD3-expressing T cells and CD20-expressing tumor cells, selectively cross-linking T cells and tumor cells.

In another embodiment, the present invention provides a composition comprising anti-CD3 activated T cells (ATCs) or anti-CD3 and anti-CD28 co-activated T-cells (COATCs) armed with anti-CD3 (OKT3)×anti-GD2 bispecific monoclonal antibody (GD2Bi-aATC) (See, NIH clinical trial identifier: NCT02173093). Upon administration, anti-CD3× anti-GD2 bispecific antibody-armed activated T cells attach to CD3-expressing T cells and GD2-expressing tumor cells, selectively cross-linking T cells and tumor cells. Accordingly, such BATs can be directed to the treatment of neuroblastoma and osteosarcoma.

In another embodiment, the present invention provides a composition comprising anti-CD3 activated T cells (ATCs) or anti-CD3 and anti-CD28 co-activated T-cells (COATCs) armed with anti-CD3 (OKT3)×anti-EGFR bispecific monoclonal antibody (See, NIH clinical trial identifier: NCT02620865). Upon administration, anti-CD3×anti-EGFR bispecific antibody-armed activated T cells attach to CD3-expressing T cells and EGFR-expressing tumor cells, selectively cross-linking T cells and tumor cells. Accordingly, such BATs can be directed to the treatment of pancreatic cancer.

In yet another embodiment, the present invention provides a composition comprising anti-CD3 activated T cells (ATCs) or anti-CD3 and anti-CD28 co-activated T-cells (COATCs) armed with anti-CD3 (OKT3)×anti-CD19 bispecific monoclonal antibody. Upon administration, anti-CD3×anti-CD19 bispecific antibody-armed activated T cells attach to CD3-expressing T cells and CD19-expressing tumor cells, selectively cross-linking T cells and tumor cells.

In one embodiment, the present invention provides a composition comprising anti-CD3 activated T cells (ATCs) or anti-CD3 and anti-CD28 co-activated T-cells (COATCs) armed with anti-CD3 (OKT3)×anti-CD22 bispecific monoclonal antibody. Upon administration, anti-CD3×anti-CD22 bispecific antibody-armed activated T cells attach to CD3-expressing T cells and CD22-expressing tumor cells, selectively cross-linking T cells and tumor cells.

In yet another embodiment, the present invention provides a composition comprising anti-CD3 activated T cells (ATCs) or anti-CD3 and anti-CD28 co-activated T-cells (COATCs) armed with anti-CD3 (OKT3)×anti-CD123 bispecific monoclonal antibody. Upon administration, anti-CD3×anti-CD123 bispecific antibody-armed activated T cells attach to CD3-expressing T cells and CD123-expressing tumor cells, selectively cross-linking T cells and tumor cells.

In another embodiment, the present invention provides a composition comprising anti-CD3 activated T cells (ATCs) or anti-CD3 and anti-CD28 co-activated T-cells (COATCs) armed with anti-CD3 (OKT3)×anti-CD38 bispecific monoclonal antibody. Upon administration, anti-CD3×anti-CD38 bispecific antibody-armed activated T cells attach to CD3-expressing T cells and CD38-expressing tumor cells, selectively cross-linking T cells and tumor cells.

In yet another embodiment, the present invention provides a composition comprising anti-CD3 activated T cells (ATCs) or anti-CD3 and anti-CD28 co-activated T-cells (COATCs) armed with anti-CD3 (OKT3)×anti-SLAMF7 bispecific monoclonal antibody. Upon administration, anti-CD3×anti-SLAMF7 bispecific antibody-armed activated T cells attach to CD3-expressing T cells and SLAMF7-expressing tumor cells, selectively cross-linking T cells and tumor cells.

In one embodiment, the present invention provides a composition comprising anti-CD3 activated T cells (ATCs) or anti-CD3 and anti-CD28 co-activated T-cells (COATCs) armed with anti-CD3 (OKT3)×anti-SASB1 bispecific monoclonal antibody. Upon administration, anti-CD3×anti-SASB1 bispecific antibody-armed activated T cells attach to CD3-expressing T cells and SASB1-expressing tumor cells, selectively cross-linking T cells and tumor cells.

In another embodiment, the present invention provides a composition comprising anti-CD3 activated T cells (ATCs) or anti-CD3 and anti-CD28 co-activated T-cells (COATCs) armed with anti-CD3 (OKT3)×anti-wnt1 bispecific monoclonal antibody. Upon administration, anti-CD3×anti-wnt1 bispecific antibody-armed activated T cells attach to CD3-expressing T cells and wnt1 expressing tumor cells, selectively cross-linking T cells and tumor cells.

In one embodiment, the present invention provides a composition comprising anti-CD3 activated T cells (ATCs) or anti-CD3 and anti-CD28 co-activated T-cells (COATCs) armed with anti-CD3 (OKT3)×anti-PMEL17 bispecific monoclonal antibody. Upon administration, anti-CD3×anti-PMEL17 bispecific antibody-armed activated T cells attach to CD3-expressing T cells and PMEL17-expressing tumor cells, selectively cross-linking T cells and tumor cells.

In another embodiment, the present invention provides a composition comprising anti-CD3 activated T cells (ATCs) or anti-CD3 and anti-CD28 co-activated T-cells (COATCs) armed with anti-CD3 (OKT3)×anti-CEA bispecific monoclonal antibody. Upon administration, anti-CD3×anti-CEA bispecific antibody-armed activated T cells attach to CD3-expressing T cells and CEA-expressing tumor cells, selectively cross-linking T cells and tumor cells.

In yet another embodiment, the present invention provides a composition comprising bispecific antibody-armed autologous T cells activated with anti-CD3 antibody and IL-2 and cultured in IL-7 or IL-7+IL-15 (See, for example, Gargett T, Brown M P. Different cytokine and stimulation conditions influence the expansion and immune phenotype of third-generation chieric antigen receptor T cells specific for tumor antigen GD2. *Cytotherapy* 2015, 17(4):487-495; Caserta S, Alessi P, Basso V, Mondino A. IL-7 is superior to IL-2 for ex-vivo expansion of tumour-specific CD4+ T cells. *Eur. J. Immunol* 2010, 40:470-479; and Cha E, Graham L, Manjili M H, Bear H D. IL-7+IL-15 are superior to IL-2 for the ex-vivo expansion of 4T1 mammary carcinoma-specific T cells with greater efficiency against tumors in vivo. *Breast Cancer Res Treat* 2010, 122:359-369).

In some embodiments, the present invention provides a composition comprising bispecific antibody-armed autologous T cells co-activated with anti-CD3 and anti-CD28 antibodies (either in solution or particle bound) and cultured in IL-2, L-7 or IL-7+IL-15.

In some embodiments, the present invention provides a composition comprising bispecific antibody-armed allogeneic T cells activated with anti-CD3 and IL2 and cultured in IL-2, IL-7 or IL-7+IL-15.

In yet another embodiment, the present invention provides a composition comprising bispecific antibody-armed allogeneic T cells activated with anti-CD3 and anti-CD28 (either in solution or particle bound) and cultured in IL-2, IL-7 or IL-7+IL-15.

Accordingly, it is contemplated that bispecific antibodies (BiAbs) can be prepared by any methods known in the art, and the resulting BiAbs are suitable for use in the present invention. In particular, BiAbs targeting tumor antigens found in multiple myeloma, non-Hodgkin's' lymphoma or leukemia are of particular interest to the methods and composition described herein. In yet another embodiment, BiAbs targeting tumor antigens found in pancreatic, breast, liver, ovarian, brain, prostate, lung, colon or colorectal cancer are of particular interest to the methods and composition described herein.

CAR-T Cells

Another approach to obtain T cells with anti-tumor reactivity without complications of HLA-restriction is chimeric antigen receptors (CARs, also known as chimeric immunoreceptors, chimeric T cell receptors, artificial T cell receptors or CAR-T). CAR-T are engineered receptors which graft an arbitrary specificity onto a T cell. Typically, these receptors are used to graft the specificity of a monoclonal antibody (e.g., CD19) onto the T cell, with transfer of their coding sequence facilitated by retroviral vectors. These artificial T-cell receptors allow grafting of nearly any specificity to T cells. This allows generation of large numbers of specific T cells without laborious selection and expansion procedures (see, for example, Pule, Finney and Lawson, Artificial T-cell receptors, *Cytotherapy.* 5 (3): 211-26, (2003) and Sadelain et al., *Therapeutic T cell engineering*, Nature, 545(7655):423-431 (2017).

CAR-T are constructed by linking an antigen binding domain, usually a single chain variable fragment (scFv), to an intracellular T cell signaling domain such as CD3-ζ (first generation CAR-T), and currently also including one or two co-stimulatory domains (second/third-generation CAR-T). The specific binding of CAR-T cells occurs in a non-MHC restriction manner, yet antigen binding results in T cell activation.

A CAR-T therapy for cancer using adoptive T cell transfer methods was recently approved by the US Food and Drug Administration (FDA) for use against acute lymphoblastic leukemia (ALL). Novartis, the company making and selling Kymriah™ (CAR-positive viable T cells) is charging $475,000 for the therapy, which based on FDA data, showed 83% of patients enrolled in the study with ALL were in complete remission within three months. As with adoptive T cell transfer, the patients T cells are removed from the patient and genetically modified so that they express receptors specific to the patient's cancer. To date, the most promising receptors have been found to target an antigen found on B cells (CD19) (See, Maude et al., *Blood,* 125:4017-23 (2015). Once the modified T cells have been engineered to express antigen-specific receptors they are expanded ex vivo and reintroduced into the patient where they recognize and kill the corresponding cancer cells expressing the tumor antigen. As will be apparent to one of skill in the art, the autologous techniques described above is contemplated to include CAR-T-cells sourced from donors other than the patient (i.e., allogeneic).

T cell therapy in general is often considered a last resort for patients because targeting T cells, which affect other components of the immune system can result in serious side effects, including cytokine release syndrome (sCRS) which presents as fever, hypotension, neurotoxicity, and even death. It is believed that lowering the dose of T cells reinfused into patients can offset the risk of the above side effects, while the CAR-T method produces 'memory' T cells for prolonged periods (e.g., years) after introduction into the cancer patient. The CAR-T therapy described above targets CD19, a marker expressed by normal B cells responsible for producing antibodies to foreign material. As such, some reports of B-cell aplasia have been observed. In order to compensate for this effect, it is recommended patients receive immunoglobulin therapy to provide them with necessary antibodies to fight off infections until such time their immune system can compensate for the B-cell aplasia.

Accordingly, it is contemplated that CAR-T cells can be prepared by any methods known in the art, and the resulting CAR-T cells are suitable for use in the present invention. In particular, CAR-T cells targeting an antigen found on B cells (e.g., CD19) are of particular interest. In another embodiment, CAR-T cells targeting tumor antigens found in multiple myeloma, non-Hodgkin's' lymphoma or leukemia are of particular interest to the methods and composition described herein. In yet another embodiment, CAR-T cells targeting tumor antigens found in pancreatic, breast, liver, ovarian, brain, prostate, lung, colon or colorectal cancer are of particular interest to the methods and composition described herein.

Tumor Infiltrating Lymphocytes (TILs)

Tumor infiltrating lymphocytes (TILs) are a type of white blood cells found in tumors. TILs are CD3+ cells that display activated natural killer cell (ANK) activity, but are more effective killers than ANK on a per cell basis (Rosenberg et al., *Science* 233:1318-1321 (1986)). Therapeutic TILs are a preparation of cells, comprising autologous tumor infiltrating lymphocytes that are manipulated in vitro and upon administration in vivo, re-infiltrate the tumor to initiate tumor cell lysis. To prepare therapeutic TILs in vitro, therapeutic tumor-infiltrating lymphocytes (TILs) can be isolated from tumor tissue and cultured with lymphokines such as IL-2; the TILs are then reinfused into the patient, where, after re-infiltration of the tumor, they may induce lysis of tumor cells and tumor regression.

In an exemplary embodiment, generation of TIL cultures is performed by first culturing resected tumor fragments or tumor single-cell suspensions in medium containing IL-2 for 3-5 weeks followed by a rapid expansion protocol (REP) involving the activation of TILs using an anti-CD3 monoclonal antibody in the presence of irradiated peripheral blood mononuclear cells (PBMC) and IL-2 (Rosenberg et al., Durable complete responses in heavily pretreated patients with metastatic melanoma using T-cell transfer immunotherapy. *Clin Cancer Res.* 17(13):4550-7 (2011)). Systemic administration of TILs to patients with advanced stage melanoma has mounted high and durable responses that resulted in objective clinical responses in >50% of the patients and complete regression in up to 24% of the patients (Id). With respect to re-infiltration of tumors, TILs have been reported to traffic to metastatic melanoma lesions (Griffith et al., *J. Natl. Cancer Inst.* 81:1709-1717 (1989)).

Clinical trials using TILs and high doses of IL-2 in patients with advanced renal carcinoma (RCC), metastatic melanoma (MM) and other advanced tumors have obtained clinical responses with most reports ranging between 15-20% (Topalian et al., *J. Clin. Oncol.* 6:839-853 (1988); Rosenberg et al., *N. Engl. J. Med.* 319:1676-1680 (1988); Rosenberg et al., *N. Engl. J. Med.* 323:570-578 (1990) and Goedegebuure et al., *J. Clin. Oncol.* 13:1939-49 (1995)).

One substantial limitation of TIL therapy are toxicities related to high doses of IL-2 infusions which restrict the use of IL-2 in patients who have poor performance status (Higuchi, C et al., *Blood* 77:2561-68 (1991)). The major toxicities of IL-2 are fluid gain and capillary leak leading to respiratory distress and hypotension often requiring vasopressor support and ICU monitoring, although other less serious side effects also prevail (Peace and Cheever. 1989. *J. Exp. Med.* 169:161-173). Although high doses of TIL alone can be infused without toxicities, the efficacy of TIL is thought to be linked to its co-administration with high dose IL-2. Another drawback to TIL therapy is that the rate of positive clinical responses from the combination of TIL and high dose IL-2 is unacceptably low. Unfortunately, the anti-tumor activity exhibited by TIL has not been consistently observed in large clinical studies (Rosenberg et al., 1986. *Science* 233:1318-1321). Therefore, new approaches to generate tumor specific CTLs to specifically target tumors are still needed.

Typically, tumor infiltrating lymphocytes (TILs) are expanded in vitro using high concentrations of IL-2 and anti-CD3. The expanded TIL cells are then reinfused into the patient along with one or more administrations of IL-2 to boost the TILs cytotoxic effect. However, before re-infusion, lymphodepetion of the cancer patient is required to eliminate regulatory T cells (which suppress or downregulate induction and proliferation of T cells) and unmodified T cells from competing with access to homeostatic cytokines.

Accordingly, it is contemplated herein that TILs prepared by any methods known in the art are suitable for use in the present invention. In one embodiment, TILs targeting tumor antigens found in multiple myeloma, non-Hodgkin's' lymphoma or leukemia are of particular interest to the methods and composition described herein. In another embodiment, TILs targeting tumor antigens found in pancreatic, breast, liver, ovarian, brain, prostate, lung, colon or colorectal cancer are of particular interest to the methods and composition described herein.

T-Cell Receptor Engineered T Cell (TCR Transgenic)

One strategy to circumvent the limitations associated with TILs is genetic engineering of autologous T cells by viral transduction to express T Cell Receptors (TCRs) that recognize tumor antigens.

Typically, genetically engineered T cells are created by harvesting T cells from a subject and infecting the T cells in vitro with a retrovirus or lentivirus that contains a copy of a TCR gene that is specialized to recognize tumor antigens (e.g., genes recognizing MART-1, gp100, NY-ESO-1 and p53, tumor antigens) (Morgan et al., *Science.* 314 (5796): 126-9. (2006)). The retrovirus or lentivirus integrates the T cell receptor gene into the T cells' genome and the genetically modified T cells are clonally expanded and stimulated ex vivo similar to methods set forth for adoptive T cell transfer. The expanded T cells are reinfused into the subject to produce an immune response against the tumor cells. This technique has been evaluated for at least metastatic melanomas, advanced skin cancers and leukemia's. (Hunder et al., Treatment of metastatic melanoma with autologous CD4+ T cells against NY-ESO-1, *N. Engl. J. Med.* 358 (25): 2698-703 (2008). It is well documented that expression of target antigens on healthy tissue results in unwanted off-target activity and thus it is preferable to utilize cancer specific antigens.

Accordingly, it is contemplated herein that genetically engineered TCRs on T cells prepared by any methods known in the art are suitable for use in the present invention. In one embodiment, genetically engineered TCRs targeting tumor antigens found in multiple myeloma, non-Hodgkin's' lymphoma or leukemia are of particular interest to the methods and composition described herein. In another embodiment, genetically engineered TCRs targeting tumor antigens found in pancreatic, breast, liver, ovarian, brain, prostate, lung, colon or colorectal cancer are of particular interest to the methods and composition described herein.

T-Rapa Cells

T-Rapa cells are T cells that are removed from a patient and incubated ex vivo in the presence of rapamycin. The incubated T cells are subjected to co-stimulation for example with various anti-CD antibodies (e.g., anti-CD3 and anti-CD28) and maintained in cell culture. Various methods are known in the art for preparing T-Rapa cells, for example, from peripheral blood (See, Fowler et al., *Blood,* 121:15, 2864-2874 (2013), which is incorporated herein by reference in its entirety).

Unarmed T-Rapa Cells

In some embodiments, T-Rapa cells are reinfused into a patient who provided the original T cells (autologous). Alternatively, T-Rapa cells can be administered to a patient who is different from the original donor of the T-cells (i.e., allogeneic). Reinfusion or administration of the activated T-Rapa cells to the subject is referred to herein as unarmed T-Rapa cells.

Bispecific Antibody Armed T-Rapa Cells

In some embodiments, after incubation with rapamycin, the T-Rapa cells may be modified as described herein to prepare bispecific antibody armed activated T-cells, such that the T-Rapa cells possess specificity for a tumor antigen and a T-cell stimulating binding domain, such as but not limited to anti-CD3. These bispecific antibody armed T-Rapa cells can then be reinfused to the subject who originally provided the T cells (autologous) or may be administered to a subject who was not the donor of the original T cells (i.e., allogeneic) by any methods available in the art.

In one embodiment, the present invention provides a composition comprising bispecific antibody-armed T-Rapa cells (See, for example, Fowler D H, Mossoba M E, Steinberg S M, Halverson D C, Stroncek D, Khuu, H M, et. al. Phase 2 clinical trial of rapamycin-resistant donor CD4+ Th2/Th1 (T-Rapa) cells after low-intensity allogeneic hematopoietic cell transplantation. *Blood* 2013, 121(15):2864-2874).

Accordingly, it is contemplated herein that T-Rapa cells (unarmed or bispecific armed. activated T cells) prepared by any methods known in the art are suitable for use in the present invention. In one embodiment, T-Rapa cells (unarmed or bispecific armed. activated T cells) targeting tumor antigens found in multiple myeloma, non-Hodgkin's' lymphoma or leukemia are of particular interest to the methods and composition described herein. In another embodiment, T-Rapa cells (unarmed or bispecific armed. activated T cells) targeting tumor antigens found in pancreatic, breast, liver, ovarian, brain, prostate, lung, colon or colorectal cancer are of particular interest to the methods and composition described herein.

IV. Vaccination & Priming of T Cells

Leukapheresis

Leukapheresis is the removal of blood cells for transfusion into patients who are treated with one or more T cell suppressing regimes, such as TBI or HDC. Typically, whole blood or bone marrow cells are withdrawn from the subject, and optionally separated into individual blood components. In the case of bone marrow, HSC are removed from a large bone of the donor, typically the pelvis, through a large needle that reaches the center of the bone. In the case of whole blood, peripheral blood can be withdrawn by venipuncture and passed through a machine that removes white blood cells, while returning red blood cells to the donor. Different processes can be employed during leukapheresis that may entail continuous or intermittent flow centrifugation. Alternatively, once obtained the white blood cells can be separated from other blood cellular components using a cell sorting device (e.g., a flow cytometer or Fluorescent Activated Cell Sorting (FACS)).

Generally, the complications of leukapheresis include difficulty in collection and short shelf life (24 hours at 20 to 24° C.) of the collected cells. Since the "buffy coat" comprising platelets and white blood cells sits directly above the red blood cell layer, a sedimenting agent such as hydroxyethyl starch (HES), can be employed to improve yield while minimizing red blood cell collection.

Once harvested from the bone marrow or peripheral blood the white blood cells can be frozen and stored, or manipulated for further use (e.g., for the preparation of cancer specific T cells or bispecific antibody armed activated T cells). In one embodiment, the white blood cells obtained by leukapheresis are further separated to obtain T cells that can be reinfused into the subject without further genetic modification (e.g., after clonal expansion) after the subject receives myeloablation and/or other T cell suppression treatment.

In a preferred embodiment, the T cells comprise T cells that were obtained from a peripheral blood draw as opposed to bone marrow or lymph node harvesting (See, for example, Chang et al., *J. Clin. Oncol.* 21:884-890 (2003).

In another embodiment, the leukapheresis step can include the isolation of T cells (e.g., from peripheral blood) where the T cells are already cancer specific T cells and the cancer specific T cells are clonally expanded in culture, prior to reinfusion into the subject. In some embodiments, the T cells are reinfused into the subject over a series of injections, e.g., at least one injection, preferably at least 3 injections, more preferably at least 5 injections. In one embodiment, the reinfusion regime can include once or twice weekly infusion into the subject. The frequency of infusions can be increased, although it is preferred that the infusions are not increased to the extent that the subject experiences adverse or substantial side effects from the influx of T cells on the subject's immune system (e.g., cytokine release syndrome). In one embodiment, PMBC (e.g., from whole blood) are activated with OKT3 and IL-2 and are expanded for up to 14 days.

Vaccination & Priming Regime

In one aspect, the invention provides a method to vaccinate (used interchangeably herein, with the term "immunize") a subject against an antigen(s) of interest. In a preferred embodiment, the method provides a method for vaccinating a subject against a tumor antigen(s) of interest by administering to the subject a cancer specific T cell vaccine population.

The vaccination step can be performed by the administration of one or more cycles/rounds of administration of the cancer specific T cell vaccine population to the subject. In one embodiment, the number of administrations (e.g., cycles) of the cancer specific T cell vaccine to the subject is at least 1 and less than 15. In a preferred embodiment, the number of administrations of the cancer specific T cell vaccine population to the subject is at least 3, at least 5, or at least 8, and less than 15 cycles.

In some embodiments, the vaccination step further comprises administration of dendritic cells as part of the cancer specific T cell vaccine population, or optionally, the administration of dendritic cells separately from the cancer specific T cell vaccine population. In another embodiment, the cancer specific T cell vaccine population is an autologous cancer specific T cell vaccine population. In yet another embodiment, the cancer specific T cell vaccine population is an allogeneic cancer specific T cell vaccine population. In some embodiments, the cancer specific T cell vaccine cell population further comprises professional antigen presenting cells.

In a preferred embodiment, the cancer specific T-cell vaccine cell population is bispecific antibody armed activated T-cells (BATs), Chimeric Antigen Receptor T-cells (CAR-T), Tumor infiltrating lymphocytes (TILs), T-cell receptor engineered T cells (TCR transgenic) or bispecific antibody armed or unarmed T-Rapa cells.

In one embodiment, the total number of cancer specific T cells that are administered to the subject in order to produce vaccination (e.g., immunization) of the subject is between 0.04 and 160 Billon cancer specific T cells. In another embodiment, the total number of cancer specific T cells in the vaccine population required to immunize the subject is between 5 million and 80 billion cells. In one embodiment, the total number of cancer specific T cells in the vaccine population required to immunize the subject is between 20 million and 20 billion cells. In another embodiment, the total number of cancer specific T cells administered to the subject to vaccinate the subject against the cancer specific antigen equates to the total number of cancer specific T cells required to prime immune T cells of the subject against the tumor antigen.

After administration of the cancer specific T cell vaccine population to the subject, one or more immune evaluations/examinations can be performed to determine if the amount of cancer specific T cells administered to the subject is amount sufficient to prime the endogenous T cells against the cancer specific antigen. In some embodiments, one or more T cells from the cancer subject are collected for analysis to determine whether the T cells are primed against the cancer antigen. In one embodiment, the method of collecting primed T cells includes leukapheresis (discussed herein) or other phlebotomy methods known in the art.

In one embodiment, immune T cells can be collected from the subject (after one or more cycles of vaccination or post-vaccination) to determine if the collected immune T cells specifically recognize the tumor antigen. In one embodiment, immune T cells can be collected from the subject within about 7 days after the last cycle of vaccination. Any methods known in the art can be used to determine if the collected immune T cells carrying an epitope that is specific for the tumor antigen. For example, epitope testing of one or more collected immune T cells can be performed. Epitopes can be mapped using protein microarrays, high-throughput mutagenesis, EliSpot or ELISA techniques or cellular cytotoxicity assays (see for example, FIG. 2A, herein).

In other embodiment, confirmation that the vaccination step was successful (i.e., the cancer specific T cell vaccine population produced immune T cells that are specific to the cancer antigen) can be confirmed by detecting the antigen-specific immune T cells by tetramer staining; while anti-tumor antigen antibodies can be detected by ELISA. As will be readily apparent to one or ordinary skill in the art, other assays can be used to assess whether post-vaccination, isolated T cells from the subject, carry an epitope that is specific for the cancer antigen of interest.

In some embodiments, the collected T cells can be obtained via a peripheral blood draw (e.g., leukapheresis). In another embodiment, the post-vaccination collected T cells can be obtained via leukapheresis of the subject and the T cells from the peripheral blood draw can be purified and/isolated from other cellular components of the peripheral blood draw (e.g., dendritic cells or B cells) to obtain a population of enriched immune T cells. In yet another embodiment, the collected T cells (post-vaccination) can be clonally expanded ex vivo, in the presence of one or more cytokines or interleukins. In one embodiment, the collected immune T cells can be clonally expanded ex vivo, preferably in the presence of IL-2, prior to epitope mapping.

Release of IFN-γ and other T helper 1 cytokines (e.g., IL-2, TNF-α) or T helper 2 cytokines (e.g., IL-4 and IL-10) from immune T cells in response to tumor stimulation is another exemplary method to confirm that a T cell obtained from a patient and activated ex vivo was in fact activated by the tumor antigen of interest. In this instance, isolated T cells can be directly co-cultured with irradiated autologous tumor cells or a tumor cell line, or activated ex vivo with anti-CD3 (e.g., immobilized anti-CD3) (e.g., for 2 days) and expanded in IL-2 (e.g., 60 U/mL of IL-2) for 3-5 days. In either case, the T cells are added to tumor target cells and tested for the release of cytokines (e.g., serum cytokines of interest). An exemplary technique by which to perform the above method, is commercially available enzyme-linked immunosorbent assay (ELISA) kits.

V. Culturing T Cells

Compositions of the present invention, such as T cells, activated T cells (including BiAb armed, activated T cells), or immune T cells, can be cultured ex vivo, using any methods available in the art. For example, T cells obtained from a subject (e.g., via leukapheresis) can be cultured ex vivo using commercially available T cell activation and expansion kits (See, ThermoFisher Scientific, Catalog No.: 11161D, which describes using Dynabeads for the activation and expansion of human CD3/CD28 T cells). Kits for the expansion of non-human T cells are also readily available (see, ThermoFisher Scientific, Catalog No.: 11456D, which describes using Dynabeads for the activation and expansion of mouse T cells). Commercial kits, such as those described above, offer various advantages over manually culturing cells, including the absence of feeder cells (antigen presenting cells (APCs)) and antigens. For example, Dynabeads are similar in size to APCs and are covalently coupled to anti-CD3 and anti-CD28 antibodies, which provide primary and co-stimulatory signals for T cell activation and expansion.

Upon T cell activation, the T cells mature into T helper cells or cytotoxic T lymphocytes (CTLs). Specifically, CD4+ cells can mature into mature T helper cells (Th$_1$ and Th2), while immature CD8+ cells can mature into CTLs. The activated T cells can be analyzed after activation (for transfection, transduction, TCR signaling, etc., by any methods available in the art) and are maintained in cell culture/media to differentiate into T helper cell subsets or expansion into a population of tumor antigen specific T-cells. Expansion of the T cell populations (e.g., activated T cells, BiAb armed, activated T cells, etc.) can be stimulated using IL-2 (e.g., recombinant IL-2) and other cytokines, such as but not limited to, IL-7, IL-21 and/or IL-15. After activation and expansion of the T cells, the magnetic beads can be easily removed using a DynaMag™ magnet.

When manually culturing T cells as opposed to using commercial kits, it is generally required to provide APCs and antigens to the T cell population. In some instances, activated T cells can be prepared by isolating T cells from a patient and activating the T cells ex vivo by either using soluble anti-CD3 antibody, or co-activation using anti-CD3 and anti-CD28 monoclonal antibodies, either soluble or immobilized on a solid support. Anti-CD3 upregulates the expression of IL-2 receptors and facilitates expansion in IL-2 containing media. Once activated, the T cells can be armed with a bispecific antibody (BiAb) (as discussed herein) or genetically modified (e.g., CAR-T or TCR Transgenic) to form cancer specific T cells. The activated T cells, armed activated T cells, or cancer specific T cells can be expanded in the presence of various reagents, including IL-2, IL-7, IL-21 and/or IL-15. Once the cells have reached a desired confluence or density, the cultured T cells can be transfused or reinfused into the subject (i.e., autologous or allogeneic T cell transplantation or adoptive T cell transfer) or stored for future use.

VI. Autologous Stem Cell Transplantation (ASCT)

Autologous Stem Cell Transplantation requires the extraction (apheresis) of hematopoietic stem cells (HSC) from a subject and reinfusion of the HSC into the subject at a later time. HSC cells can be obtained from peripheral blood or from a central line to a jugular, subclavian, or femoral vein.

In one embodiment, HSC are obtained from peripheral blood. In another embodiment, HSC are obtained from peripheral blood, where the peripheral blood is enriched for cells expressing CD34. In some embodiments, CD34+ cells may be isolated from peripheral blood (e.g., PMBC) using immunomagnetic or immunofluorescent (e.g, flow cytometry) methods. For example, Magnetic-Activated Cell Sorting (MACS) is a method for separation of various cell populations depending on their surface antigens CD molecules (Miltenyi et al., "High Gradient Magnetic Cell Separation With MACS," Cytometry, 11:2, 231-238, (1990)). The MACS method allows cells to be separated by incubating the cells of interest with magnetic nanoparticles coated with antibodies against a particular surface antigen (CD34+). This causes the cells expressing this desired antigen to attach to the magnetic nanoparticles. Afterwards, the cell solution is transferred on a column placed in a strong magnetic field. In this step, the cells attached to the nanoparticles (expressing the CD34+ antigen) stay on the column, while other cells (not expressing the antigen) flow through. In another embodiment, HSC can be isolated from PMBC by counter flow centrifugal elutriation (CaridianBCT Elutra; Cell Separation System) because monocytes may inhibit lymphocyte proliferation.

Once the CD34+ cells are collected they can be frozen (e.g., cryopreserved) and stored for reinfusion into the subject at a later date. Accordingly, an autologous SCT refers to the extraction of HSC from patient A and the reinfusion of the HSC to patient A, as opposed to the infusion of the HSC into patient B. To the contrary, an allogeneic SCT refers to the extraction of HSC from patient A and the infusion of the HSC to patient B, as opposed to the reinfusion of the HSC into patient A.

In one embodiment, isolation of HSC from the subject occurs after vaccination with the cancer specific T cell vaccine population (e.g., BAT infusions into the subject), and prior to immune suppression of the T cell population in the subject (e.g., before radiotherapy or chemotherapy). In one embodiment, isolation of HSC occurs after the last vaccination with the cancer specific T cell vaccine population.

In one embodiment, the HSC are administered to the subject in a single infusion. In another embodiment, the HSC are administered to the subject in a single infusion after the subject's T cell population (e.g., after myelosuppressive treatment) is less than 1000, 900, 800, 700, 600, 500, and preferably less than 400 T cells per mm$^3$.

In one embodiment, the subject is treated with chemotherapy with or without radiotherapy to eradicate all, or a portion of the subject's malignant cell population and to create space for the HSC to graft and expand, prior to the stem cell transplantation of the HSC. As such, the prepared HSC can then be infused or reinfused into the subject via intravenous administration, where the HSC resume normal blood cell production in the subject. Autologous SCT has the advantage of lower risks of infection and the incidence of subjects experiencing rejection is rare due to the donor and recipient being the same individual. These advantages have established autologous SCT as one of the standard treatments for such diseases as lymphoma (Canellos, Lymphoma Update, *The Oncologist.* 2(3): 181-3 (1997)).

However, for other cancers such as AML, reduced mortality of autologous SCT relative to allogeneic SCT may be outweighed by an increased likelihood of cancer relapse and related mortality, and therefore allogeneic HSC treatment may be preferred for those cancers (Bruno et al., A comparison of allografting with autografting for newly diagnosed myeloma, *N. Engl. J. Med.* 356 (11):1110-20 (2007)).

As such, the methods described herein contemplate the use of either autologous or allogeneic SCT as part of the treatment regime for specific forms of cancer.

VII. Suppressing T Cell Population

Myeloablation

Myeloablation is a severe form of myelosuppression. Myelosuppression is a condition in which bone marrow activity is decreased, resulting in fewer red blood cells, white blood cells, and platelets. It is a side effect of some cancer treatments and may also occur as a result of total body irradiation.

Lymphodepletion, the suppression of lymphocytes (e.g., B and T cells) before adoptive cell transfer based immunotherapies can enhance anti-tumor responses by augmenting innate immunity (Paulos et al., Toll-like receptors in tumor immunotherapy. *Clin Cancer Res.* 13:5280-9 (2007) and Paulos et al. Microbial translocation augments the function of adoptively transferred self/tumor-specific CD8+ T cells via TLR4 signaling. *J Clin Invest.* 117(8):2197-204 (2007)), by increasing access to homeostatic cytokines (Gattinoni et al. Removal of homeostatic cytokine sinks by lymphodepletion enhances the efficacy of adoptively transferred tumor-specific CD8+ T cells. *J. Exp. Med.* 202(7):907-12 (2005)), and by depressing the numbers of regulatory T cells (Antony and Restifo, CD4+CD25+T regulatory cells, immunotherapy of cancer, and interleukin-2. *J Immunother.* 28(2): 120-8 (2005)) and myeloid-derived suppressor cells in the subject (Bronte et al. Identification of a CD11b(+)/Gr-1(+)/CD31(+) myeloid progenitor capable of activating or suppressing CD8(+) T cells. *Blood.* 96(12):3838-46 (2000)).

It is an objective of the present invention, that the methods disclosed herein (and related compositions), following suppression of the T cell population in the subject, should result in less than 1000, 900, 800, 700, 600, 500 or most preferably, less than 400 T cells per $mm^3$.

High Dose-Total Body Irradiation

Total body irradiation (TBI) is a form of radiotherapy used as part of a preparative regimen for hematopoietic stem cell (HSC) transplantation. As the name implies, TBI involves irradiation of the entire body. Doses of total body irradiation typically range from 10 to >12 Gy, which is typically administered in a fractionated regime. Total body irradiation serves to suppress the recipient's immune system. Additionally, high doses of total body irradiation can eradicate residual cancer cells in the HSC transplant recipient.

High-dose total body irradiation (HD-TBI) given together with hematopoietic stem cell (HSC) transplantation has been found to effectively enhance adoptive cell transfer based immunotherapies. However, administration of HD-TBI can carry considerable short- and long-term toxicities including prolonged neutropenia with its associated risk for infection, renal insufficiency, interstitial pneumonitis, veno-occlusive disease of the liver, infertility, secondary solid tumor and hematologic malignancies and other complications (Chen et al. Radiation-associated pneumonitis following autologous stem cell transplantation: predictive factors, disease characteristics and treatment outcomes. *Bone Marrow Transplant.* 27(2):177-82 (2001); Moreau et al. Comparison of 200 mg/m(2) melphalan and 8 Gy total body irradiation plus 140 mg/m(2) melphalan as conditioning regimens for peripheral blood stem cell transplantation in patients with newly diagnosed multiple myeloma: final analysis of the Intergroupe Francophone du Myeloma 9502 randomized trial. *Blood.* 99(3):731-5 (2002); and Muranski et al. Increased intensity lymphodepletion and adoptive immunotherapy—how far can we go? *Nat Clin Pract Oncol.* 3(12):668-81 (2006)). These toxicities have motivated major efforts in the allogeneic transplant field to develop reduced intensity conditioning regimens (RIC) (see, Adkins and DiPersio, Total body irradiation before an allogeneic stem cell transplantation: is there a magic dose? *Curr Opin Hematol.* 15(6):555-60 (2008) and Sandmaier et al., Reduced intensity conditioning for allogeneic hematopoietic cell transplantation: current perspectives. *Biol Blood Marrow Transplant.* 13(Suppl 1):87-97 (2007)). RIC regimens have successfully achieved durable engraftment of donor stem cells and tolerable toxicities (See, Adkins and DiPersio).

Additionally, Wrzesinski et al., observed a strong correlation between the intensity of the conditioning regimen (lymphodepletion) and the efficacy of adoptive cell transfer based immunotherapies using linear regression analysis (*J. Immunother.*, 33(1): 1-7 (2010). They found a correlation existed for preparative total body irradiation administered either as a single dose (R=0.97, P<0.001) or in fractionated doses (R=0.94, P<0.001). Thus, increased intensity lymphodepletion was found to trigger enhanced tumor treatment efficacy but the benefits of high-dose total body irradiation must be titrated against its risks. Accordingly, a TBI regime of the present invention to suppress the T cell population in a subject, should result in less than 1000, 900, 800, 700, 600, 500 or most preferably, less than 400 T cells per $mm^3$.

Chemotherapy

Lymphodepletion before adoptive cell transfer based immunotherapies can also be performed via chemotherapy. High Dose Chemotherapy (HDC) regimens followed by autologous stem cell transplant have been utilized for the treatment of neuroblastoma's (see, NIH clinical trial identifier: NCT00567567), breast cancer (Stadtmauer, et al., (2000) Conventional-Dose Chemotherapy Compared with High-Dose Chemotherapy plus Autologous Hematopoietic Stem-Cell Transplantation for Metastatic Breast Cancer, New England Journal of Medicine. 342 (15): 1069-1076) and multiple myeloma's. As described in the Examples, provided herein, high dose chemotherapy was used to create immune space by depleting T regulatory cells and myeloid derived suppressor cells.

In one aspect, a single myeloablative regime can be used in the methods disclosed herein to obtain lymphodepletion. In one embodiment, a subject can receive a high-dose multi-agent chemotherapy induction regimen. For example an exemplary embodiment includes, a subject receiving melphalan intravenously (IV) over 15-30 minutes on days −7 to −5, etoposide (IV) over 24 hours and carboplatin (IV) over 24 hours on days −7 to −4, and granulocyte-colony stimulating factor (G-CSF) subcutaneously (SC) or (IV) beginning on day 0 and continuing until blood counts recover. With the subject undergoing autologous SCT on day 0.

Alternatively, a tandem myeloablative regime can be used in the methods disclosed herein to obtain lymphodepletion. For example an exemplary embodiment includes, a subject receiving thiotepa (IV) over 2 hours on days −7 to −5, cyclophosphamide (IV) over 1 hour on days −5 to −2, and G-CSF (SC) or (IV) beginning on day 0 and continuing until blood counts recover. Following clinical recovery from the initial myeloablative therapy, the tandem subjects can also receive melphalan, etoposide, and carboplatin as in the single myeloablative regime described above. With the subject undergoing autologous SCT on day 0.

Accordingly, it is an objective of the present invention, that the methods disclosed herein (and related compositions), following suppression of the T cell population in the subject, should result in less than 1000, 900, 800, 700, 600, 500 or most preferably, less than 400 T cells per mm$^3$.

Mild Chemotherapeutic Regimes

In another aspect, lymphodepletion can be obtained using mild chemotherapeutic treatment regimens (e.g., maintenance chemotherapeutic regimes), where the one or more chemotherapeutic agents are administered to the subject over multiple cycles (e.g., an high-dose induction stage coupled with reduced-dose or drug-change maintenance stage) such that the level of lymphocytes in the subject are suppressed to less than 1000, 900, 800, 700, 600, 500, or preferably less than 400 T cells per mm$^3$ after the mild chemotherapeutic treatment. One of the benefits of mild chemotherapeutic regimes is the ability to allow for additional cycles of chemotherapy while reducing the levels of toxicity in the subject from the chemotherapeutic drug(s).

For example, for most patients, treatment with more than 8 cycles of oxaliplatin for colorectal cancer produces a significant and often long-lasting neurotoxicity, so patients are advised to stop their oxaliplatin treatment after several months of induction therapy (the so-called "OPTIMOX" protocol). Because of this, a variety of maintenance approaches beyond the initial few months of oxaliplatin-containing combination chemotherapy have been studied. These maintenance approaches include the use of different chemotherapeutic drugs, such as bevacizumab alone, fluorouracil (5-FU) alone, combinations of bevacizumab and capecitabine, and combinations of bevacizumab and erlotinib. Notably, mild chemotherapeutic regimes have been reported to increase progression-free survival as compared to trials where the chemotherapeutic agent was halted after the induction stage (Koopman et al. Maintenance treatment with capecitabine and bevacizumab versus observation after induction treatment with chemotherapy and bevacizumab in metastatic colorectal cancer (mCRC): the phase III CAIRO3 study of the Dutch Colorectal Cancer Group (DCCG). *J Clin Oncol.* 31(suppl):abstr 3502 (2013).

It is an objective of the present invention, that the methods disclosed herein (and related compositions), following suppression of the T cell population in the subject, should result in less than 1000, 900, 800, 700, 600, 500 or most preferably, less than 400 T cells per mm$^3$.

VIII. Reinfusion of Cultured T Cells

Cultured T cells (including activated T cells and BiAb armed, activated T cells) can be reinfused into a subject using any method available in the art. For example, cultured T cells can be reinfused into a same individual as the donor of the T cells (autologous) or a different individual (allogeneic). In a preferred embodiment, the recipient of the cultured T cells has a tissue type that matches the donor (i.e., Human Leukocyte Antigen (HLA) compatibility).

In some embodiments, the cultured T cells are administered in a single dose. In another embodiment, the cultured T cells are administered over multiple doses, such as between one and fifteen (15) separate infusions into the subject. In a preferred embodiment, the number of cultured T cell administrations is between 5 and 15 infusions (i.e., 5, 6, 7, 8, 9, 10, 11, 12, 13, 14 or 15). In one embodiment, the cultured T cells are administered once or twice weekly over the course of 2-10 weeks. In another embodiment, the cultured T cells are administered once or twice weekly over the course of 4-8 weeks. In a preferred embodiment, the cultured T cells are administered after the SCT.

In some embodiments, reinfusion of cultured T cells occurs until a total number of cultured T cells of up to 160 Billion cells are reinfused into the subject. In one embodiment, the number of cultured T cells administered to the subject is between about 5 million and about 80 billion T cells. In another embodiment, the number of cultured T cells administered to the subject is between about 20 million and about 60 Billion cells. In yet another embodiment, the number of cultured T cells administered to the subject is between 100 million and 40 Billion cells. In some embodiments, the number of cultured T cells administered to the subject is between 1 billion and 100 billion T cells.

In one embodiment, the cultured T cells can be reinfused to the subject via intravenous delivery or intraperitoneally. In some embodiments, the cultured T cells can be administered to the subject via a pouch containing the cultured T cells, such as an IV bag, or may include infusion via a machine or pump that automatically regulates the number of cultured T cells administered to the subject.

IX. Absence of Traditional Drug Treatment after Immunotherapy

IL-2 & GM-CSF Toxicities

Typically, cancer patients who receive activated T cells, BiAb armed, activated T cells or other forms of adoptive T cell transfer are treated with cytokines, including IL-2 and GM-CSF as a means to stimulate growth and differentiation of the newly reinfused T cells. However, both of these cytokines (IL-2 and GM-CSF) have serious and potentially life-threatening complications that arise from toxicity within the subject.

Administration of IL-2 to cancer patients before, during, or after T cell adoptive transfer can result in fluid gain and capillary leak syndrome leading to respiratory distress and hypotension often requiring vasopressor support and ICU monitoring. Other side effects include fever, chills, malaise, diarrhea, increased creatinine, mental status changes, cardiac arrhythmias, and rashes. Adverse effects accompanying high dose, intravenous IL-2 therapy were observed to be severe, with cardiovascular, pulmonary, haematological, hepatic, neurological, endocrine, renal and/or dermatological complications frequently requiring doses to be withheld (Whittington & Faulds, Interleukin-2. A review of its pharmacological properties and therapeutic use in patients with cancer, *Drugs,* 46 (3): 446-514 (1993)).

Additionally, administration of recombinant GM-CSF to cancer patients before, during or after adoptive T cell transfer to stimulate blood cell production and growth is commonly associated with diarrhea, vomiting, internal bleeding, pain, chills, fever, fatigue, infection, weight loss, itching, and rashes. Other less frequent by serious side effects include cardiac arrhythmias, swelling of the arms/legs, kidney damage, capillary leak syndrome leading to respiratory distress and hypotension. In rare instances, individuals develop significant side effects resulting from the formation of blood clots that can lead to pulmonary embolus or stroke.

Furthermore, single or multiple administrations of IL-2 and GM-CSF to cancer patients cost substantial amounts of money and precious clinical resources. It is estimated by the inventors, that current treatment regimens comprising T cell adoptive transfer that include administration of recombinant IL-2 and GM-CSF to cancer patients equates to about $18,000 per patient. This cost increases if the patient receives more than the standard number of IL-2 and GM-CSF treatments.

As shown herein (see, for example, Sections "Immune ATC Transfer after SCT" and "Infusion Related Toxicities"), the Applicant demonstrates that no pre-treatment of cancer patients with IL-2 and GM-CSF is necessary to obtain improved immunotherapeutic responses based on the disclosed methods (see FIG. 1A). Additionally, post-adoptive T cell transfer treatment of the cancer patients with IL-2 and GM-CSF treatments is also not necessary to obtain improved immunotherapeutic results, as compared to the standard of care (which requires IL-2 and GM-CSF treatments). FIG. 1A provides an exemplary schema outlining the methods disclosed herein and no IL-2 or GM-CSF treatment is provided in the schema.

Additionally, FIG. 1C (measuring cytotoxicity and TTP) demonstrates % cytotoxicity against the specific tumor antigen observed in four patients (IT20007, IT20017, IT20020, and IT20031) in the absence of IL-2 and GM-CSF treatment. As can be seen in FIG. 1C, all four patients were observed to have higher % cytotoxicity against the tumor antigen as compared to patient FH1699 who received both IL-2 and GM-CSF treatment. Accordingly, GM-CSF and IL-2 treatment appeared to have a negative effect. Notably, 2 of the 4 patients not treated with IL-2 and GM-CSF (IT20020 and IT2007) showed improved cytotoxicity as compared to patient FH1702, who also received treated with both IL-2 and GM-CSF. Accordingly, the methods disclosed herein (and related compositions) provide substantial cost savings for cancer patients, health care insurers, and reduce the burden on clinician resources.

Accordingly, the Applicant has demonstrated that IL-2 and GM-CSF treatments are not necessary for the treatment of cancer or for improving immunotherapeutic responses using the methods disclosed herein, thereby negating the effects of IL-2 and GM-CSF toxicity in cancer subjects.

X. Measuring Immunotherapeutic Responses

A subject's immunotherapeutic responses to the methods of treatment described herein may be measured in multiple ways.

Cytotoxicity

In some embodiments, cytotoxicity of the activated T cells towards cancer cells may be used to determine a subject's immunotherapeutic responses to the methods of treatment described herein. Cytotoxicity may be determined by many available methods in the art, e.g., assessing cell membrane integrity, measuring the levels of ATP as a marker of viable cells, and/or measuring activities of various proteases as markers for viable, necrotic, and apoptotic cells. Chromium-51 release assay, as used in, e.g., Gall et al., *ExpHemnatol* 33:452, 2005, may be used to quantify cytotoxicity of the activated T cells towards cancer cells. In a Chromium-51 release assay, cancer cells may be loaded in vitro with radioactive chromium and lysis of the cancer cells may be determined by measuring chromium in the supernatant released by dying cancer cells. In the context of determining cytotoxicity of activated T cells toward cancer cells, chromium-51 release assay may be used to determine cytotoxicity towards specific types of cancer cells that the activated T cells are targeted against (e.g., breast cancer cells).

To measure cytotoxicity by assessing cell membrane integrity, various dyes, e.g., trypan blue and propidium iodide, which are normally excluded from the inside of healthy cells, may be used to stain necrotic or dead cancer cells whose cell membrane is often compromised. Cell membrane integrity may also be determined by monitoring the passage of substances that are normally sequestered inside cells to the outside. In the lactate dehydrogenase (LDH) assay, LDH reduces NAD to NADH which elicits a color change upon interaction with a probe outside of the cell. Other common methods for assessing cytotoxicity are enzymatic release assays which measure the extracellular activities of different enzymes, e.g., LDH, adenylate kinase (AK), and glyceraldehyde-3-phosphate dehydrogenase (GAPDH), outside of the cell in culture medium. Additional assays are also available to determine cytotoxicity, e.g., a bioluminescence-based cytotoxicity assay (see, e.g., Karimi et al., *PLoS One* 9:e89357, (2014)) and a real-time cytotoxicity assay (see, e.g., Fassy et al., *Curr Protoc Immunol.* 118:7.42.1-7.42.12, (2017)).

Cytokines

Serum cytokine levels may also be used to assess a subject's immunotherapeutic responses to the methods of treatment described herein. Cytokines are molecular messengers that allow the cells of the immune system to communicate with each other to generate a coordinated response to a target antigen or target cell (e.g., tumor antigens or cancer cells). Cytokines may directly stimulate immune effector cells (e.g., T cells and natural killer cells) at the tumor site and enhance tumor cell recognition by the immune effector cells. Cytokines are often released by T cells and natural killer cells and high levels of these cytokines may be associated with an effective immune response against cancer cells in the subject (see, e.g., Grabert et al., *Clin Cancer Res* 12:569, (2006)). In some embodiments, levels of one or more cytokines in a subject receiving the treatment may increase especially after the subject undergoes infusion of the activated T cells. As demonstrated herein, four of the six patients who were evaluated exhibited increased levels of IL-12 and Type 1 ($Th_1$) cytokines (e.g., IL-2, TNF-α, IFN-γ).

Cytokine levels in a subject receiving the methods of treatment as described herein may be determined by one or more methods available in the art, e.g., enzyme-linked immunoSpot (ELISPOT), enzyme-linked immunosorbant assay (ELISA), bead-based cytokine assay (see, e.g., Lehmann et al., *J Vis Erp.* 9:129, (2017) and Rodrigues et al., *Cytometry* 91:901, (2017)), and membrane-based cytokine assay (see, e.g., Altara et al., *J Transl Med.* 13:129, (2015)). For example, an ELISPOT assay may be used to quantify a subject's cytokine levels before, during, and/or after treatment. In an ELISPOT assay, a capture antibody specific to the cytokine in question may be coated onto a plate or membrane. The plate or membrane may be blocked with a serum protein to reduce non-specific background signal. Cells of interest (e.g., T cells) may be plated onto the plate or membrane at different densities, along with the antigen. After a period of incubation, cytokines secreted by the activated T cells may be captured locally by the capture antibody. Following a wash to remove any unbound components, the captured cytokines may be detected by an antibody specific to the cytokine and conjugated to, e.g., horseradish peroxidase (HRP) or a fluorescent readout. Cytokines that may be measured to determine a subject's immunotherapeutic responses to the methods of treatment include, but are not limited to, IL-2, IFN-γ, TNF-α, IL-12, IL-4, IL-10, IL-6, IFN-α, IFN-3, IL-5, IL-7, IL-8, IL-9, IL-15, IL-21, and GM-CSF. In some embodiments, cytokines that may be measured to determine a subject's immunotherapeutic responses to the methods of treatment are IL-2, IFN-γ, TNF-α, IL-12, IL-4, IL-10, and IL-6. In particular embodiments, an elevated level of one or more cytokines IL-12, IL-2, TNF-α, and IFN-γ in a subject receiving treatment may be an indication that the treatment is effective in the subject.

T Cell Phenotyping and T Cell Receptor (TCR) Repertoire

In further embodiments, the phenotypes of the T cells and/or B cells in a subject undergoing methods of treatment described herein may also be used to assess a subject's immunotherapeutic responses. When activated, T cells may display various phenotypes (i.e., different expressions of cluster of differentiation (CD) proteins on the cell surface) depending on the types of genes that are upregulated or downregulated. Using phenotypes of T cells and/or B cells as a method to assess the effectiveness of the treatment is described in the art, e.g., Lum and Culbertson, *J Immunol.* 135:185, (1985) and Disis et al., *Lancet* 373:673, (2009).

Figure 1B:
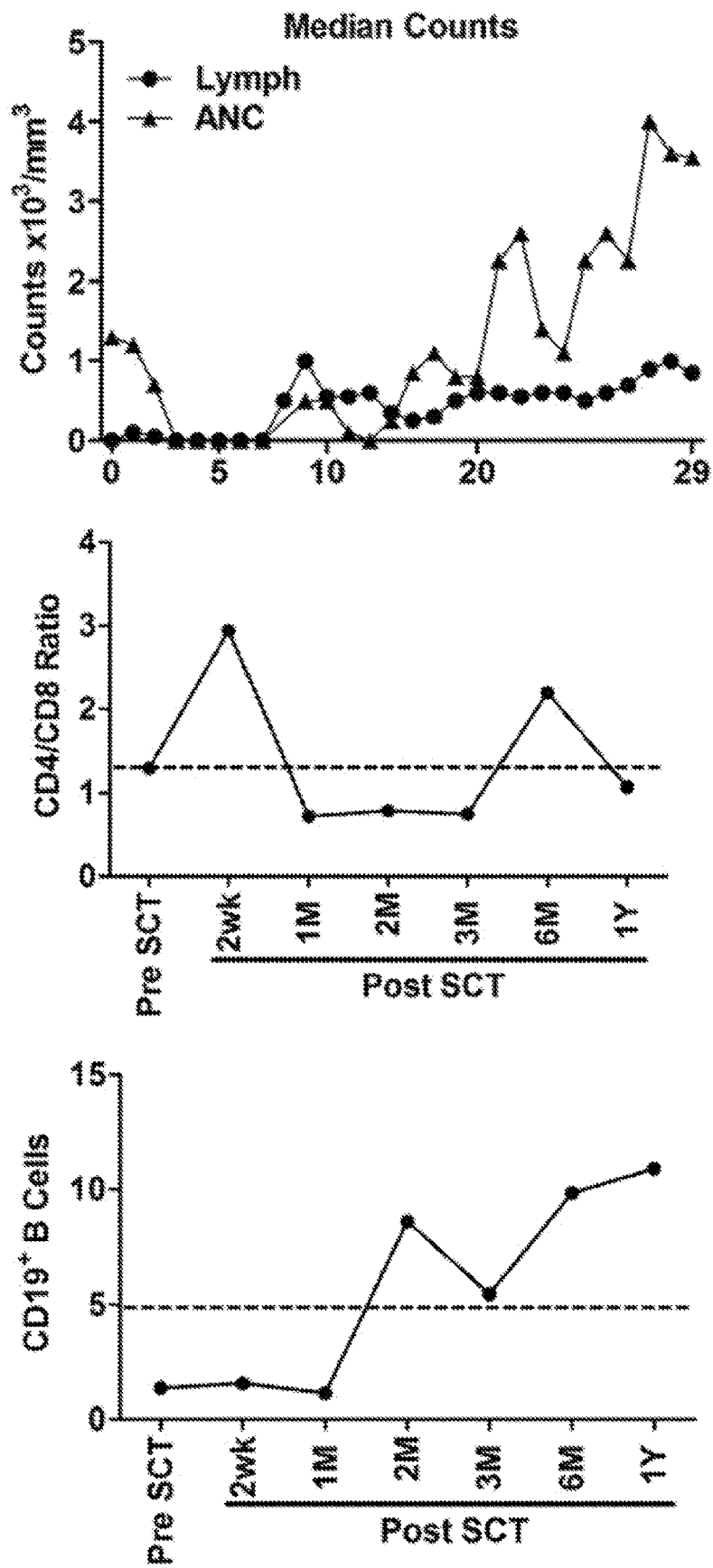
FIG. 1B shows the daily (horizontal axis) Lymphocytes (Lymph) and Absolute Neutrophil Counts (ANC) in patients (top panel). Middle panel shows CD4/CD8 ratio and bottom panel shows CD19+ B lymphocytes monitored up to 12 months post SCT.

In some embodiments, upon receiving treatment, a subject may exhibit an elevated level of $CD4^+$ and/or $CD8^+$ T cells, which can directly kill an antigen-expressing cell, secretes one or more cytokines (e.g., IFN-γ) and can elicit immune stimulatory and/or immune inhibitory effects. In some embodiments $CD4^+$ T cells may help to increase the level of $CD8^+$ T cells. For example, IFN-γ secreted by $CD4^+$ T cells may cause the activation of antigen-presenting cells, which in turn stimulate a $CD8^+$ T cell response. As demonstrated herein, following reinfusion of the activated T cells, subjects exhibited normalized CD4/CD8 ratio and an elevated level of $CD19^+$ B cells (FIG. 1B middle and lower panels).

The TCR repertoire of a subject's T cells may also change upon receiving treatment. The T cell repertoire develops during thymic selection with VB specificity determined by variable-beta (Vβ) and -alpha (Vα) chains and by post-thymic expansion. In some embodiments, the frequency of the T cells expressing TCR Vβ chains before and/or after infusions of the activated T cells may be determined. In other embodiments, T cells expressing TCR V chains that further express one or more cytokines (e.g., IL-2, IFN-γ, TNF-α, IL-12, IL-4, IL-10, and IL-6 (e.g., IL-12, L-2, TNF-α, and IFN-γ)) may also be determined in a subject treated by methods described herein.

Antibody Secretion

Figure 2A:
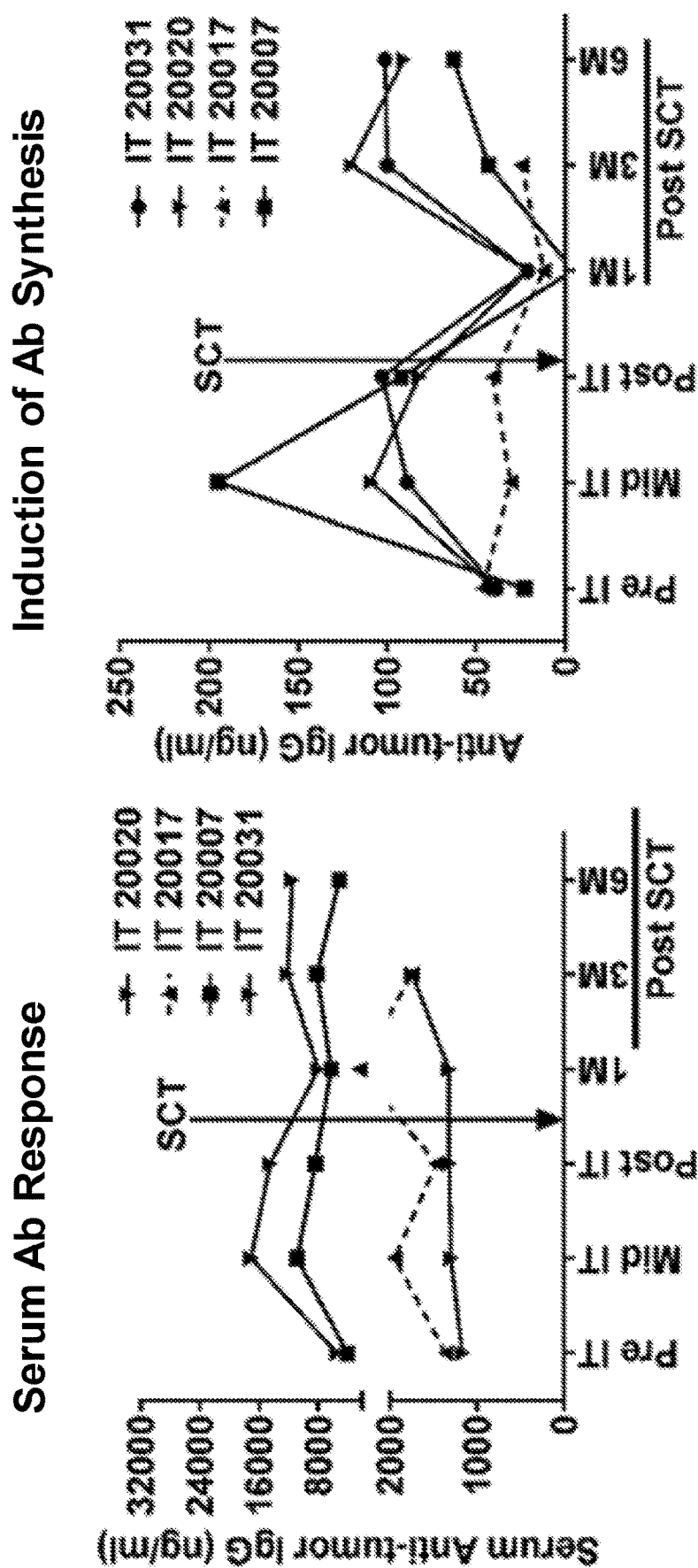
FIG. 2A shows transfer and reconstitution of T cell responses.

The production of cancer antigen- or cancer-cell specific antibodies by B cells in a subject may also be used to determine a subject's immunotherapeutic responses to the methods of treatment described herein. An increase in the synthesis of cancer antigen- or cancer-cell specific antibodies in the subject may be an indication that the subject is responsive to the treatment. As demonstrated herein, FIG. 2C shows serum anti-SK-BR-3 antibody levels at pre immunotherapy (IT), post IT, and post stem cell transplant. FIG. 2D also shows in vitro anti-SK-BR-3 antibody synthesis. About 25 ng/ml of specific antibodies were produced by PBMC at pre IT and up to 200 ng/ml (8 fold increase) of specific antibodies after IT. In vitro antibody synthesis increased from low levels in the first 2-3 months after stem cell transplant and persisted in 3 of 4 patients up to 6 months post stem cell transplant. The data suggest that booster activated T cell infusions after stem cell transplant provided T cell help to enhance specific B cell recovery and sustain serum antibody levels post stem cell transplant.

Tumor Volume

Tumor volume may also be measured to determine a subject's immunotherapeutic responses to the methods of treatment described herein. Tumor volume may be measured using art-known methods. See, e.g., Wapnir et al., *Breast Cancer Res Treat* 41:15-19, 1996; Sapi et al., *PLoS One* 10:e0142190, 2015. Tumor volume may be reduced by at least 10%, optionally at least 20% and sometimes by at least 50% after a course of treatment. In some embodiments, the reduction in tumor volume (e.g., at least 10%, 20%, or 30% reduction in tumor volume) may be observed as soon as within 1 month of initiating immunotherapy and/or within 1 month of initiating stem cell transplant. In other embodiments, the reduction in tumor volume (e.g., at least 10%, 20%, 30%, 40%, 50%, or 60% reduction in tumor volume) may be observed within 2, 3, 4, 5, or 6 months of initiating immunotherapy and/or within 2, 3, 4, 5, or 6 months of initiating stem cell transplant. In other embodiments, the methods described herein may also slow down or inhibit the further growth of a tumor (e.g., breast cancer tumor).

XI. Measuring Clinical Responses

Clinical responses of a subject being treated by methods described herein may be determined by, e.g., measuring overall survival, progression-free survival, and/or time to progression. In some embodiments, overall survival may be measured as median overall survival, which is a duration of time at which 50% of patients in the clinical trial are alive, or as a percentage of patients alive at different time points during the trial, i.e., at 1, 2, 3, 4, 5, or 10 years into the trial. In some embodiments, patients that are surviving longer may also mean that the time required to see a treatment effect when overall survival is used as the endpoint may be significantly extended.

Progression-free survival and time to progression may also be used as measures of clinical response. Progression-free survival refers to time from, during, and after treatment to disease progression or death. In some embodiments, progression-free survival also refers to the length of time during and after treatment of a disease, e.g., cancer, that a patient lives with the disease but it does not get worse until the patient dies. Time to progression refers to time from treatment to time of disease progression.

As demonstrated herein, the clinical responses of the patients were measured by time to progression from enrollment (from enrollment to cancer progression), by time to progression from post stem cell transplant (from post stem cell transplant to cancer progression), and by overall survival. One patient with progressive disease was stabilized by the combination of bispecific antibody armed activated T cells and immune activated T cells infusions and remained stable for 12.5 months. The median time to progression and overall survival for the 6 patients who received bispecific antibody armed activated T cells and immune activated T cells was 14.6 and 37.3 months, respectively; whereas the median time to progression and overall survival for all 8 patients (including 2 patients who did not receive a stem cell transplant) are 11.2 and 32.0 months, respectively. In contrast, the other 17 patients in the phase I clinical trial who received bispecific antibody armed activated T cells alone had a median time to progression and overall survival of 2.7 and 27.5 months, respectively.

Other indicators of clinical response for assessing the effectiveness of cancer treatment are also available in the art and can be found in, e.g., Oncology Endpoints in a Changing Landscape, Genentech, January (2016); Johansen et al., *J Mag Res Imaging* 29:1300, (2009); and Minckwitz et al., *Breast Cancer Res* 10:R30, (2008). Other indicators of clinical response include, but are not limited to, health-related quality of life, disease-free survival, objective response rate, duration of response, time to treatment failure, and pathological complete response.

XII. Compositions

In one aspect, the present invention provides a composition comprising a cell population for reinfusing into a cancer patient comprising between 0.4-160 Billion T cells cultured from the cancer patient vaccinated with a cancer specific T-cell vaccine cell population.

In some embodiments, the composition comprises a cell population for reinfusing into the cancer patient of between 1 billion and 100 billion T cells. In another embodiment, the composition comprises a cell population for reinfusing into the cancer patient of between 5 million and 80 billion T cells. In yet another embodiment, the cell population for reinfusing into the cancer patient comprises between 20 million and 60 billion T cells. In some embodiments, the cell population for reinfusing into a cancer patient further comprises peripheral blood or cultured or uncultured B cells. In one embodiment, the peripheral blood or cultured or uncultured B cells are B cells obtained from the cancer patient (i.e., autologous). In another embodiment, the peripheral blood or cultured or uncultured B cells are B cells obtained from a donor who is a separate individual as compared to the cancer patient (i.e., allogeneic), optionally who is not a cancer patient (e.g., healthy, non-cancerous donor).

In one embodiment, the composition comprises a cancer specific T-cell vaccine cell population that is an autologous cancer specific T-cell vaccine cell population. In another embodiment, the composition comprises a cancer specific T-cell vaccine cell population that is an allogeneic cancer specific T-cell vaccine cell population.

In a preferred embodiment, the composition comprises a cancer specific T-cell vaccine cell population that are bispecific antibody armed activated T-cells (BATs) or bispecific antibody armed or unarmed T-Rapa cells.

In some embodiments, the composition comprises a cancer specific T-cell vaccine cell population that is bispecific antibody armed activated T-cells wherein the bispecific antibody recognizes a tumor antigen or an epitope of a tumor antigen. In one embodiment, the cancer specific T-cell vaccine cell population is bispecific antibody armed activated T-cells wherein the bispecific antibody recognizes a tumor antigen, e.g., Human Epidermal Growth Factor Receptor 2 (HER2), Epidermal Growth Factor Receptor (EGFR), GD2, CD19, CD20, CD22, CD123, SLAMF7, CD38, SAS1B, wnt1, PMEL17, or Carcinoembryonic antigen (CEA).

In some embodiments, the composition comprises a cancer specific T-cell vaccine cell population that is bispecific antibody armed or unarmed T-Rapa cells wherein the bispecific antibody recognizes a tumor antigen or an epitope of a tumor antigen. In one embodiment, the cancer specific T-cell vaccine cell population is bispecific antibody armed or unarmed T-Rapa cells wherein the bispecific antibody recognizes a tumor antigen, e.g., Human Epidermal Growth Factor Receptor 2 (HER2), Epidermal Growth Factor Receptor (EGFR), GD2, CD19, CD20, CD22, CD123, SLAMF7, CD38, SAS1B, wnt1, PMEL17, or Carcinoembryonic antigen (CEA).

In another embodiment, the composition comprises a cancer specific T-cell vaccine cell population that is bispecific antibody armed activated T-cells activated with an anti-CD3 antibody or anti-CD3 and anti-CD28 antibodies. In some embodiments, the cancer specific T-cell vaccine cell population is bispecific antibody armed activated T-cells activated with an anti-CD3 antibody or anti-CD3 and anti-CD28 antibodies, and cultured in IL-2.

In yet another embodiment, the compositions comprises a cancer specific T-cell vaccine cell population that is CAR-T cells co-activated with anti-CD3 and anti-CD28 antibodies.

In another aspect, the present invention provides an autologous, cancer specific T-cell vaccine cell population for use in a method of immunotherapy of a cancer patient where the patient is not treated with IL-2 and GM-CSF, the method comprising (i) vaccinating the patient with the cell population in an amount sufficient to prime immune T-cells of the cancer patient; (ii) collecting the immune T-cells from the peripheral blood of the cancer patient; (iii) culturing the collected T-cells ex vivo; and (iv) reinfusing the cultured T-cells into the cancer patient.

EXAMPLES

The following examples are offered to illustrate, but not to limit the claimed invention.

Example 1: "Vaccination" and "Boosting" of Immune Responses in Cancer Patients

Arming activated T cells (ATC) with bispecific antibodies (BiAb) provides a non-toxic approach to enhance T cell killing of breast cancer (BrCa) cells (Sen M, Wankowski D M, Garlie N K, Siebenlist R E, Van Epps D, LeFever A V, et al. Use of anti-CD3×anti-HER2/neu bispecific antibody for redirecting cytotoxicity of activated T cells toward HER2/neu+ tumors. *J Hematother. Stem Cell Res.* 10(2): 247-26 (2001)). This approach was used to treat women with metastatic breast cancer (MBC) in a phase I trial. Infusions of anti-CD3×anti-HER2 BiAb armed ATC (BATs) were safe, induced anti-BrCa cytotoxic T lymphocytes (CTL), and induced a $Th_1$ cytokine pattern with encouraging clinical results (Lum L G, Thakur A, Al-Kadhimi Z, Colvin G A, Cummings F J, Legare R D, et al. Targeted T-cell Therapy in Stage IV Breast Cancer: A Phase I Clinical Trial. *Clin. Cancer Res.* 21(10):2305-2314 (2015)).

In another phase I study, infusions of unprimed ATC in women with MBC after autologous stem cell transplant (SCT) suggested that infusions of unprimed and unarmed ATC provided an anti-tumor effect (Lum L G. Immunotherapy with Activated T Cells after High Dose Chemotherapy and PBSCT for Breast Cancer. In: Dicke K A, Keating A (eds). Carden Jennings: Charlottesville, N Y, 2000, pp 95-105). At 32 months, 50% of the patients who received the unprimed ATC were stable and 75% were alive whereas 15% of those who received SCT alone were stable and 50% alive. Id. Although SCT for the treatment of breast cancer remains controversial, a recent meta-analysis of 15 randomized high-risk primary breast cancer trials (n=6102) showed a 13% event-free survival benefit for SCT (P=0.001) over standard of care with a 6 year median follow-up (Berry et al. High-dose chemotherapy with autologous stem-cell support as adjuvant therapy in breast cancer: overview of 15 randomized trials. *J. Clin. Oncol.* 29(24):3214-3223 (2011)).

The study presented herein was designed to demonstrate that MBC patients "vaccinated" with infusions of BATs could be "boosted" with infusions of ex vivo expanded, cultured immune ATC, after high dose chemotherapy (HDC) and SCT, to enhance transfer of anti-breast cancer immunity.

The study takes advantage of SCT to reduce tumor burden, create immune space, and augment transfer of anti-tumor immunity. We present evidence that BATs induce breast cancer-specific cellular, humoral, and innate immunity that can be transferred with infusions ("boosts") of immune ATC and stem cells.

Materials and Methods

Study Population, Patient Enrollment and Eligibility
Eligibility
Women, 18 years of age or older, with histologically documented metastatic carcinoma of the breast were eligible. No measurable disease was allowable and patients were enrolled only when the tumor or metastatic disease had been removed or successfully treated prior to entry into the protocol. Women were eligible for therapy irrespective of their HER2/neu expression status since in our previous testing, bispecific (Her2Bi) armed ATC (BATs) induced cancer-specific immunity even in women whose tumors were HER2/neu negative. Patients with previously treated and/or stable brain metastases or who have received prior hormone therapy, chemotherapy, and/or Herceptin® therapy were eligible. Patients must have a Karnofsky performance score of >70 or an ECOG, PS=0-2, and a life expectancy of 3 months or more.

Patients were ineligible for this protocol if they have: a PFT-FEV1, DLCO, and FVC<60% of normal; creatine >1.8 mg/dl or creatinine clearance of <60 ml/min; direct bilirubin, SGOT or SGPT>1.5 times normal; severe cardiac dysfunction or disease, uncontrolled hypertension (systolic BP ≥130 and/or diastolic BP ≥80; a MUGA ejection fraction <50%; psychiatric illness that prevents informed consent; an active infection; HIV antibody positivity; untreated cavities or tooth decay (which increases risk for infection post-ASCT); uncompensated major thyroid or adrenal dysfunction; significant skin breakdown from tumor or other disease; evidence of pregnancy or lactation; or an inadequate SC harvest. Minor changes from these guidelines were allowed at the discretion of the treating physician and all deviations were recorded.

The phase I trial was registered on clinicaltrial.gov as NCT00027807. Women, 18 years of age or older, with histologically documented MBC of the breast with 0-3+ HER2/neu expression with no measurable disease were eligible. Eight of 23 patients in the phase I were treated in this study. This trial was registered at clinicaltrial.gov as NCT00020722. All protocols were approved by protocol review committee, Institutional Review Boards at Roger Williams Hospital and Wayne State University, and the FDA. All patients signed informed consent forms.

Immunization with BATs and Expansion of Pre-Immunized ATC

Patients received a total of 8 biweekly BATs infusions over 4 weeks, and subcutaneous injections of $3.0\times10^5$ IU of IL-2/m²/day and 250 µg granulocyte-macrophage colony stimulating factor (GM-CSF)/m² twice weekly starting 3 days before the 1$^{st}$ BAT infusion and ending 7 days after the last BATs infusion (see, FIG. 1A, Treatment Schema and Lum et al. Targeted T-cell Therapy in Stage IV Breast Cancer: A Phase I Clinical Trial. *Clin. Cancer Res.* 21(10): 2305-2314 (2015)). Seven to 14 days after the last BATs infusion, the patients were leukapheresed for the expansion of immune T cells. The collected immune activated T cells were cultured, harvested and cryopreserved after 14 days for infusions after SCT (details below).

G-CSF Primed PBMC Collection for SCT

Following peripheral blood mononuclear cells (PBMC) collection for generating pre-immunized ATC, PBMCs were collected by 1-2 leukapheresis to obtain a minimum of $1\times10^6$/kg of CD34+ cells after 4 days of priming with granulocyte-colony stimulating factor (G-CSF at a dose of 15 µg/kg/day) for SCT.

High Dose Chemotherapy (HDC) to Reduce Tumor Burden

Patients received cyclophosphamide, thiotepa, and carboplatin (CTC; Stamp V) as the preparative regimen for chemosensitive disease and ifosfamide, carboplatin, and etoposide (ICE) for chemoresistant disease. For the CTC regimen (chemosensitive disease): Cyclophosphamide (2000 mg/m2 i.v.) was given on days −4, −3, and −2 (total=6000 mg/m2); Thiotepa (167 mg/m2 IV) on days −4, −3, −2 (total=500 mg/m2); Carboplatin (267 mg/m2 IV) on days −4, −3, and −2. For the ICE regimen (chemoresistant disease): Ifosfamide (2,500 mg/m2 IV) was infused on days −8 to −3 (total dose=15,000 mg/m2) with Mesna (1,000 mg/m2 IV) given beginning 30 min before the start of each ifosfamide dose and then as a continuous IV infusion (1,500 mg/m2) over next 12 hours; Carboplatin (250 mg/m2) on days −8, −7, −6, −5, −4, and −3 (total dose=1500 mg/m2); Etoposide (VP-16; 200 mg/m2 IV) on days −8, −7, −6, −5, −4 and −3 (total dose=2,400 mg/m2).

Stem Cell Transplant

On day 0, the cryopreserved peripheral blood stem cells (HSC) were thawed and infused at the bedside.

Immune ATC Transfer after SCT with and without Cytokine Treatment

Two patients received infusions of up to $10^{10}$ activated T cells three times per week beginning day +4 after SCT for three weeks and then once weekly infusions of up to 20×10' for 6 weeks. Daily subcutaneous injections of IL-2 ($3.0\times1^0$ IU/m²/day) were given starting on day +4 after SCT and ending on the day of the last infusion. GM-CSF (250 µg/m² twice per week) was given for 3 weeks starting day +5. A second group of patients (n=4) (patients referred to herein as "IT20007T", "IT2001T", "IT20020" and "1T20031") received ATC twice per week for 4 weeks without IL-2 or GM-CSF treatments (See, for example FIGS. 1C and 2A).

Infusion Related Toxicities

All vital signs and side effects were recorded on the patient's chart using the NCl CTC v3.0 toxicity table. Patients were observed up to 6 hours after their infusions. Patients with grade 4 non-hematologic toxicity or persistent grade-3 toxicity would be removed from the study. Infusions were held until toxicity improved to grade 0 or 1.

Specific Cytotoxicity, IFN-γ EliSpots, Serum Cytokines, Phenotyping and Anti-SK-BR-3 Specific Antibodies Specific cytotoxicity was performed using fresh PBMC plated with $^{51}$Cr labeled SK-BR-3 cells at effector:target (E/T) of 25:1 unless otherwise indicated (Wahren et al. Transfer and persistence of viral antibody-producing cells in bone marrow transplantation. *J. Infect. Dis.* 150: 358-365 (1984)).

The IFN-γ Elispots were used to measure CD8-mediated memory CTL activity and CD4-mediated helper responses (Rapoport A P, Stadtmauer E A, Aqui N, Badros A, Cotte J, Chrisley L. et al. Restoration of immunity in lymphopenic individuals with cancer by vaccination and adoptive T-cell transfer. *Nat. Med* 11(11): 1230-1237 (2005)).

Cytokines were measured by Luminex Array and phenotyping was performed by multicolor flow Cytometry (Matsue et al., Proliferative and differentiative responses of B cells from human marrow graft recipients to T cell-derived factors. *Blood,* 69:308-315 (1987)).

Immune responses were monitored by specific cytotoxicity (Gall J M, Davol P A, Grabert R C, Deaver M, Lum L G. T cells armed with anti-CD3×anti-CD20 bispecific antibody enhance killing of CD20+ malignant B-cells and bypass complement-mediated Rituximab-resistance in vitro. *Exp. Hematol.* 33(4): 452-459 (2005)), IFN-gamma Elispots (Grabert R C, Cousens L P, Smith J A, Olson S, Gall J, Young W B, et al. Human T cells armed with Her2/neu bispecific antibodies divide, are cytotoxic, and secrete cytokines with repeated stimulation. *Clin. Cancer Res.* 12(2): 569-576 (2006)), serum cytokines (Id.), and T cell phenotyping (Id.).

NK activity was assessed using K562 targets. TCR Vβ repertoire of human T cells were determined by multi-color flow cytometry (discussed below).

Anti-SK-BR-3 Specific Antibody Detection.

The Applicants developed a whole cell ELISA to detect antitumor specific antibody response. (See, Thakur et al., In vitro synthesis of primary specific anti-breast cancer antibodies by normal human peripheral blood mononuclear cells. *Cancer Immunology, Immunotherapy* 2011, 60(12): 1707-1720 and Thakur et al., Induction of specific cellular and humoral responses against renal cell carcinoma after combination therapy with cryoablation and granulocyte-macrophage colony stimulating factor: a pilot study. *Journal of Immunotherapy*, 34(5):457 (2011)). Briefly, the SK-BR-3 cells were plated on flat-bottomed 96 well plates at a concentration of 100,000 cells/well. Cells were allowed to settle and spread at room temperature for 30 minutes. Adhered cells were dried and fixed with absolute ethanol at 4° C. for 10 minutes followed by blocking with 1% BSA and 1% normal goat serum in PBS with 0.05% Tween 20. For antibody detection, serial dilutions of "immunized" serum from patients who were treated with 8 infusions of BATs were placed into the wells coated with SK-BR-3 (act as a pool of tumor antigens), this allowed the antibodies in the serum to bind to surface antigens on the fixed cells, followed by detection of bound antibodies using goat-anti-human IgG.

Induction of In Vitro Specific Anti-Breast Cancer Antibody Synthesis

An assay for the induction of tumor specific antibody synthesis was set-up as described previously. (See, Gall et al., T cells armed with anti-CD3×anti-CD20 bispecific antibody enhance killing of CD20+ malignant B-cells and bypass complement-mediated Rituximab-resistance in vitro. *Exp. Hematol.* 33(4): 452-459 (2005)). Briefly, PBMC were co-cultured with SK-BR-3 cells at 10:1 ratio in the presence or absence of 5 µg/ml CpG-B or control oligonucleotide (ODNs) and $0.25 \times 10^6$ autologous ATC or BATs irradiated at 2500 rads. The mean of IgG antibody production in triplicate cultures was measured by antibody directed at SK-BR-3 cells and is expressed as $ng/ml/10^6$ cultured cells.

TCR Vβ Repertoire

Quantitation of TCR Vβ repertoire of human T cells were determined by multicolor flow cytometry using the IOTest® Beta Mark Kit (Beckman Coulter) as per the manufacturer's instruction. The kit was designed to group Vβ specificities into mutually exclusive combinations to detection expression of 3 Vβ repertoires of T cells with or without further differentiation into CD4, CD8 and IFN-γ producing Vβ repertoire in total in 8 preparations.

Statistical Analyses

Wilcoxon signed-rank test was used to compare baselines with each time point from pre-study for cytotoxicity and IFN-γ Elispots against SK-BR-3 cells. Spearman correlation and log-rank tests were used to test the correlation between ATC cytotoxicity and TTP. GraphPad Prism version 6 for Windows (GraphPad Software, San Diego, CA) and Stata 13 (StataCorp L P, College Station, TX) were used for statistical analysis.

Results

Clinical Status

FIG. 4 summarizes patient age, HER2 status, prior therapies, doses of BATs and ATC, days to myeloid and lymphoid engraftment, time to progression (TTP), overall survival (OS) from enrollment or SCT, and disease status.

In 8 patients enrolled, 7 patients had visceral disease: 4 had stable disease (SD), and 4 had progressive disease (PD). Four of six evaluable patients who received BATs and immune ATC after SCT were stable at 6 months post SCT.

BATs Infusions with IL-2 and GM-CSF

Eight women were enrolled in the dual protocol treatment (NIH clinical trial identifiers: NCT02173093 and NCT02620865). Six women successfully completed both protocols involving 8 infusions of $10\text{-}15 \times 10^9$ BATs over 4 weeks along with IL-2 and GM-CSF. Of the 8 patients, 2 patients did not receive SCT or immune ATC infusions because they progressed before they could undergo a SCT (IT20006 and IT20038, data not shown).

The data from two of 8 patients who received BATs but did not undergo a SCT are presented. One patient (IT20020) with PD was stabilized by the combination of BATs and immune ATC infusions and remained stable for 12.5 months. The median TTP and OS for the 6 patients who received BATs and ATC was 14.6 and 37.3 months, respectively; whereas the median TTP and OS for all 8 patients (including 2 patients who did not receive a SCT) are 11.2 and 32.0 months, respectively. In contrast, the other 17 patients in the phase 1 clinical trial who received BATs alone (i.e., who did not receive "boost" infusions) had a median TTP and OS of 2.7 and 27.5 months, respectively. The above data demonstrates that TTP and OS were improved when patients received a "vaccinate" (i.e., administration of BATs) and "boost" (administration of cultured activated T cells) treatment regime as compared to BATs alone treatment, optionally combined with a SCT.

Statistical Analysis Results for the Correlation Between ATC Cytotoxicity and TTP Spearman correlation coefficient was calculated and tested for the correlation between anti-breast cancer cytotoxicity by ATC and TTP. By grouping ATC cytotoxicity level to high (>15) or low (<=15), log-rank test was applied to examine the difference in progression-free survival between patients with the high versus low ATC cytotoxicity level. The results show that TTP has a significantly positive correlation with ATC cytotoxicity level (Spearman correlation coefficient r=1, p<0.002) (FIG. 1C, lower panel). In addition, patients with high ATC cytotoxicity had significantly longer TTP (Log-rank test p=0.025). Overall survival (OS) did not correlate with levels of cytotoxicity, although all patients that showed an increase in immune ATC cytotoxicity ≥13.7% over baseline had markedly greater OS than those with less than 13.7% change (34.3-81.4 months vs. 5-9-16.8 months, respectively).

Neutrophil and lymphocyte recovery is shown in FIG. 1B, top panel. Phenotyping for T and B lymphocytes show that early post-SCT infusions of ATC transiently normalized the CD4/CD8 ratio (FIG. 1B, middle and lower panels). The phenotypes and cytotoxicity of harvested products (BATs and ATC) are shown in FIG. 6.

Adverse Events

Chills, fever, fatigue, headache and hypotension associated with BATs infusions have been reported (Lum L G, Thakur A, Al-Kadhimi Z, Colvin G A, Cummings F J, Legare R D, et al. Targeted T-cell Therapy in Stage IV Breast Cancer: A Phase I Clinical Trial. *Clin Cancer Res* 21(10): 2305-2314 (2015)). Patients who received ATC experienced chills and grade 1-2 headaches and recovered within 24 hours after the infusions. One patient experienced chills following 3 of 8 infusions and a second patient developed sepsis associated with tachycardia, hypotension, nausea, diarrhea, ARDS, hypoxia, renal failure, infection 3 days following ATC infusion #2 resulting in an ICU transfer. The patient fully recovered and ATC infusions #3-8 were resumed 3 months later with no toxicities ≥grade 2. The patient is alive with stable disease on chemotherapy.

Immune ATC Infusions after SCT with and without Cytokine Treatment

Since breast cancer-specific immunity was strongest at one week after the last BATs infusion in phase I MBC patients, immune T cells were collected by leukapheresis at this time for ATC expansion. Two patients (FH1699 and FH1702) received 3 infusions of expanded, cultured immune T cells per week for the first 3 weeks after HDC and SCT and 1 infusion per week for 6 weeks for a total of 15 ATC infusions. Another 4 patients (IT20007, IT20017, IT20020, and IT20031) received 8 ATC infusions given twice per week for 4 weeks and no IL-2 or GM-CSF treatments (see, FIG. 1C, FIGS. 2A and 2B).

Transfer of Tumor Specific T Cell Immunity by Immune ATC after SCT.

Immune testing was performed in 4 of 6 patients. All 4 patients increased their immediate CTL activity during and after infusions of BATs. CTL activity appeared between 2 weeks and 2 months and recovered to the levels seen after BATs infusions by 3-6 months after SCT in 3 out of 4 patients (FIG. 2A, left panel).

Immediate IFN-γ EliSpots to breast cancer stimulation were restored by 1 month and persisted up to 3-12 months post SCT. Three of 4 patients with stable disease at least 6 months or more after SCT showed enhanced anti-tumor T cell responses (FIG. 2A, right panel). Patient IT20007 who had TTP of 28.7 months, showed peak anti-breast cancer cytotoxicity of 37% at 3 months, and a 2 fold increase in IFN-γ EliSpots/$10^6$ PBMC after SCT from pre-SCT of 550 to 1,100 IFN-γ EliSpots at 6 months after SCT. Patient IT20020 had a peak cytotoxicity of 12% at 2 months post-SCT compared to less than 3% pre SCT and restored IFN-γ EliSpot responses at 6-12 months; this patient was progression free at 12.5 months. Patient IT20031 who had a TTP of 6.3 months had more than a 2 fold increase in specific anti-breast cancer cytotoxicity at 1 month post SCT that persisted up to 3 months and reached remarkably high cytotoxicity of 45% at 6 months post SCT. The immediate non-MHC restricted specific cytotoxicity and IFN-γ secretion mediated by specific TCR clones has been described by Simpson-Abelson et al (IL-12 delivered intratumorally by multilamellar liposomes reactivates memory T cells in human tumor microenvironments. *Clin. Immunol.*, 132(1): 71-82 (2009)).

Likewise, IFN-γ EliSpots were 2-5 fold higher than the pre SCT IFN-γ EliSpot activity as early as I month that persisted up to 3 months after SCT. It is noteworthy that one patient (IT20017, TTP 3.9 months) who progressed rapidly after SCT had high specific cytotoxicity (30%) pre SCT that sharply decreased at 1 month after SCT and continued to decrease thereafter, while IFN-γ EliSpots could not be detected after SCT. High levels of NK activity (data not shown) were also induced by infusions of BATs and these high levels persisted after SCT.

Neutrophil, Lymphocyte Recovery and Immune Reconstitution

Neutrophil and lymphocyte engraftment (500/mm3) occurred between days 9-19 and 8-17, respectively, after SCT. Phenotyping showed that a CD4/CD8 ratio reached a normal range within 6 months after SCT. The overall cell phenotype patterns suggest that early infusions of ATC accelerated the reconstitution of the T and B lymphocytes within 3-6 months (FIG. 1B, middle panel).

Phenotype and Cytotoxicity of Harvested Products (BATs and Immune ATC)

FIG. 6 shows the CD3, CD4, CD8, and CD56 composition of ATC after expansion in culture. The median percent (range) of CD3, CD4, CD8, and CD56 was 79.9 (34-93), 52.9 (25-78), 29 (8-31), and 15 (6-29), respectively, in the expanded ATC obtained after BATs infusions. The ratio of CD4/CD8 ranged from 0.84 to 5.7. The cytotoxicity exhibited by the expanded, cultured immune ATC showed significant enrichment of "vaccinated" polyclonal anti-tumor T cells clones (FIG. 6).

Transfer of Humoral Immunity

Next, we determined whether BATs infusions would induce anti-tumor humoral immunity, and whether humoral immunity could be transferred and augmented with multiple infusions of immunized ATC after SCT.

FIG. 2C cont'd shows serum anti-SK-BR-3 antibody levels at pre-immunotherapy (IT), post-IT, and post-SCT.

FIG. 2C cont'd shows in vitro anti-SK-BR-3 antibody synthesis. Given low precursor frequency of antigen-specific B cells, the antibody synthesis by B cells is quite remarkable. About 25 ng/ml of specific IgG were produced by PBMC at pre IT and up to 200 ng/ml (an 8 fold increase) of specific IgG after IT. Antibody synthesis increased from low levels in the first 2-3 months after SCT and persisted in 3 of 4 patients (IT20007, IT20020, and IT20031) up to 6 months post SCT (FIG. 2C cont'd). In one patient with PD (1T20017), antibody synthesis and memory B cell responses were low suggesting that IT20017 lacked robust cellular and humoral immune responses. Our data suggest that "booster" ATC infusions after SCT provided T cell help to enhance specific B cell recovery and sustain serum antibody levels post SCT.

Serum Cytokine/Chemokine Levels.

Figure 3A:
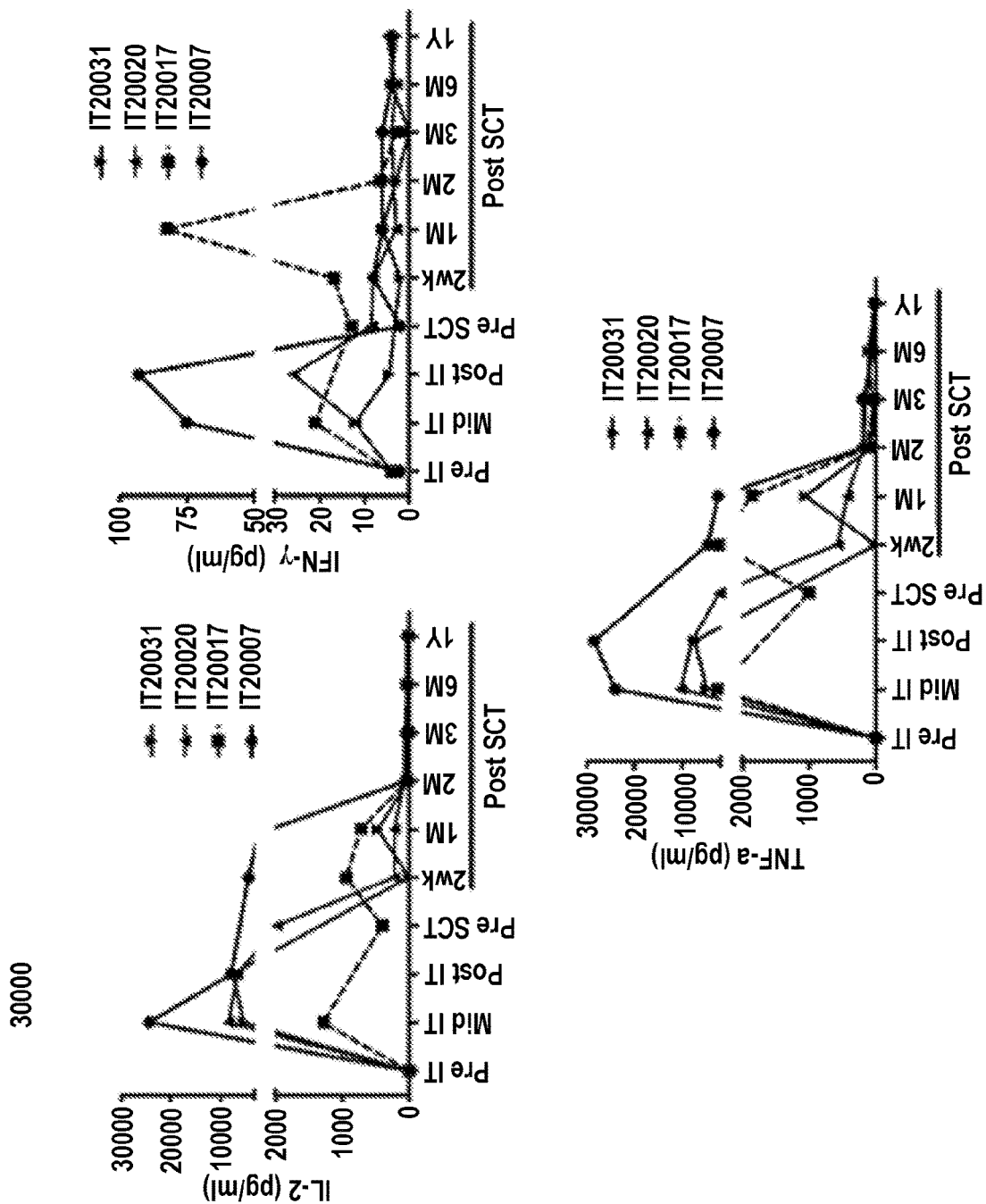
FIG. 3A shows an exemplary profile of serum cytokines. Analysis of serum samples (n=13) at pre-immunotherapy (Pre IT), mid IT, post IT and post SCT. Infusions of HER2 BATs induce increase in both type 1 cytokines IL-2, IFN-γ, TNF-α, IL-12, and type 2 cytokines IL-4, IL-6 and IL-10. Levels and remained high up to 2 months post SCT.
Figure 3A:
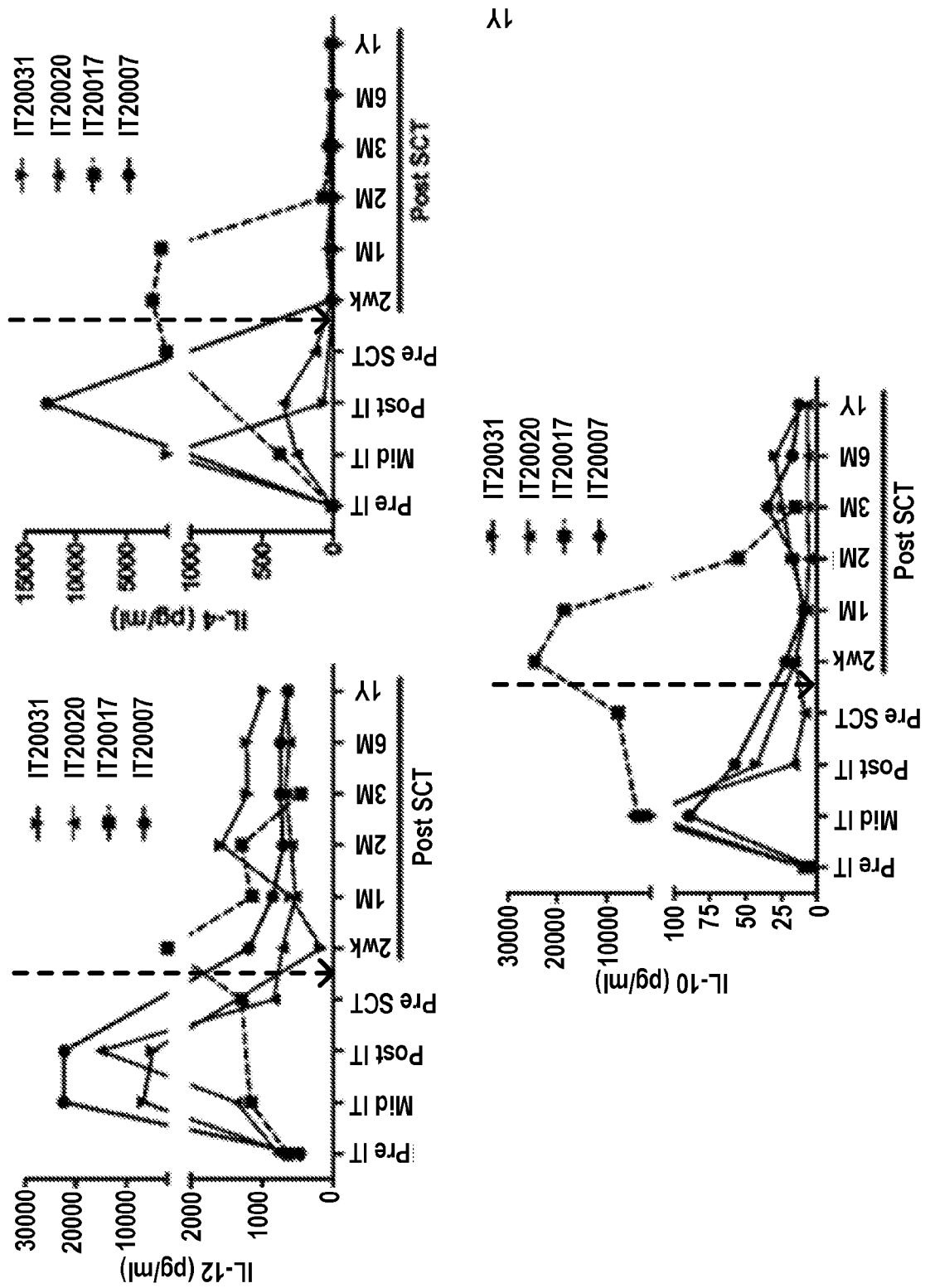

Immunokine levels were detected in 4 of 6 patients. $Th_1$ (IL-2, TNF-α, IFN-γ) and Th2 cytokines (IL-4 and IL-10) increased sharply from baseline to post IT. After SCT, levels of IL-2, TNF-α, and IL-12 remained high up to 2 months (FIG. 3A).

Figure 3B:
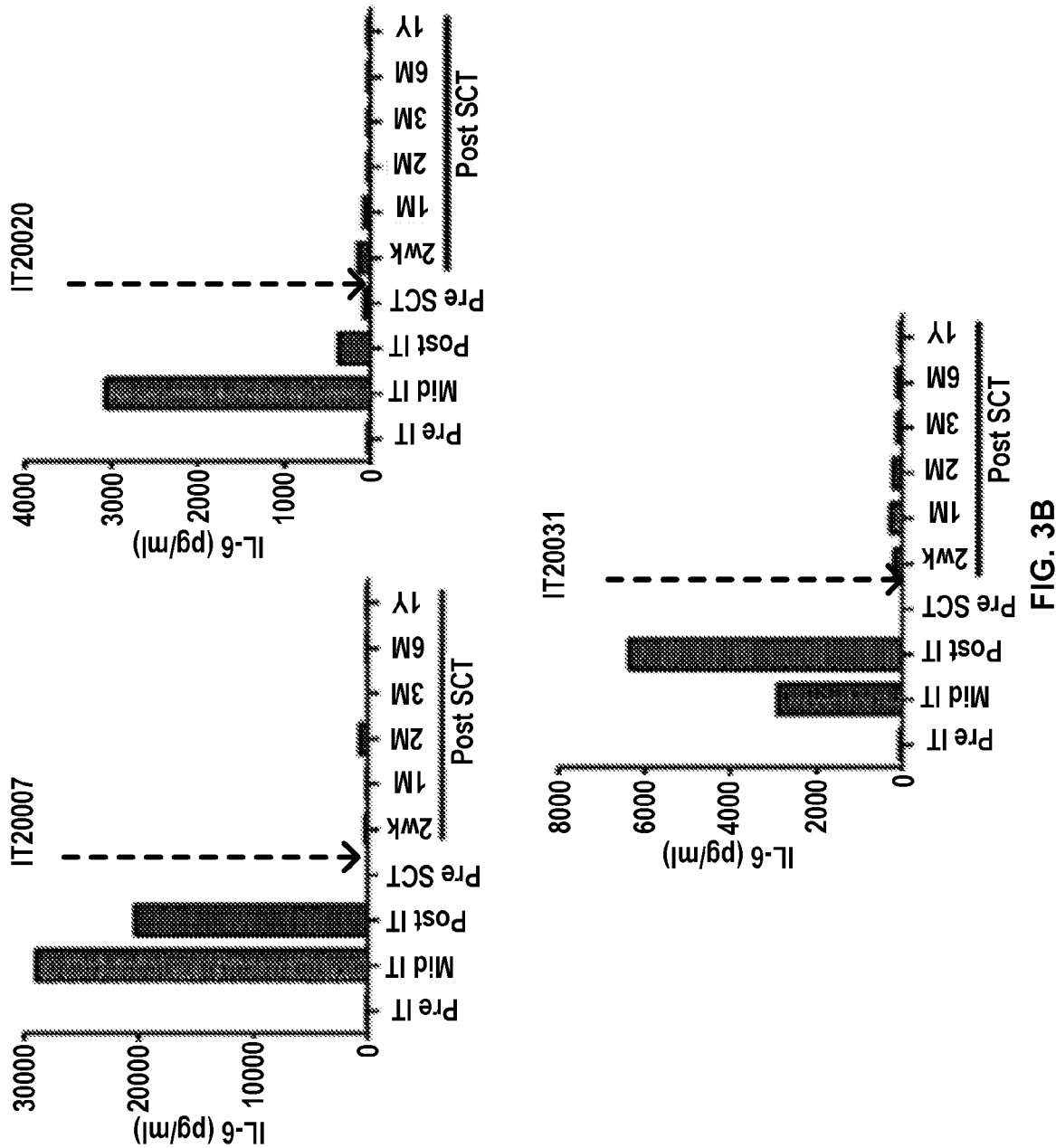
FIG. 3B shows an exemplary profile for IL-6 levels in 4 patients during IT and Post SCT. It is noteworthy that one patient (IT2017) who had rapid progression of disease had high levels of not only IL-6 but also the IL-4 and IL-10.

MIP-1β and IFN-γ-induced chemokines IP-10 and MIG (FIG. 3B cont'd) showed the same pattern after IT and levels decreased to near baseline by 2 months except for IT20017 (dotted line). The Type 1/Type 2 cytokines ratio shifted towards anti-tumor Type 1 cytokine profile during therapy.

Figure 3C:
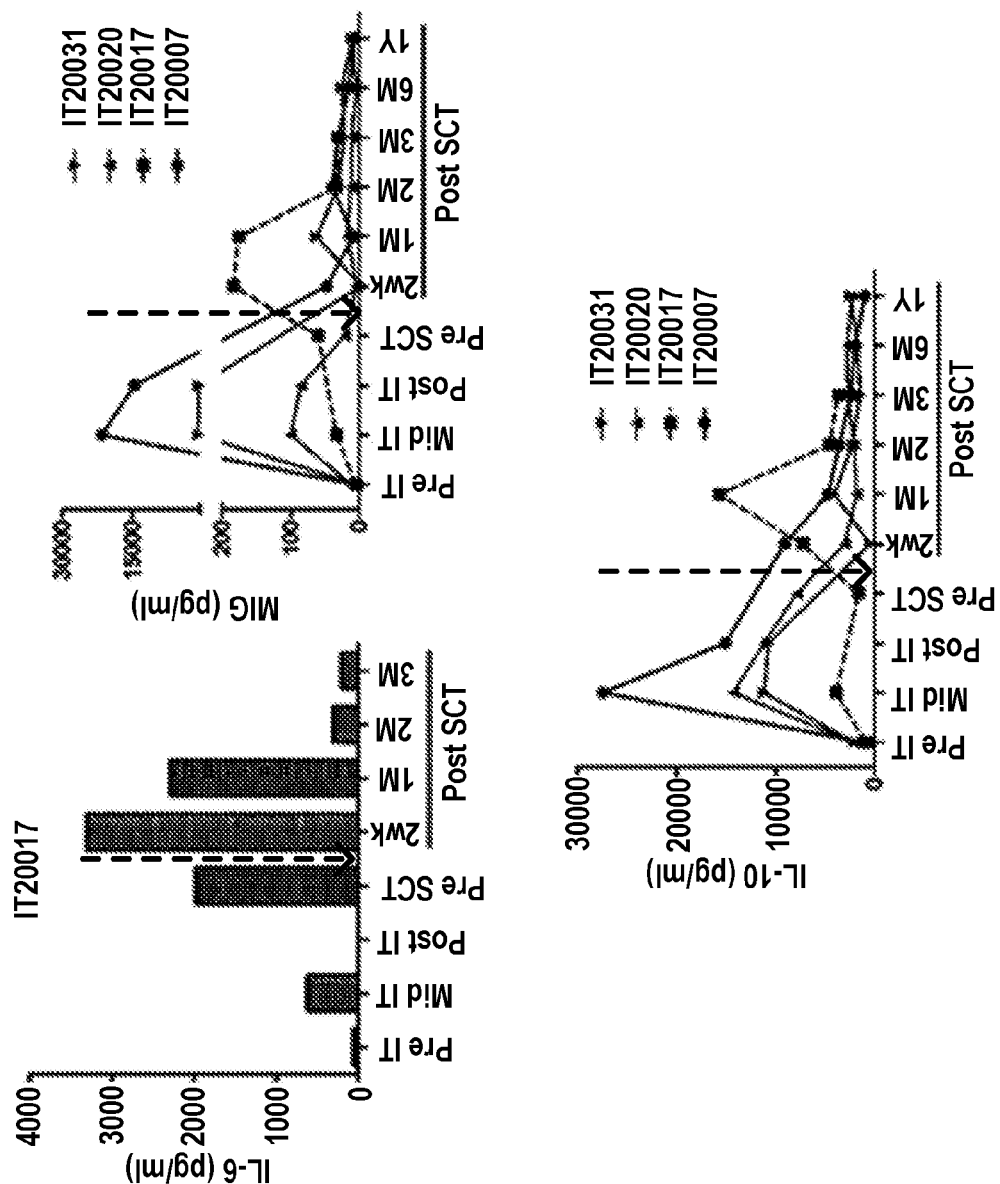
FIG. 3C shows an exemplary chemokine profile at Pre IT, mid IT, post IT and multiple time points post SCT for MIG, IP-10 and MIP-1b). The last panel of FIG. 3C shows the mean ratio of $Th_1/Th_2=[IL-2+IFN\gamma]/[IL-4+IL-10]$ at pre-, mid-post-IT and multiple time points post SCT.
Figure 7:
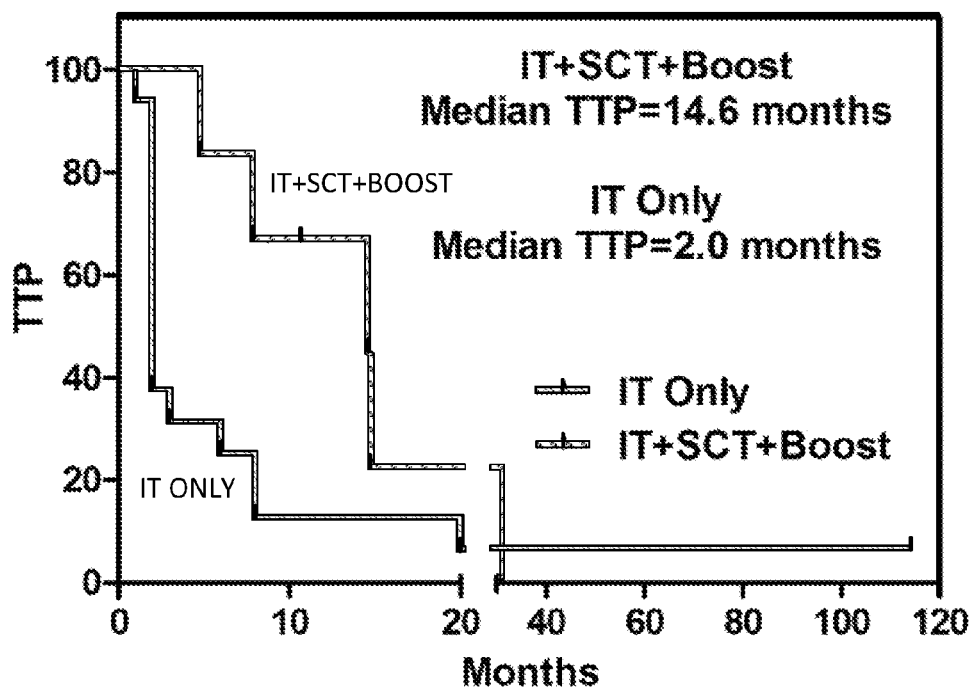
FIG. 7 Shows K-M curve for time to progression (TTP) for patients who received BATs infusions only compared those who received BATs infusions followed by SCT and Boost (as indicated).
Figure 8:
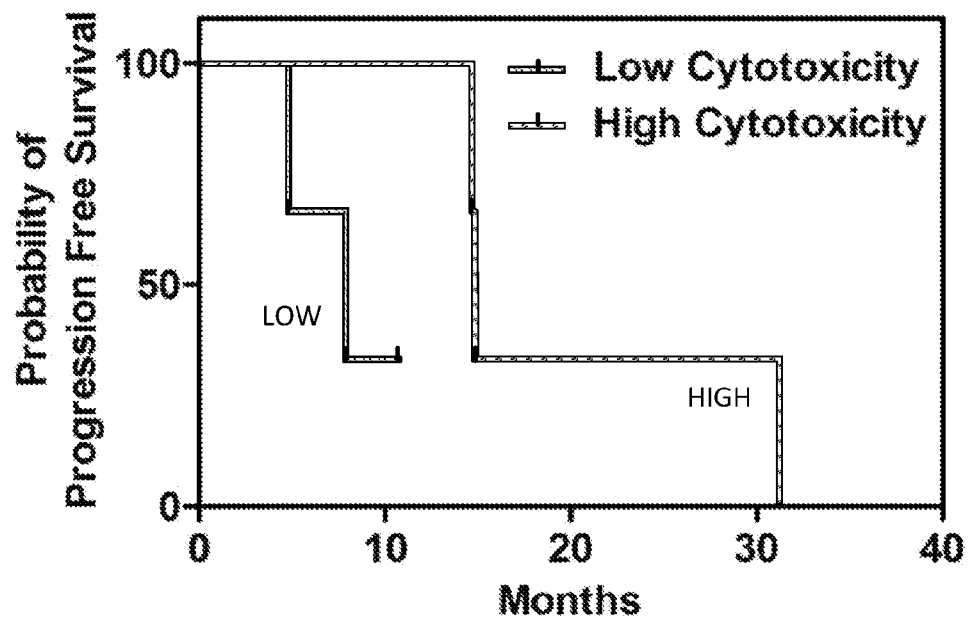
FIG. 8 shows K-M curve for probability of progression free survival for patients whose BATs exhibited high specific cytotoxicity versus those with low specific cytotoxicity. Low cytotoxicity shown in the red line and high cytotoxicity is shown in the blue line (as indicated).

IL-6 levels (FIG. 3B) which were high pre SCT disappeared post SCT in 3 patients (IT20007, IT20020 and IT20031) who were stable for 6 months or more post SCT. Patient IT20017 (dotted line in FIGS. 3A-3C) who progressed stood out with elevated levels of IL-6, IL-4, and IL-10 post SCT.

Vβ Repertoire Pattern Post SCT Mirrored Post BATs Infusion Pattern

The T cell repertoire develops during thymic selection (Starr et al., Positive and negative selection of T cells. *Annu Rev Immunol.* 2003; 21:139-76) with V13 specificity determined by variable-beta (Vβ) and -alpha (Vα) chains (Richman et al., Structural features of T cell receptor variable regions that enhance domain stability and enable expression as single-chain ValphaVbeta fragments. *Mol Immunol.* 2009 February; 46(5):902-16) and by post-thymic expansion (Pannetier et al., T-cell repertoire diversity and clonal expansions in normal and clinical samples. *Immunol Today*, 1995; 16:176-81) We determined the frequency of CD3+ cells expressing 24 TCR V1 chains after infusions of BATs.

Analysis of the T cell repertoire (FIG. 2B cont'd) shows Vβ chain expression in one patient (IT20007) after BATS infusion and after SCT compared to a normal donor (ND). There were three major patterns of V3 expression observed:

(1) The proportions of Vβ expression are similar in 17 of 24 V13 repertoire post BATs infusion and post SCT relative to a ND (group 1);

(2) The proportions that were high after BATs infusion and remained high post SCT (Vβ2, Vβ14, and Vβ22) relative to a ND (group 2); and (3) The proportions that were high after BATs infusion and decreased to NS levels post SCT (Vβ9, Vβ13.6, Vβ18, and Vβ23) (group 3).

The proportion V37.1 was low after BATs infusion and recovered to ND levels after SCT. Further, we determined the frequency of IFN-γ expressing CD4+ and CD8+Vβ repertoires in ATC expanded from immune PBMC after stimulation with breast cancer cells.

Figure 2B:
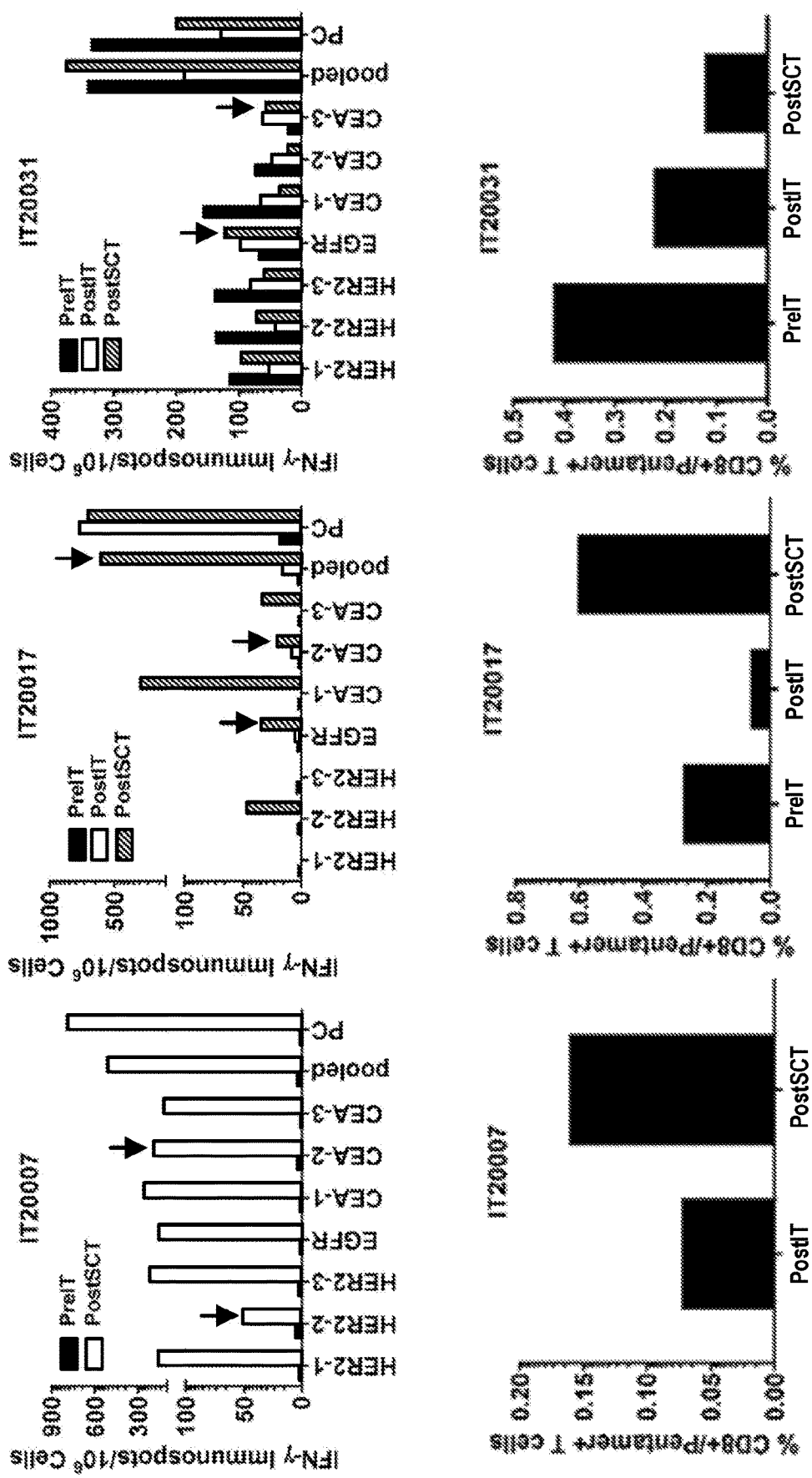
FIG. 2B shows the epitope-specific T-cell responses.
Figure 2B:
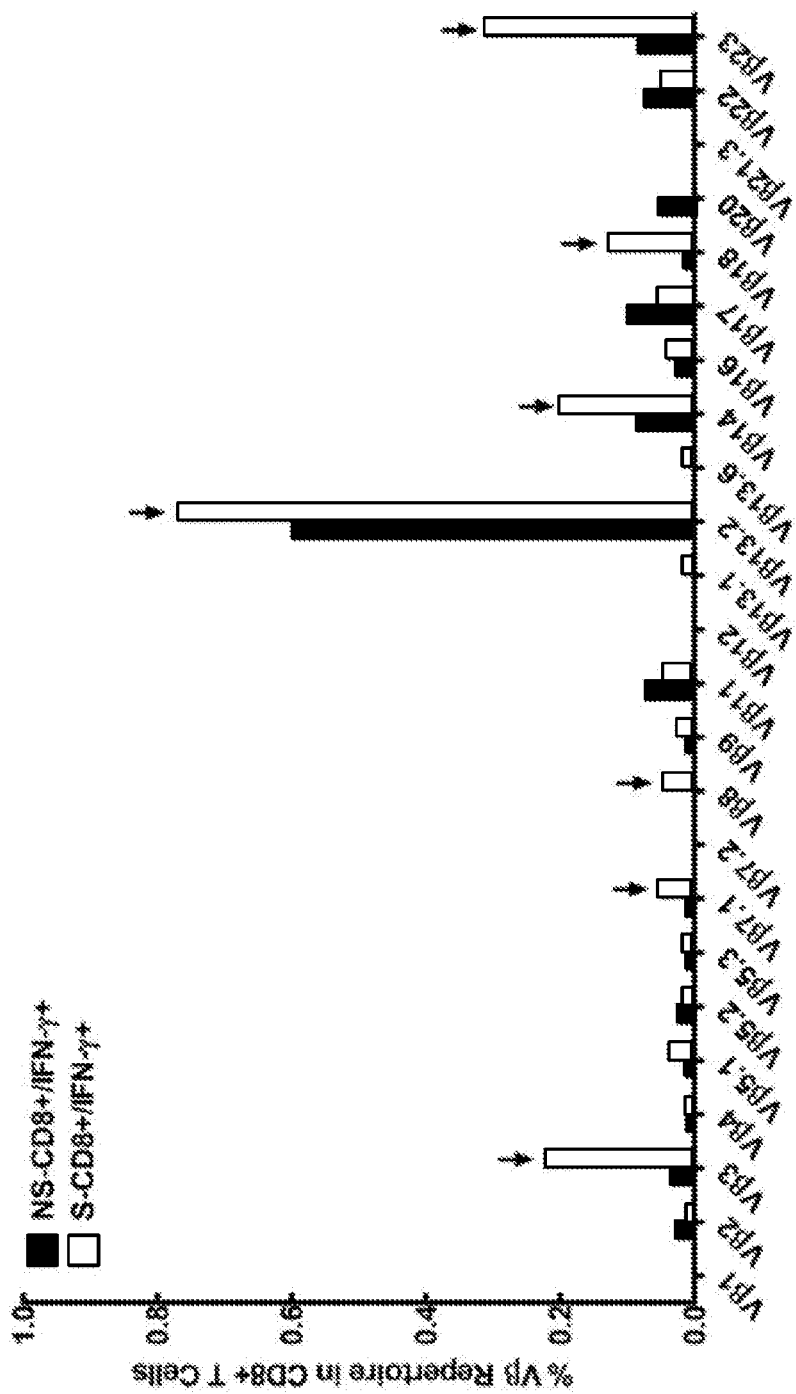
Figure 2B:
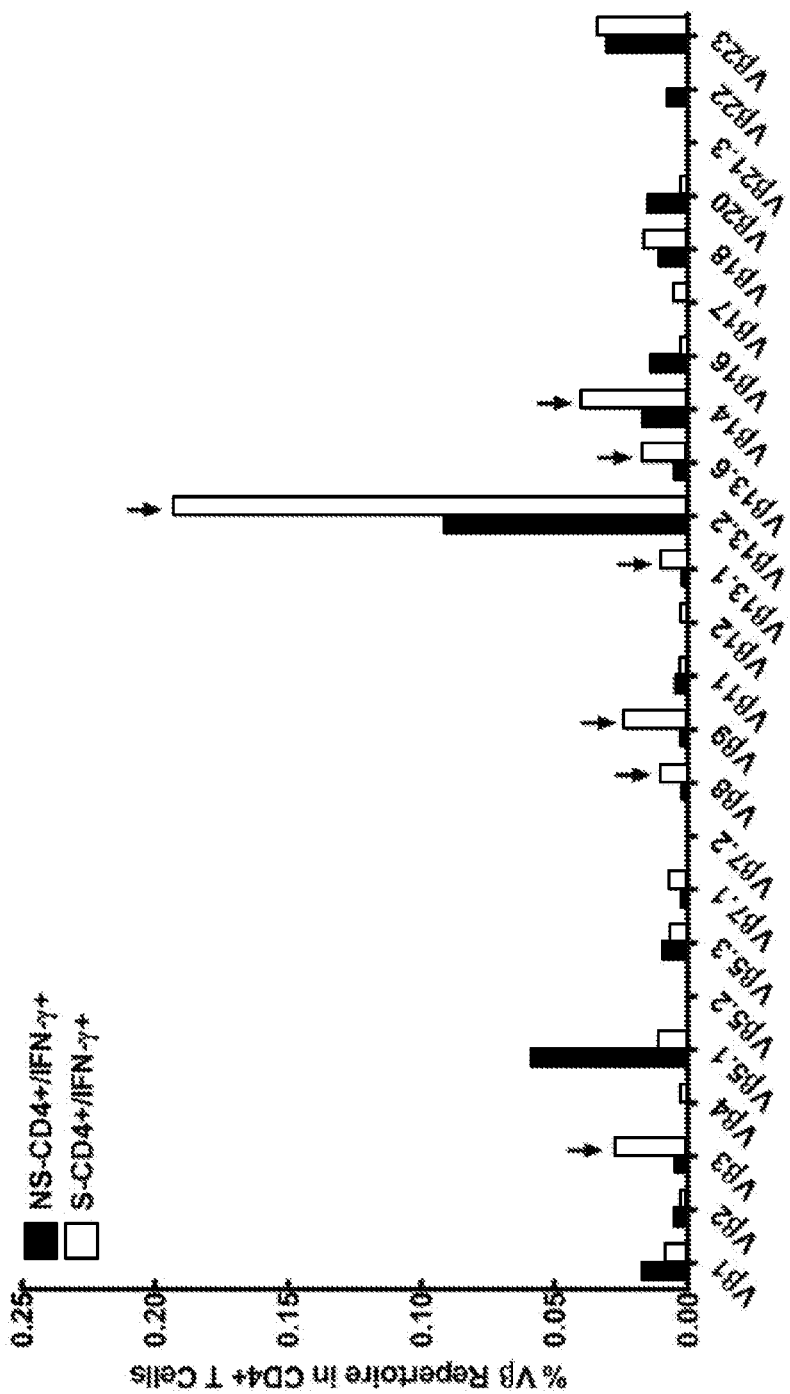
Figure 2B:
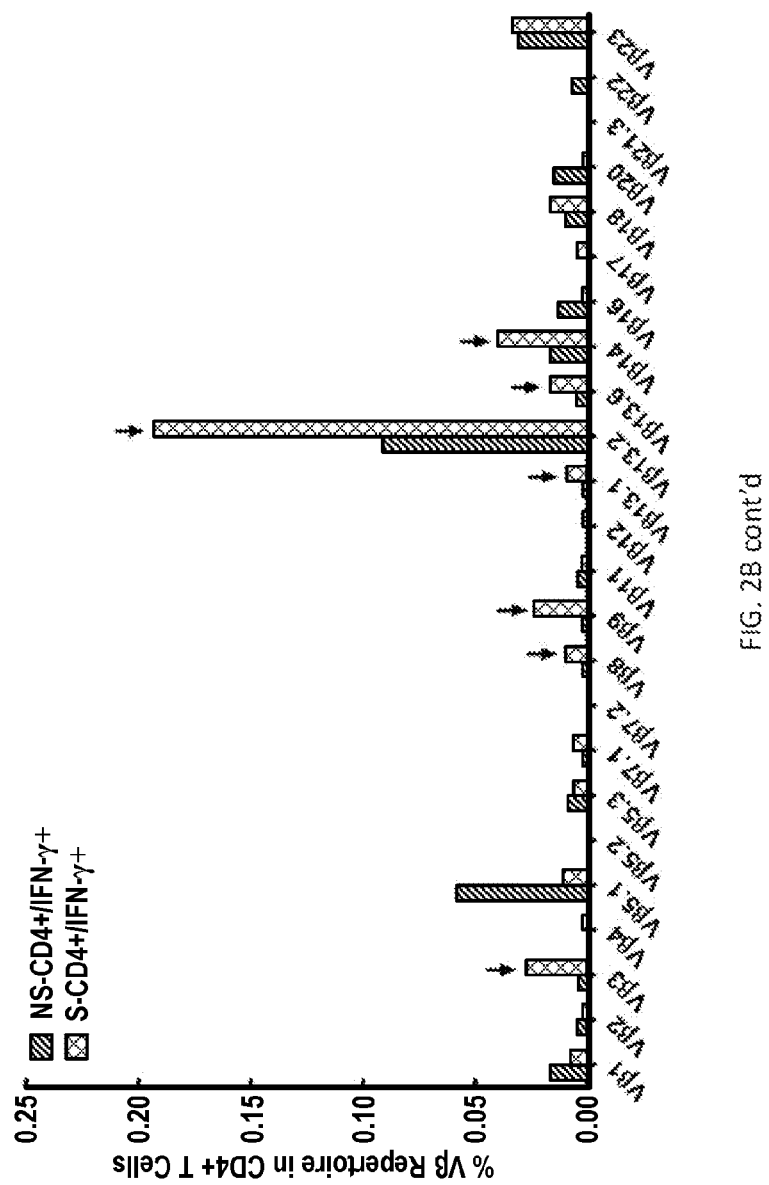
Figure 2B:
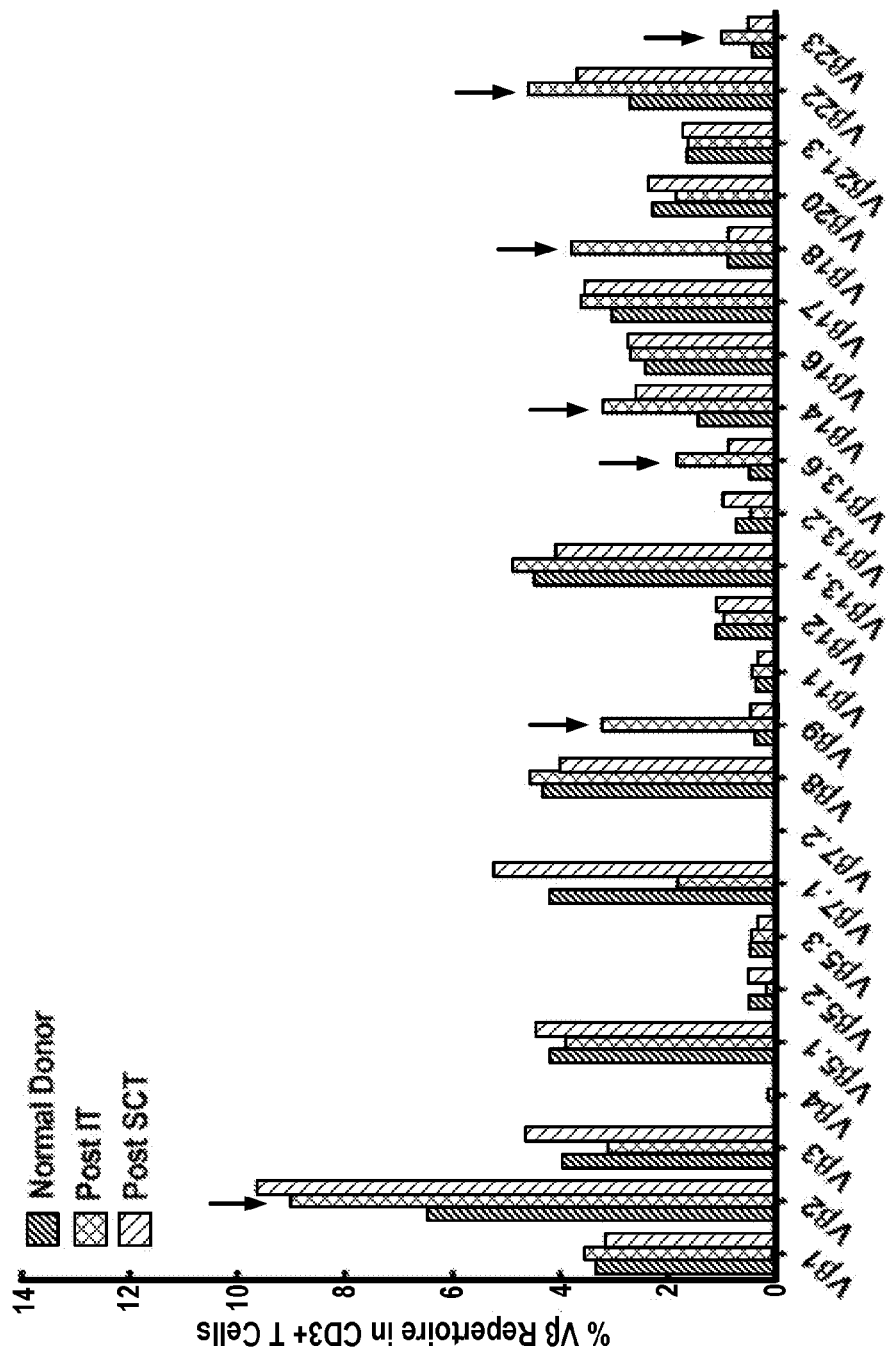
Figure 2B:
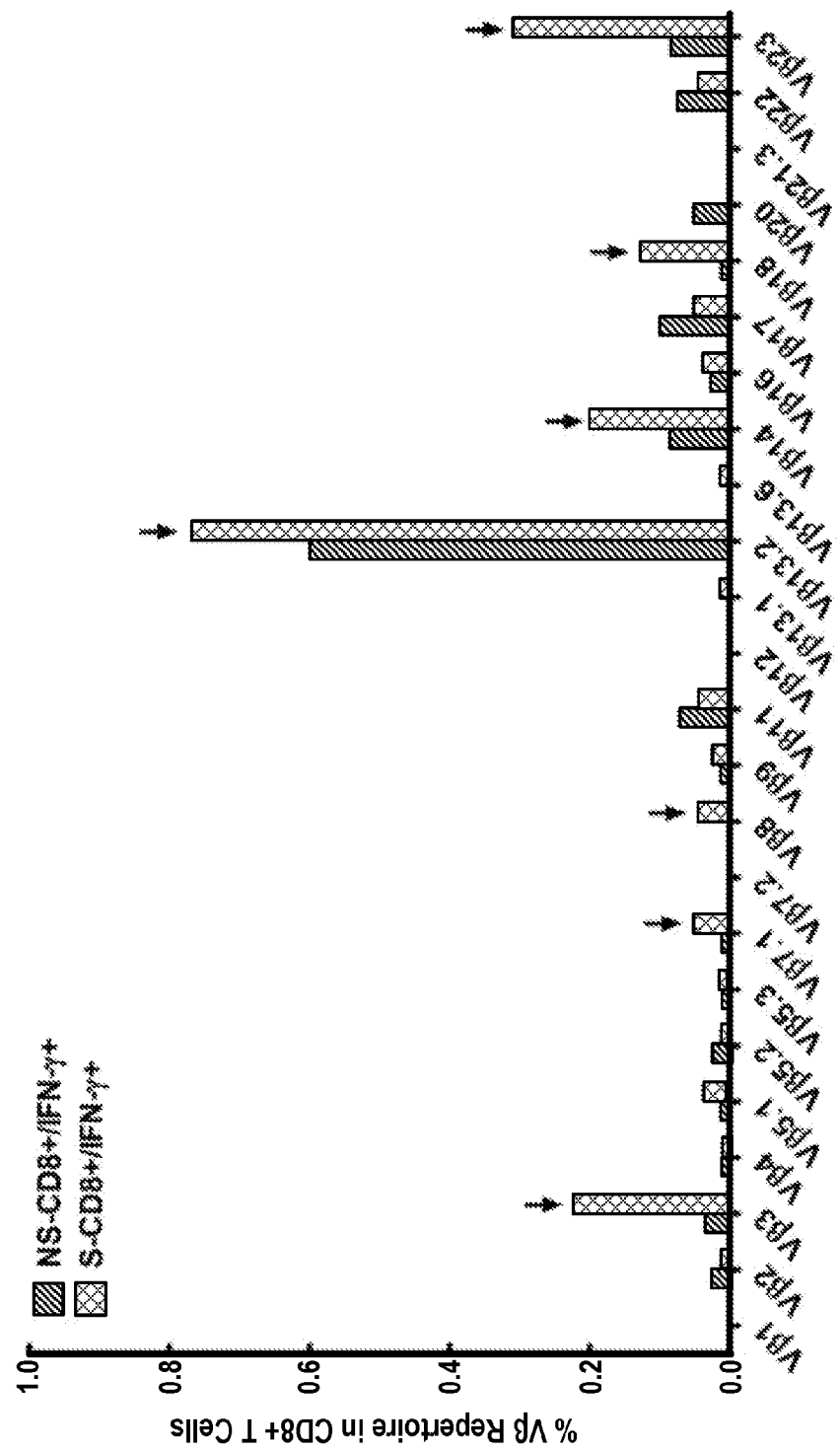
Figure 2C:
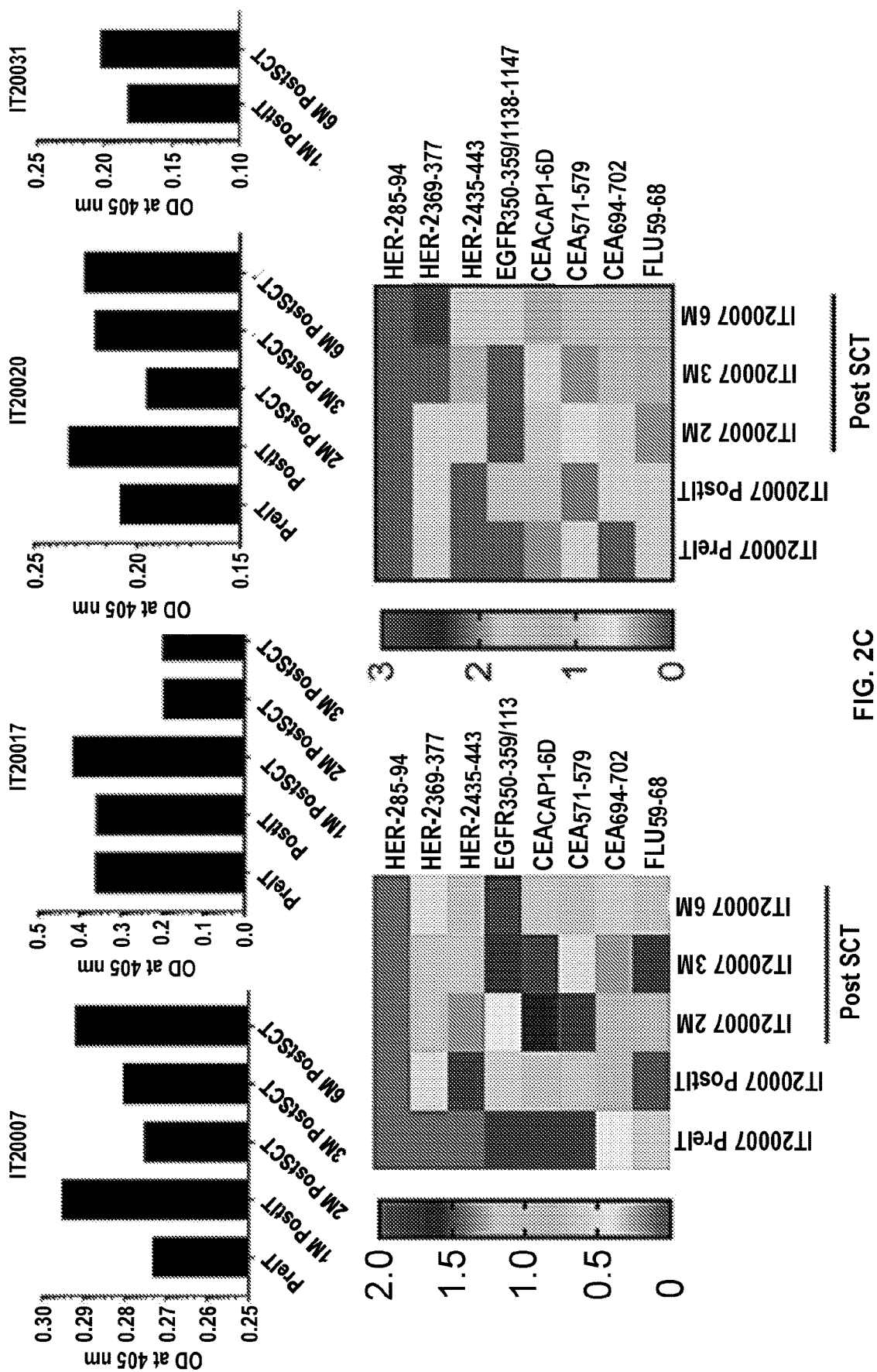
FIG. 2C shows epitope-specific B-cell responses.
Figure 2C:
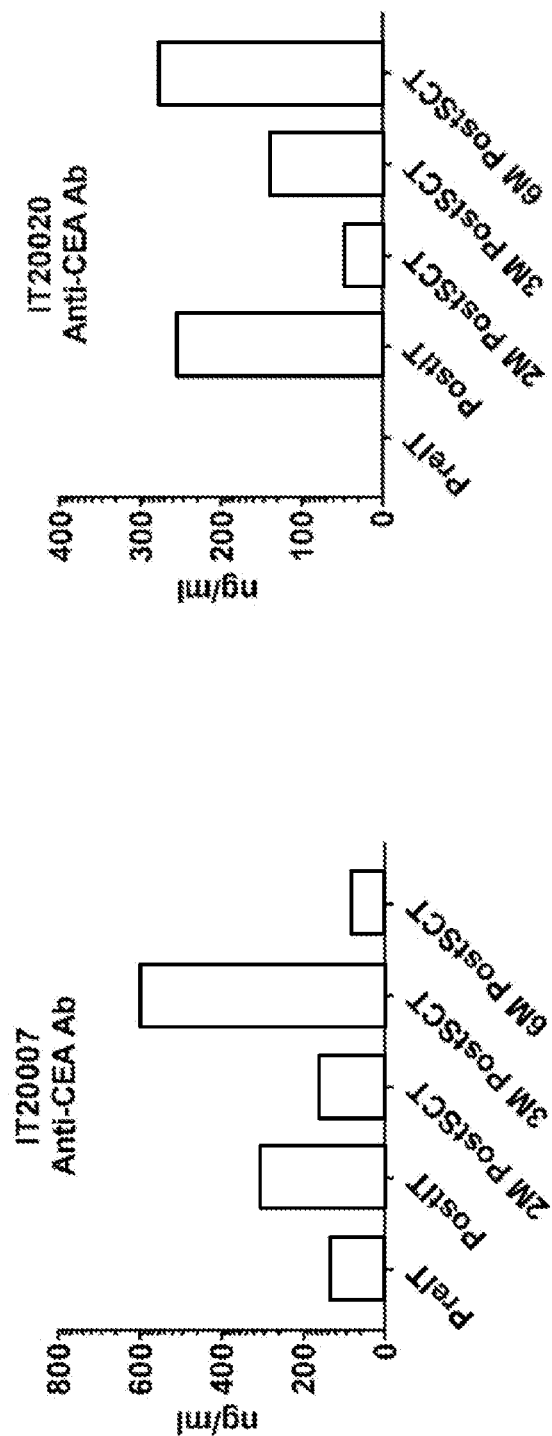

Intriguingly, 10/24 CD4+ and/or CD8+ clones (Vβ3, Vβ7.1, Vβ8, Vβ9, Vβ13.1, Vβ13.2, Vβ13.6, Vβ14, Vβ18, and Vβ23 chains) produced IFN-γ upon stimulation with breast cancer cells (SK-BR-3) providing validation that BATs induced breast cancer specific T cell clones that were transferred after SCT and persisted in the patient up to 1 year post SCT (see, FIG. 2B cont'd).

Discussion

This is the first study that reports that anti-tumor immunity in T and B cells induced by BATs infusions can be adoptively transferred after SCT to enhance anti-tumor immunity in MBC patients.

In our earlier phase I study in women with MBC (see, Lum L G. Immunotherapy with Activated T Cells after High Dose Chemotherapy and PBSCT for Breast Cancer. In: Dicke K A, Keating A (eds). Carden Jennings: Charlottesville, N Y, 2000, pp 95-105) infusions of unprimed ATC after high dose chemotherapy (HDC) and stem cell transplant (SCT) suggested that unprimed ATC can accelerate the reconstitution of anti-tumor responses by providing polyclonal helper, CTL, and LAK-like cytotoxicity after lymphodepletion. (Curti et al. Treatment of cancer patients with ex vivo anti-CD3-activated killer cells and interleukin-2. *J. Clin. Oncol,* 11:652-660 (1993) and Curti et al. Phase I trial of anti-CD3-stimulated CD4+ T cells, infusional interleukin-2, and cyclophosphamide in patients with advanced cancer. *J. Clin. Oncol.,* 16: 2752-2760 (1998)).

This study uses a "vaccination" with BATs and "boost" with ex vivo expanded immune ATC after SCT to maximize anti-tumor immune activity. HDC was used to create immune space by depleting T regulatory cells and myeloid derived suppressor cells. The "boost" infusions of cultured activated T cells permitted the immune cells to expand after transfer and accelerated reconstitution of anti-tumor T and B cell responses.

All 4 patients tested for immune studies, exhibited non-MHC restricted cytotoxicity and tumor specific IFN-γ EliSpots by PBMC obtained after SCT. These data show that the transferred tumor-specific immune responses were mediated by endogenous immune cells (See, Lum L G, Thakur A, Al-Kadhimi Z, Colvin G A, Cummings F J, Legare R D, et al. Targeted T-cell Therapy in Stage IV Breast Cancer: A Phase I Clinical Trial. *Clin Cancer Res* 2015, 21(10): 2305-2314 and Grabert R C, Cousens L P, Smith J A, Olson S, Gall J, Young W B, et al. Human T cells armed with Her2/neu bispecific antibodies divide, are cytotoxic, and secrete cytokines with repeated stimulation. *Clin Cancer Res* 2006, 12(2): 569-576)

Our findings are consistent with earlier studies showing that adoptive transfer of vaccine-primed and anti-CD3/anti-CD28 co-stimulated T cells boosts cellular and humoral responses to tumor antigens after SCT for multiple myeloma. (See, Stadtmauer E A, Vogl D T, Luning P E, Boyer J, Aqui N A, Rapoport A P. et al. Transfer of influenza vaccine-primed costimulated autologous T cells after stem cell transplantation for multiple myeloma leads to reconstitution of influenza immunity: results of a randomized clinical trial. *Blood,* 2011, 117(1): 63-71; Rapoport A P, Aqui N A, Stadtmauer E A, Vogl D T, Fang H B, Cai L, et al. Combination immunotherapy using adoptive T-cell transfer and tumor antigen vaccination on the basis of hTERT and survivin after ASCT for myeloma. *Blood,* 2011, 117(3): 788-797 and Rapoport et al. Restoration of immunity in lymphopenic individuals with cancer by vaccination and adoptive T-cell transfer. *Nat. Med,* 2005, 11(11): 1230-1237).

However, unlike the results of Rapoport et al (2011), the use of BATs to vaccinate cancer patients is shown here to generate anti-tumor humoral, cellular and natural immunity, including non-MHC restricted cytotoxic responses, leading to unique clinical benefits. The levels of immune ATC cytotoxicity against tumor cell lines correlates with clinical improvement in TTP, as opposed to what was found in myeloma patients vaccinated with tumor-associated peptides. As shown by Rapoport, despite the induction of tetramer-specific T cells for HLA-A2 restricted tumor peptides, those patients did not show a difference in event-free survival relative to non-vaccinated HLA A2-negative patients.

Thus, "vaccinating" with multiple infusions of anti-tumor activated T cells provides a unique clinical advantage due to the type of anti-tumor immune response induced that can be subsequently transferred to "boost" the anti-tumor responses in patients.

Notably, there were no dose limiting toxicities (DLT) in patients given BATs or ATC after SCT. One patient developed sepsis after SCT. She fully recovered and is alive at 61 months from enrollment for BATs (IT 20031). The absolute lymphocyte counts recovered to 500/mm$^3$ between 8 and 17 days after SCT without lymphocytosis, cytokine storm or impairment of neutrophil engraftment after SCT. Additionally, no dose limiting toxicities were obtained for patients who did not receive IL-2 and GM-CSF treatment.

The immediate killing exhibited by fresh PBMC from patients directed at allogeneic SK-BR-3 cells shows non-MHC restricted cytotoxicity mediated by in vivo primed T cells (See, Simpson-Abelson et al IL-12 delivered intratumorally by multilamellar liposomes reactivates memory T cells in human tumor microenvironments. *Clin Immunol* 2009, 132(1): 71-82). The CTL activity persisted up to 2 years after SCT.

Since fresh PBMC and ATC expanded from the PBMC before infusions of BATs did not exhibit high levels of anti-BrCa CTL activity, the post IT and post SCT responses are most likely to be due to the infusions of BATs.

Patients IT20007 and IT20031 had robust CTL and IFN-γ responses detected at 2 weeks after SCT. Serum anti-BrCa antibody reached levels comparable to pre SCT levels within 2-3 months after SCT in all 4 patients. Antibody synthesis after SCT gradually increased after IT (Thakur et al., Induction of specific cellular and humoral responses against renal cell carcinoma after combination therapy with cryoablation and granulocyte-macrophage colony stimulating factor: A pilot study. *Journal of Immunotherapy,* 34(5):457 (2011)).

For specific antibody production to be detected, immune B cells not only have to be present but they had to be transferred in the stem cell product. The transfer of immune T and B cells in the stem cell product is not likely to be sufficient to provide the robust CTL activity detected 2-4 weeks after SCT since there are intrinsic T and B cell defects in the first 3 months after SCT (See, Lum L G. Review: The kinetics of immunologic recovery after human marrow transplantation. *Blood* 1987, 69:369-380). In vitro antibody synthesis and circulating antibodies to breast cancer detected in the first 3 months after SCT show that "boosting" with immune ATC can provide antigen specific helper and CTL activity that not only overcomes the T and B cell defects seen in the first 3 months after SCT (see, Witherspoon R P, Lum L G, Storb R, Thomas E D. In vitro regulation of immunoglobulin synthesis after human marrow transplantation. II. Deficient T and non-T lymphocyte function within 3-4 months of allogeneic, syngeneic, or autologous marrow grafting for hematologic malignancy. Blood 59:844-850 (1982); Wahren et al. Transfer and persistence of viral antibody-producing cells in bone marrow transplantation. *J. Infect. Dis.,* 150:358-365 (1984); Matsue et al., Proliferative and differentiative responses of B cells from human marrow graft recipients to T cell-derived factors. *Blood,* 69:308-315 (1987); Lum et al., The transfer of antigen-specific humoral immunity from marrow donors to marrow recipients. *J. Clin. Immunol* 1986, 6:389-396; Stevens and Saxon, Immunoregulation in humans. Control of anti-tetanus toxoid antibody production after booster immunization. *J. Clin. Invest.* 1978, 62:1154-1160 and Saxon et al., Designed transfer of specific immune responses with bone marrow transplantation. *J. Clin. Invest.* 1986, 78:959-967) but also augments the transfer and persistence of the anti-tumor immunity for up to 2 years.

As demonstrated herein NK activity, which was low prior to IT, was remarkably increased after IT and persisted after SCT (FIG. 1B, top panel).

The predominant Vβ3 clones expand in vivo after BATs infusions and resurfaced as the dominant clonotypes in the patient PBMC post SCT as a result of transfer of immunity via stem cell product and/or boost using immune ATC. The group 1 TCR pattern shows transfer and persistence of most pre-existing Vβ clones. The higher proportions of group 2 TCR clones (Vβ2, Vβ14, and Vβ22) provide evidence for expansion induced by IT, transfer, and persistence. In contrast, group 3 TCR clones (Vβ9, Vβ13.6, Vβ18, and Vβ23) may have expanded after IT but did not persist.

A significant correlation (r=1.0; p<0.002) (See, FIG. 1C) between immune ATC cytotoxicity directed at breast cancer cells and TTP strongly suggests that more robust vaccinations with a Th$_1$ shift in cytokine profiles can lead to clinical benefit.

Importantly, as demonstrated herein, there were no detrimental differences observed in clinical responses for patients who did not receive IL-2 and GM-CSF treatments as compared to patients who did receive the cytokines. In fact, FIG. 1C shows 2 of the 4 patients (IT20007 and IT20020) who did not receive IL-2 and GM-CSF treatments, outperforming all patients who received IL-2 and GM-CSF treatments. Similarly, the TTP was also improved in the same 2 patients (IT20007 and IT20020) who did not receive IL-2 and GM-CSF treatments as compared to all patients who received the IL-2 and GM-CSF treatments. Accordingly, it appears that the IL-2 and GM-CSF treatments had a negative effect on the cancer patients as evidence by both the cytotoxicity and time to progression data (See, FIG. 1C).

The toxic effects of IL-2 and GM-CSF treatment regimens are well known and thus the above data suggests that the treatment of breast cancer patients with these cytokines provided no observable benefit. In addition to the serious and life threatening toxicities reported for IL-2 and GM-CSF treatments, the cost of treating cancer patients with these drugs is currently estimated at approximately $18,000 per patient. The removal of IL-2 and/or GM-CSF treatments from cancer treatment regimens according to the methods provided herein, would therefore provide a substantial cost-savings and health benefit to cancer patients.

In summary, this study shows that BATs induced endogenous anti-breast cancer cellular, humoral and innate immunity that could be detected after SCT and provided clinically meaningful anti-tumor immunity. There was robust reconstitution of T and B cell functions early after SCT as evidenced by CTL and NK activity, IFN-γ EliSpots, in vivo/in vitro antibody synthesis, and Th$_1$ cytokine responses. Furthermore, these responses persisted up to 2 years after SCT. The data also shows that no beneficial effect was observed for the treatment of cancer patients with IL-2 and GM-CSF. Thus, elimination of these drugs from immunotherapy regimens set forth herein would provide a significant cost savings and improved cytotoxicity and Time To Progression for patients who do not receive IL-2 and GM-CSF treatments.

Example 2: Novel Effects of Anti-Tumor T Cells in the Vaccination Phase

Many methods of therapeutic vaccination are available, e.g., peptide vaccines, dendritic cells pulsed with peptides or tumor lysates, viral vectors, DNA-based vectors, modified tumor cells expressing GM-CSF (GVAX), among others. Clinical results from therapeutic tumor vaccines are highly variable, with Provenge (sipuleucel-T) being the only FDA approved vaccine in the US to treat cancer.

Patient responses to peptide vaccines demonstrate the ability to induce antigen-specific T cell reponses, but clinical outcomes have been highly variable and unpredictable. Among the many variables affecting clinical outcome, the tumor microenvironment (TME) plays a prominent role in determining efficacy of a given immune response.

As shown herein, multiple infusions of BATS are capable of promoting broad endogenous anti-tumor immune responses consisting of antibodies, natural killer (NK) cells, and in particular "immune T cells". This effect requires multiple infusions to overcome the immunosuppressive nature of the tumor microenvironment. Although it has been demonstrated that adoptively transferred T cells become anergized by the TME (Moon et al., Multifactorial T cell hypofunction that is reversible can limit the efficacy of chimeric antibody receptor-transduced human T cells in solid tumors. *Clin. Cancer. Res* 20(16):4262-4273 (2014)), subsequent infusions seem to overcome TME-induced immune suppression resulting in more active T cells (as shown herein and Stromnes et al., T cells engineered against a native antigen can surmount immunologic and physical barriers to treat pancreatic ductal adenocarcinoma. *Cancer Cell,* 28(5):638-652 (2015)).

What has not been previously appreciated is the ability of multiple immune T cell infusions to promote endogenous anti-tumor humoral and cellular reponses, particularly the development of non-MHC-restricted T cell cytotoxicity. By recovering the endogeous immune T cells from peripheral blood, and expanding this population through in vitro activation, the activated T cells can be used to 'boost' patient immunity over time, with the level of cytotoxicity of immune ATC correlated with time to progression (shown herein).

However, not all methods of immunization prior to acquisition of immune T cells produce the same results. In a study of multiple myeloma patients, peptide vaccines for "universal" tumor antigens surviving and hTERT were administered to HLA-A2 positive patients prior to harvesting of peripheral blood T cells for co-activation and ex-vive expansion, and collection of autologous stem cells for transplanting post-myeloablation (Rapoport et al. Combination immunotherapy using adoptive T-cell transfer and tumor antigen vaccination on the basis of hTERT and survivin after ASCT for myeloma. *Blood*, 117(3): 788-797 (2011)). Patients were infused day 2 of transplantation with approximately $5 \times 10^{10}$ expanded T cells and monitored for event-free survival (EFS). Despite being able to generate hTERT/survivin tetramer positive T cells that proliferated in response to stimulation with hTERT/survivin peptides (i.e., demonstrating hTERT and surviving antigen specificity), there was no difference in EFS between the peptide vaccinated HLA-A2+ patients and HLA-A2 negative patients who did not receive the peptide vaccines. Therefore, the ability to induce immune T cells following BATS vaccination, followed by boosting post-SCT provides a unique clinical benefit as compared to the use of peptide vaccines using a similar approach.

Example 3: Methods for Treating Patients with Activated Anti-Tumor T Cells

In this example, an exemplary method to treat a cancer patient with activated anti-tumor T cells is described.

The first step involves infusing a cancer patient with activated anti-tumor T cells. The infusing step is performed at least once, preferably more than 3 times, and most preferably 8 or more times. Ideally, the total number of infusions of activated anti-tumor T cells to the cancer patient is less than 15 infusions. The infusions promote expansion of endogenous anti-tumor immune T cells in the cancer patient.

In the second step, the resulting immune T cells are collected by, e.g., leukapheresis, and activated ex vivo by methods available to those skilled in the art for use in a number of 'boost' infusions after lymphodepletion. As used herein, the term boost refers to administration of the expanded, cultured T cell population after lymphodepletion. Typically, the number of 'boost' injections is greater than 1, preferably greater than 3, and more preferably greater than 8 and fewer than or equal to 15 infusions.

After the immune T cells are collected, the cancer patient is treated to create immune space via lymphodeplateion. Lymphodepletion can be performed by high-dose chemotherapy and autologous stem cell transplant, or by less severe methods such as cytoxan, cytoxan plus flurdaribine, or cytoxan plus pentostatin (See, Kossman S E, Horgan D. Petostatin and cyclophosphamide: an effective new regimen in previously treated patients with chronic lymphocytic leukemia. *J Clin Oncol* 2003, 21: 1278-1284; Pavletic S Z, Bociek R G, Foran J M, Rubocki R J, Kuszynski C A, et al. Lymmphodepleting effects and safety of pentostatin for nonmyeloablative allogeneic stem-cell transplantation. *Transplantation* 2003, 76(5): 877-881; Turtle C J, Hanafi L-A, Berger C, Sommermeyer D, Pender B, Robinson, E M, et al. Addition of flydarabine to cyclophosphamide lymphodepletion improves in vivo expansion of CD19 chimeric antigen receptor-modified T cells and clinical outcome in adults with B cell acute lymphoblastic leukemia. *Blood* 2015, 126: 3773-3780 and Miller J S, Weisdorf D J, Burns L J, Slungaard A, Wagner J E, Verneris M R, Cooley S, et al. Lymphodepletion followed by donor lymphocyte infusion (DLI) causes significantly more acute graft-versus-host disease than DLI alone. *Blood* 2007, 110: 2761-2763), among other methods.

During the vaccination stage, multiple BATs infusions are available to activate preexisting chemoresistent lymphocytes as well as naïve T cells in the patient. Storek et al., demonstrated the recovery of a broad range of Vb usage by T cells obtained from patients who had received "lymphodepletive" conditioning followed by autolgous CD34 cell transplant (see, Storek J, Zhao Z, Liu Y, Nash R. McSweeney P, Maloney D G. Early recovery of CD4 T cellreceptor diversity after "lymphoablative" conditioning and autologous CD34 cell transplantation. *Biol. Blood Marrow Transplant*, 14(12):1373-1379 (2008)).

Evidence for the ability to induce and transfer anti-tumor T cell clones is provided by the patterns of TCR Vβ usage present in the pre-BATS and post-BATS infusion blood samples (see Vβ Repertoire Pattern Post SCT mirrored Post IT Pattern, described herein). Leukopheresis post-vaccination captures such anti-tumor lymphocytes, which are then expanded for boost infusions of immune ATC. In the 'boost' phase, non-myeloablative conditioning permits expansion of the anti-tumor donor lymphocytes capable of directly engaging tumor and further stimulating endogenous cellular and humoral responses. The process of the invention is a method to generate "systemic tumor infiltrating lymphocytes" as opposed to methods that require extensive in vitro stimulation and expansion of tumor infiltrating lymphocytes from tumor biopsies, or immunization with tumor cells followed by the isolation of lymph nodes and ex-vivo expansion (See, Chang A E, Li Q, Jiang G, Sayre D M, Braun T M, Redman B G. Phase II trial of autologous tumor vaccination, anti-CD3-activated vaccine-primed Ilymphocytes, and interleukin-2 in stage IV renal cell cancer 2003, *J. Clin. Oncol.*, 21:884-890). A further advantage of the present invention is in the nature of the immune response that not only includes transfer of novel T cell activity but anti-tumor humoral responses.

Example 4: Activated Anti-Tumor T Cells for Use in Stimulating Endogenous Patient Immunity As described herein, peripheral blood mononuclear cells obtained by leukapheresis were activated with anti-CD3 (OKT3) antibody and interleukin-2 and expanded in culture in the presence of IL-2. Other methods of obtaining activated anti-tumor T cells have been described and are commonly used clinically that can also be used to practice the invention. Other activated anti-tumor T cell types include, but are not limited to:

1. Bispecific antibody-armed autologous T cells activated with anti-CD3 antibody and IL-2 and cultured in IL-7 or IL-7+IL-15 (See, for example, Gargett T, Brown M P. Different cytokine and stimulation conditions influence the expansion and immune phenotype of third-generation chieric antigen receptor T cells specific for tumor antigen GD2. *Cytotherapy* 2015, 17(4):487-495; Caserta S, Alessi P, Basso V, Mondino A. 11-7 is superior to IL-2 for ex-vivo expansion of tumour-specific CD4+ T cells. *Eur J Immunol* 2010, 40:470-479; and Cha E, Graham L, Manjili M H, Bear H D. IL-7+IL-15 are superior to IL-2 for the ex-vovo expansion of 4T1 mammary carcinoma-specific T cells with greater efficiency against tumors in vivo. *Breast Cancer Res Treat* 2010, 122:359-369).

2. Bispecific antibody-armed autologous T cells co-activated with anti-CD3 and anti-CD28 antibodies (either in solution or particle bound) and cultured in IL-2, IL-7 or IL-7+IL-15;

3. Bispecific antibody-armed allogeneic T cells activated with anti-CD3 and IL2 and cultured in IL-2, IL-7 or IL-7+IL-15;

4. Bispecific antibody-armed allogeneic T cells activated with anti-CD3 and anti-CD28 (either in solution or particle bound) and cultured in IL-2, 11-7 or IL-7+IL-15:

5. Chimeric antigen receptor engineered T cells (CAR-T);

6. T cell receptor engineered T cells (TCR therapies);

7. Tumor-infiltrating lymphocytes (TIL); and

8. Bispecific antibody-armed T-Rapa cells (See, for example, Fowler D H, Mossoba M E, Steinberg S M, Halverson D C, Stroncek D, Khuu, H M, et. al. Phase 2 clinical trial of rapamycin-resistant donor CD4+Th2; Th$_1$ (T-Rapa) cells after low-intensity allogeneic hematopoietic cell transplantation. *Blood* 2013, 121(15):2864-2874).

Example 5: Activated Immune T Cells for Use in Boost Infusions

After collecting immune T cells post-vaccination phase, T cells can be activated by any methods available in the art, including but not limited to:

1. Activation with anti-CD3 antibody and IL-2 (see, Lum L G, thakur A, Al-Kadhimmi Z, Colvin G A, Cummings F J, Legare R D, Dizon D S, Kouttab N, Maizel A, Colaiace W, Liu Q, Rathore R Targeted T-cell therapy in stage IV breast cancer: a phase I clinical trial. *Clin Cancer Res* 2015, 21(10): 2305-2314);

2. Co-activation with anti-CD3 and anti-CD28 antibodies (both in solution or particle bound) and cultured in IL-2, IL-7 or IL-7+IL-15; and 3. Co-activation with anti-CD3 and anti-CD28 antibody conjugated beads plus rapamycin (See, Fowler D H, Mossoba M E, Steinberg S M, Halverson D C, Stroncek D, Khuu, H M, et. al. Phase 2 clinical trial of rapamycin-resistant donor CD4+Th2/Th1 (T-Rapa) cells after low-intensity allogeneic hematopoietic cell transplantation. *Blood* 2013, 121(15):2864-2874).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

The following references are herein incorporated in their entirety.

Sen M, Wankowski D M, Garlie N K, Siebenlist R E, Van Epps D, LeFever A V, et al. Use of anti-CD3×anti-HER2/neu bispecific antibody for redirecting cytotoxicity of activated T cells toward HER2/neu+ tumors. *J Hematother Stem Cell Res* 2001, 10(2): 247-260.

Lum L G, Thakur A, Al-Kadhimi Z, Colvin G A, Cummings F J, Legare R D, et al. Targeted T-cell Therapy in Stage I V Breast Cancer: A Phase I Clinical Trial. *Clin Cancer Res* 2015, 21(10): 2305-2314.

Lum L G. Immunotherapy with Activated T Cells after High Dose Chemotherapy and PBSCT for Breast Cancer. In: Dicke K A, Keating A (eds). Carden Jennings: Charlottesville, N Y, 2000, pp 95-105.

Berry D A, Ueno N T, Johnson M M, Lei X, Caputo J, Rodenhuis S, et al. High-dose chemotherapy with autologous stem-cell support as adjuvant therapy in breast cancer: overview of 15 randomized trials. *J Clin Oncol* 2011, 29(24): 3214-3223.

Gall J M, Davol P A, Grabert R C, Deaver M, Lum L G. T cells armed with anti-CD3×anti-CD20 bispecific antibody enhance killing of CD20+ malignant B-cells and bypass complement-mediated Rituximab-resistance in vitro. *Exp Hematol* 2005, 33(4): 452-459.

Grabert R C, Cousens L P, Smith J A, Olson S, Gall J, Young W B. et al. Human T cells armed with Her2/neu bispecific antibodies divide, are cytotoxic, and secrete cytokines with repeated stimulation. *Clin Cancer Res* 2006, 12(2): 569-576.

Lum L G, Culbertson N J. The induction and suppression of in vitro IgG anti-tetanus toxoid antibody synthesis by human lymphocytes stimulated with tetanus toxoid in the absence of in vivo booster immunizations. *J Immunol* 1985, 135: 185-191.

Thakur A, Norkina O, Lum L G. In vitro synthesis of primary specific anti-breast cancer antibodies by normal human peripheral blood mononuclear cells. *Cancer Immunology, Immunotherapy* 2011, 60(12): 1707-1720.

Thakur A, Littrup P, Paul E N, Adam B, Heilbrun L K, Lum L G. Induction of specific cellular and humoral responses against renal cell carcinoma after combination therapy with cryoablation and granulocyte-macrophage colony stimulating factor: a pilot study. *Journal of Immunotherapy* 2011, 34(5): 457.

Simpson-Abelson M R, Purohit V S, Pang W M, Iyer V, Odunsi K, Demmy T L, et al. IL-12 delivered intratumorally by multilamellar liposomes reactivates memory T cells in human tumor microenvironments. *Clin Immunol* 2009, 132(1): 71-82.

Curti B D, Longo D L, Ochoa A C, Conlon K C, Smith J W, I I, Alvord W G, et al. Treatment of cancer patients with ex vivo anti-CD3-activated killer cells and interleukin-2. *J Clin Oncol* 1993, 11: 652-660.

Curti B D, Ochoa A C, Powers G C, Kopp W C, Alvord W G, Janik J E. et al. Phase I trial of anti-CD3-stimulated CD4+ T cells, infusional interleukin-2, and cyclophosphamide in patients with advanced cancer. *J Clin Oncol* 1998, 16: 2752-2760.

Stadtmauer E A, Vogl D T, Luning P E, Boyer J, Aqui N A, Rapoport A P, et al. Transfer of influenza vaccine-primed costimulated autologous T cells after stem cell transplantation for multiple myeloma leads to reconstitution of influenza immunity: results of a randomized clinical trial. *Blood* 2011, 117(1): 63-71.

Rapoport A P, Aqui N A, Stadtmauer E A, Vogl D T, Fang H B, Cai L, et al. Combination immunotherapy using adoptive T-cell transfer and tumor antigen vaccination on the basis of hTERT and survivin after ASCT for myeloma. *Blood* 2011, 117(3): 788-797.

Rapoport A P, Stadtmauer E A, Aqui N, Badros A, Cotte J, Chrisley L, et al. Restoration of immunity in lymphopenic individuals with cancer by vaccination and adoptive T-cell transfer. *Nat Med* 2005, 11(11): 1230-1237.

Lum L G. Review: The kinetics of immunologic recovery after human marrow transplantation. *Blood* 1987, 69: 369-380.

Witherspoon R P, Lum L G, Storb R, Thomas E D. In vitro regulation of immunoglobulin synthesis after human marrow transplantation. I I. Deficient T and non-T lymphocyte function within 3-4 months of allogeneic, syngeneic, or autologous marrow grafting for hematologic malignancy. Blood 1982, 59: 844-850.

Wahren B, Gahrton G, Linde A, Ljungman P, Lonnqvist B, Ringden O. et al. Transfer and persistence of viral antibody-producing cells in bone marrow transplantation. *J Infect Dis* 1984, 150: 358-365.

Matsue K, Lum L G, Witherspoon R P, Storb R Proliferative and differentiative responses of B cells from human marrow graft recipients to T cell-derived factors. *Blood* 1987, 69: 308-315.

Lum L G, Seigneuret M C, Storb R The transfer of antigen-specific humoral immunity from marrow donors to marrow recipients. *J Clin Immunol* 1986, 6: 389-396.

Stevens P H, Saxon A. Immunoregulation in humans. Control of anti-tetanus toxoid antibody production after booster immunization. *J Clin Invest* 1978, 62: 1154-1160.

Saxon A, Mitsuyasu R, Stevens R, Champlin R E, Kimata H, Gale R P. Designed transfer of specific immune responses with bone marrow transplantation. *J Clin Invest* 1986, 78: 959-967.

Moon E K, Wang, L-C S, Dolfi D V, et al. Multifactorial T cell hypofunction that is reversible can limit the efficacy of chimeric antibody receptor-transduced human T cells in solid tumors. *Clin Cancer Res* 2014, 20(16): 4262-4273.

Stromnes I M, Schmitt T M, Hulbert A, Brockenbrough J S, et al. T cells engineered against a native antigen can surmount immunoogic and physical barriers to treat pancreatic ductal adenocarcinoma. *Cancer Cell* 2015, 28(5): 638-652.

Weiss M A, Maslak P G, Jurcic J G, Scheinberg D A, Aliff T B, Lamanna N, Frankel S R, Kossman S E, Horgan D. Petostatin and cyclophosphamide: an effective new regimen in previously treated patients with chronic lymphocytic leukemia. *J Clin Oncol* 2003, 21: 1278-1284.

Pavletic S Z, Bociek R G, Foran J M, Rubocki R J, Kuszynski C A, et al. Lymmphodepleting effects and safety of pentostatin for nonmyeloablative allogeneic stem-cell transplantation. *Transplantation* 2003, 76(5): 877-881.

Turtle C J, Hanafi L-A, Berger C, Sommermeyer D, Pender B, Robinson, E M, et al. Addition of flydarabine to cyclophosphamide lymphodepletion improves in vivo expansion of CD19 chimeric antigen receptor-modified T cells and clinical outcome in adults with B cell acute lymphoblastic leukemia. *Blood* 2015, 126: 3773-3780.

Miller J S, Weisdorf D J, Burns L J, Slungaard A, Wagner J E, Verneris M R, Cooley S, et al. Lymphodepletion followed by donor lymphocyte infusion (DLI) causes significantly more acute graft-versus-host disease than DLI alone. *Blood* 2007, 110: 2761-2763.

Storek J, Zhao Z, Liu Y, Nash R, McSweeney P, Maloney D G. Early recovery of CD4 T cell receptor diversity after "lymphoablative" conditioning and autologous CD34 cell transplantation. *Biol Blood Marrow Transplant* 2008, 14(12): 1373-1379

Chang A E, Li Q, Jiang G, Sayre D M, Braun™, Redman B G. Phase I I trial of autologous tumor vaccination, anti-CD3-activated vaccine-primed Ilymphocytes, and interleukin-2 in stage I V renal cell cancer 2003, *J Clin Oncol* 21:884-890.

Fowler D H, Mossoba M E, Steinberg S M, Halverson D C, Stroncek D, Khuu, H M, et. al. Phase 2 clinical trial of rapamycin-resistant donor CD4+Th2/Th1 (T-Rapa) cells after low-intensity allogeneic hematopoietic cell transplantation. *Blood* 2013, 121(15):2864-2874.

Gargett T, Brown M P. Different cytokine and stimulation conditions influence the expansion and immune phenotype of third-generation chieric antigen receptor T cells specific for tumor antigen GD2. *Cytotherapy* 2015, 17(4): 487-495.

Caserta S, Alessi P, Basso V, Mondino A. 11-7 is superior to IL-2 for ex-vivo expansion of tumour-specific CD4+ T cells. *Eur J Immunol* 2010, 40:470-479.

Cha E, Graham L, Manjili M H, Bear H D. IL-7+IL-15 are superior to IL-2 for the ex-vovo expansion of 4T1 mammary carcinoma-specific T cells with greater efficiency against tumors in vivo. *Breast Cancer Res Treat* 2010, 122:359-369.

What is claimed is:

1. A method of improving the immunotherapeutic response of a cancer patient vaccinated with a cancer specific T cell, the method comprising steps of:
   i. Vaccinating a cancer patient with a cancer specific T-cell vaccine cell population comprising T-cells in an amount sufficient to prime immune specific anti-tumor T-cells of the cancer patient, wherein the cancer specific T-cell vaccine cell population is bispecific antibody armed activated T-cells (BATs), Chimeric Antigen Receptor T-cells (CAR-T), Tumor infiltrating lymphocytes (TILs), T-cell receptor engineered T cells (TCR transgenic), or bispecific antibody armed T-Rapa cells;
   ii. Collecting the primed immune specific anti-tumor T-cells from the peripheral blood of the cancer patient;
   iii. Culturing the collected primed immune specific anti-tumor T cells ex vivo in a medium with anti-CD3 or with anti-CD3 and anti-CD28 antibodies, wherein the collected primed immune specific anti-tumor T cells are expanded;
   iv. Testing the cultured collected primed immune specific anti-tumor T cells for cytotoxicity and comparing the cultured collected primed immune specific anti-tumor T cells cytotoxicity to cytotoxicity of ex-vivo cultured activated T-cells of the pre-vaccination patient; and
   v. Upon determining that the collected primed immune specific anti-tumor T cells cytotoxicity exceeds ex-vivo cultured activated T-cells of the pre-vaccination patient cytotoxicity, reinfusing the cultured primed immune specific anti-tumor T cells into the cancer patient in vivo, wherein the reinfused T-cells are not genetically modified and not armed with at least a portion of an antibody, and wherein the cancer patient is treated with neither IL-2 nor GM-CSF during the steps i-v.

2. The method of claim 1, wherein the cancer specific T cell vaccine cell population further includes dendritic cells.

3. The method of claim 1 wherein the cancer specific T-cell vaccine cell population is an autologous cancer specific T-cell vaccine cell population.

4. The method of claim 1, wherein the cancer specific T-cell vaccine cell population is an allogeneic cancer specific T-cell vaccine cell population.

5. The method of claim 1 wherein the reinfusing occurs between 1-15 times for a total of up to 160 Billion cultured T-cells total.

6. The method of claim 1, further comprising suppressing the T-cell population in the cancer patient prior to reinfusing.

7. The method of claim 6, wherein the suppressing is due to myeloablation or chemotherapeutic treatment.

8. The method of claim 1, wherein the cancer specific T-cell vaccine cell population used to vaccinate the cancer patient is between 0.06-160 Billion T-cells.

9. The method of claim 1, wherein the cancer patient has a cancer that is a solid tumor or a cancer of hematologic origin.

10. The method of claim 9, wherein the solid tumor is pancreatic, breast, liver, ovarian, brain, neuroblastoma, prostate, lung or colon/colorectal cancer.

11. The method of claim 1, wherein a cancer of the cancer patient comprises a tumor and wherein a volume of the tumor is reduced by at least 10% using the steps i-v.

12. The method of claim 1, wherein levels of one or more cytokines of the cancer patient increase after the cancer patient undergoes the reinfusion.

13. The method of claim 1, wherein following the steps i-iv the cancer patient exhibits an elevated level of one or more of $CD^{4+}$ cells and $CD^{8+}$ cells and wherein a cancer antigen specific TCR repertoire of the cancer patient's T-cells is increased using the steps i-v.

14. The method of claim 1, wherein the patient experiences an increase in endogenous specific anti-tumor cytotoxicity that directly correlates with a Spearman correlation r-value of 1.00 and a p-value of 0.002 with an increase in time-to-progression and survival as a result of the steps i-v.

* * * * *